United States Patent
Wu et al.

(10) Patent No.: US 11,666,380 B2
(45) Date of Patent: *Jun. 6, 2023

(54) APPARATUS, SYSTEMS, AND METHODS FOR ACHIEVING INTRAVASCULAR, THERMALLY-INDUCED RENAL NEUROMODULATION RELATED APPLICATION

(71) Applicant: Medtronic Ireland Manufacturing Unlimited Company, Dublin (IE)

(72) Inventors: Andrew Wu, Los Altos Hills, CA (US); Benjamin J. Clark, Redwood City, CA (US); Denise Zarins, Saratoga, CA (US); Erik Thai, San Jose, CA (US)

(73) Assignee: MEDTRONIC IRELAND MANUFACTURING UNLIMITED COMPANY, Dublin (IE)

(*) Notice: Subject to any disclaimer, the term of this patent is extended or adjusted under 35 U.S.C. 154(b) by 326 days.

This patent is subject to a terminal disclaimer.

(21) Appl. No.: 16/820,444

(22) Filed: Mar. 16, 2020

(65) Prior Publication Data
US 2020/0214765 A1 Jul. 9, 2020

Related U.S. Application Data

(63) Continuation of application No. 15/654,018, filed on Jul. 19, 2017, now abandoned, which is a
(Continued)

(30) Foreign Application Priority Data

Aug. 14, 2009 (EP) .................................... 09167937

(51) Int. Cl.
  *A61B 18/14* (2006.01)
  *A61B 18/12* (2006.01)
  (Continued)

(52) U.S. Cl.
  CPC ...... *A61B 18/1492* (2013.01); *A61B 18/1206* (2013.01); *A61M 25/0141* (2013.01);
  (Continued)

(58) Field of Classification Search
  CPC . A61B 18/02; A61B 18/1206; A61B 18/1492; A61B 18/18; A61B 18/24;
  (Continued)

(56) References Cited

U.S. PATENT DOCUMENTS

| 5,322,064 A * | 6/1994 | Lundquist | A61M 25/0051 607/122 |
| 2003/0125720 A1* | 7/2003 | Woodard | A61B 18/1492 606/29 |
| 2009/0093806 A1* | 4/2009 | Govari | A61B 5/6843 606/34 |

* cited by examiner

*Primary Examiner* — Khadijeh A Vahdat
(74) *Attorney, Agent, or Firm* — Shumaker & Sieffert, P.A.

(57) ABSTRACT

Apparatus, systems, and methods for achieving thermally-induced renal neuromodulation by intravascular access are disclosed herein. One aspect of the present application, for example, is directed to apparatuses, systems, and methods that incorporate a treatment device comprising an elongated shaft. The elongated shaft is sized and configured to deliver a thermal element to a renal artery via an intravascular path. Thermally-induced renal neuromodulation may be achieved via direct and/or via indirect application of thermal energy to heat or cool neural fibers that contribute to renal function, or of vascular structures that feed or perfuse the neural fibers.

20 Claims, 32 Drawing Sheets

Related U.S. Application Data continuation of application No. 14/636,459, filed on Mar. 3, 2015, now abandoned, which is a continuation of application No. 14/284,474, filed on May 22, 2014, now abandoned, which is a continuation of application No. 12/910,631, filed on Oct. 22, 2010, now Pat. No. 8,777,942, which is a continuation of application No. 12/545,648, filed on Aug. 21, 2009, now Pat. No. 8,652,129, which is a continuation-in-part of application No. 12/495,691, filed on Jun. 30, 2009, now abandoned.

(60) Provisional application No. 61/142,128, filed on Dec. 31, 2008.

(51) Int. Cl.
| | |
|---|---|
| *A61M 25/01* | (2006.01) |
| *A61B 18/02* | (2006.01) |
| *A61B 18/18* | (2006.01) |
| *A61B 18/24* | (2006.01) |
| *A61B 17/00* | (2006.01) |
| *A61N 7/00* | (2006.01) |
| *A61B 90/00* | (2016.01) |
| *A61B 18/00* | (2006.01) |

(52) U.S. Cl.
CPC ............... *A61B 18/02* (2013.01); *A61B 18/18* (2013.01); *A61B 18/24* (2013.01); *A61B 90/39* (2016.02); *A61B 2017/003* (2013.01); *A61B 2018/00172* (2013.01); *A61B 2018/00404* (2013.01); *A61B 2018/00434* (2013.01); *A61B 2018/00511* (2013.01); *A61B 2018/00577* (2013.01); *A61B 2018/00648* (2013.01); *A61B 2018/00791* (2013.01); *A61B 2018/00875* (2013.01); *A61N 2007/003* (2013.01)

(58) Field of Classification Search
CPC ........... A61B 2018/00172; A61B 2018/00404; A61B 2018/00434; A61B 2018/00511; A61B 2017/003
USPC ...................................... 606/32–50
See application file for complete search history.

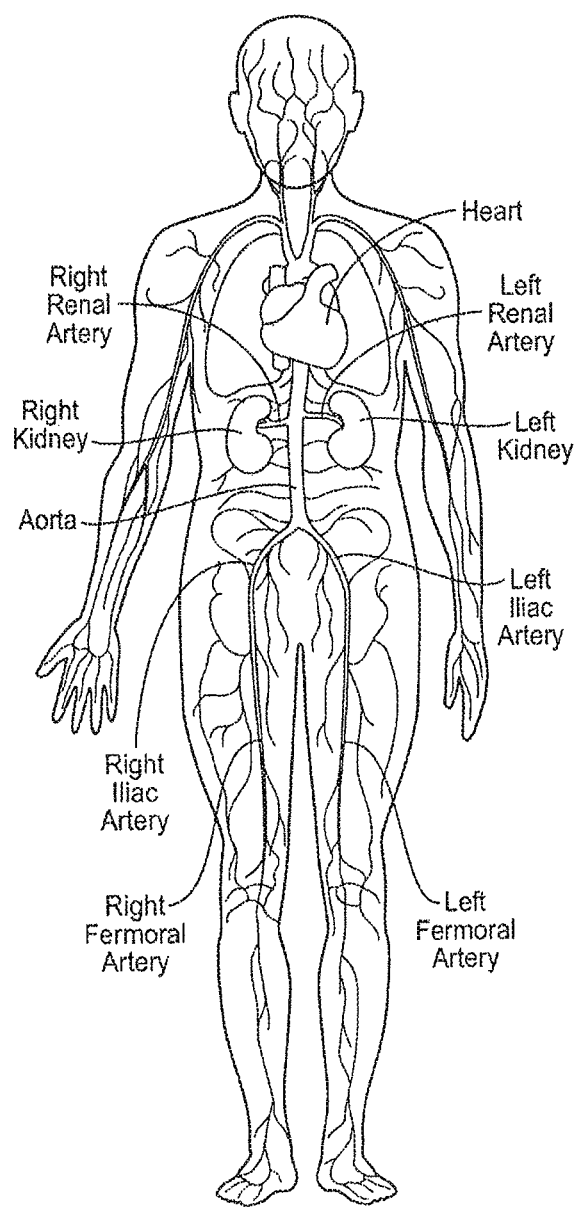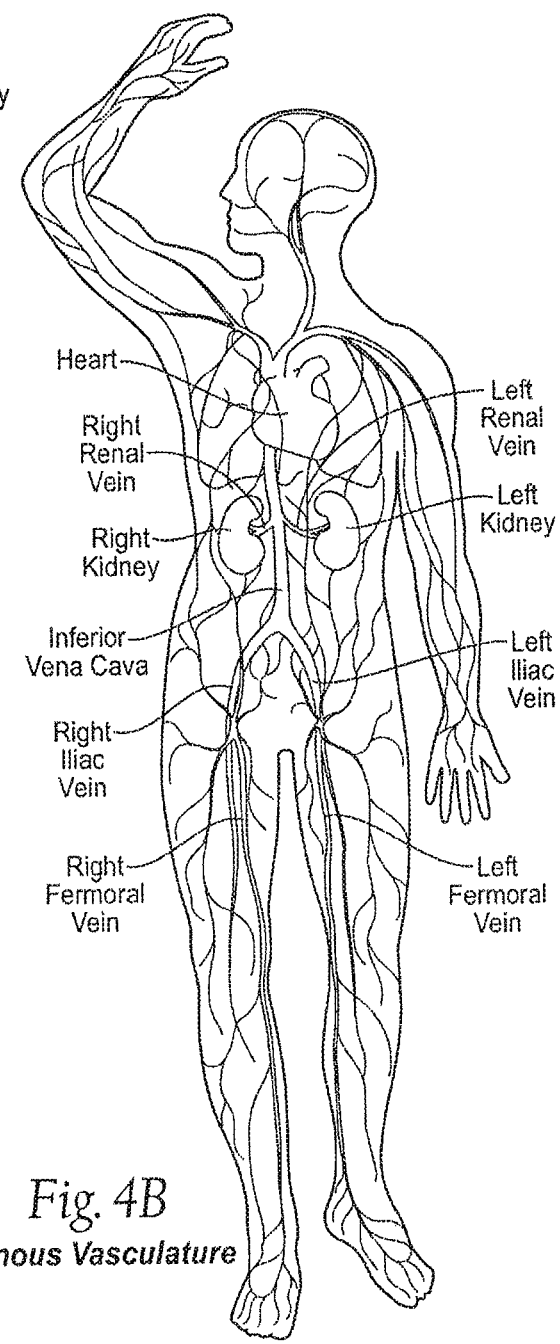
Fig. 4A
*Arterial Vasculature*
Fig. 4B
*Venous Vasculature*

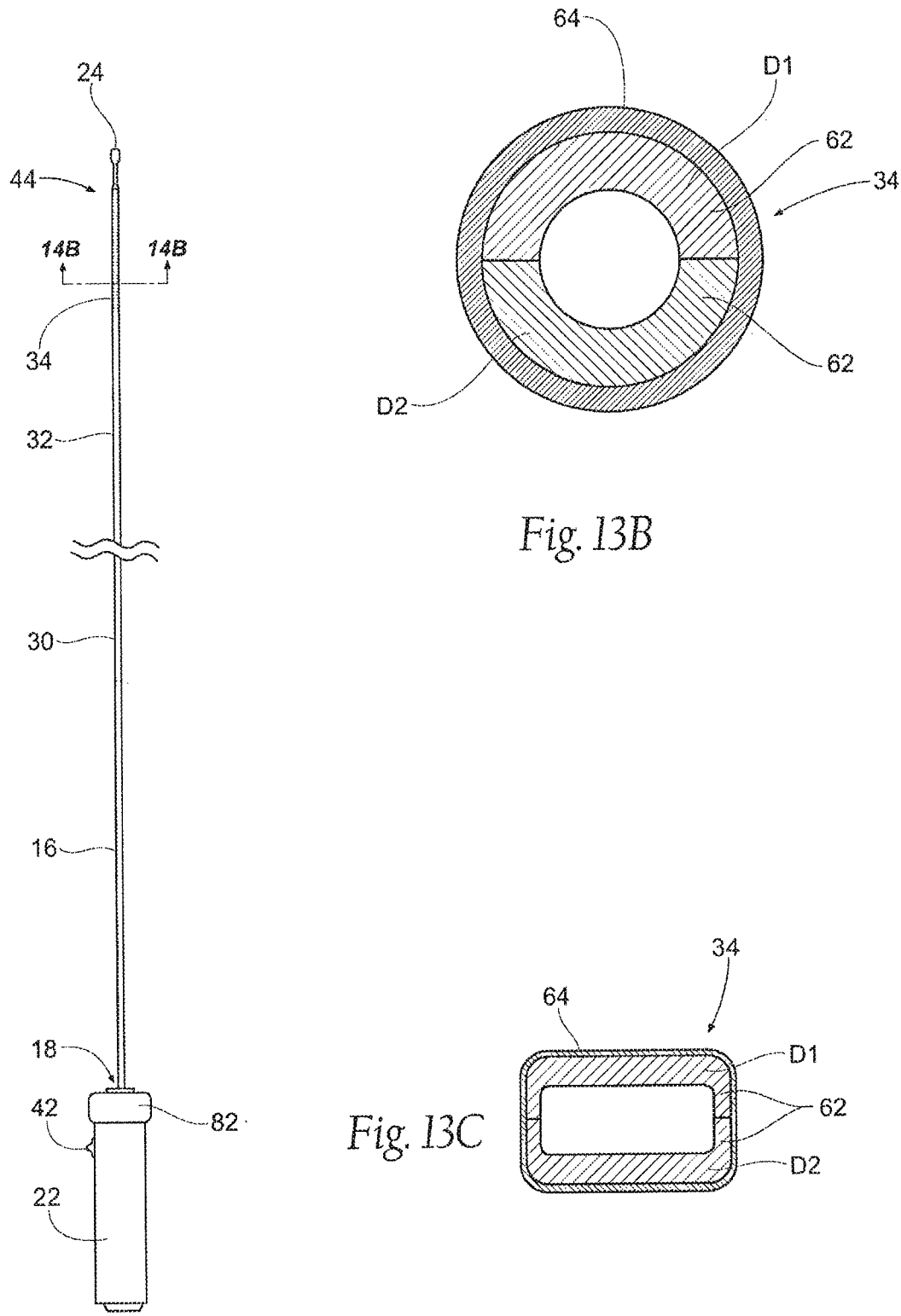

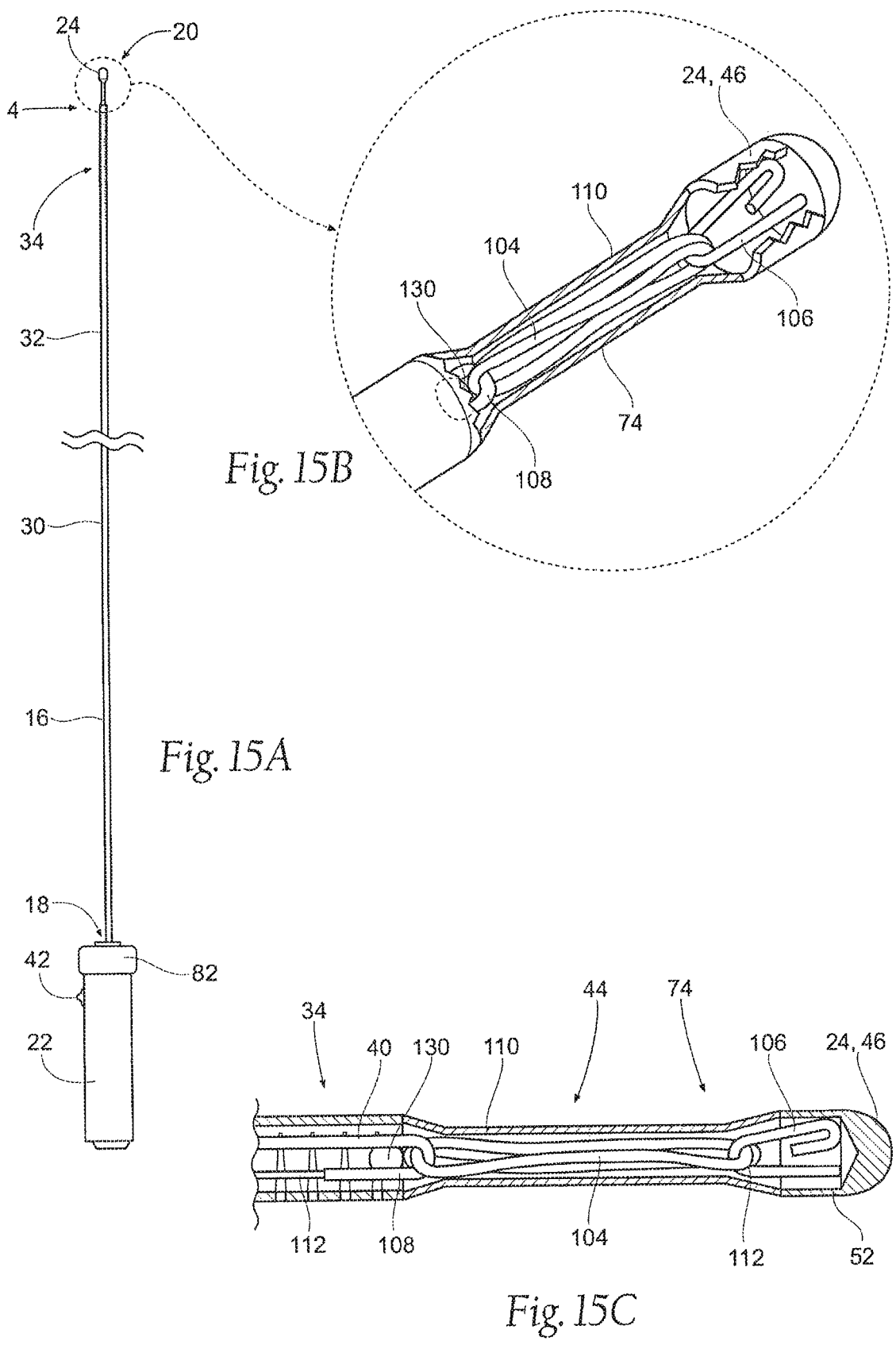

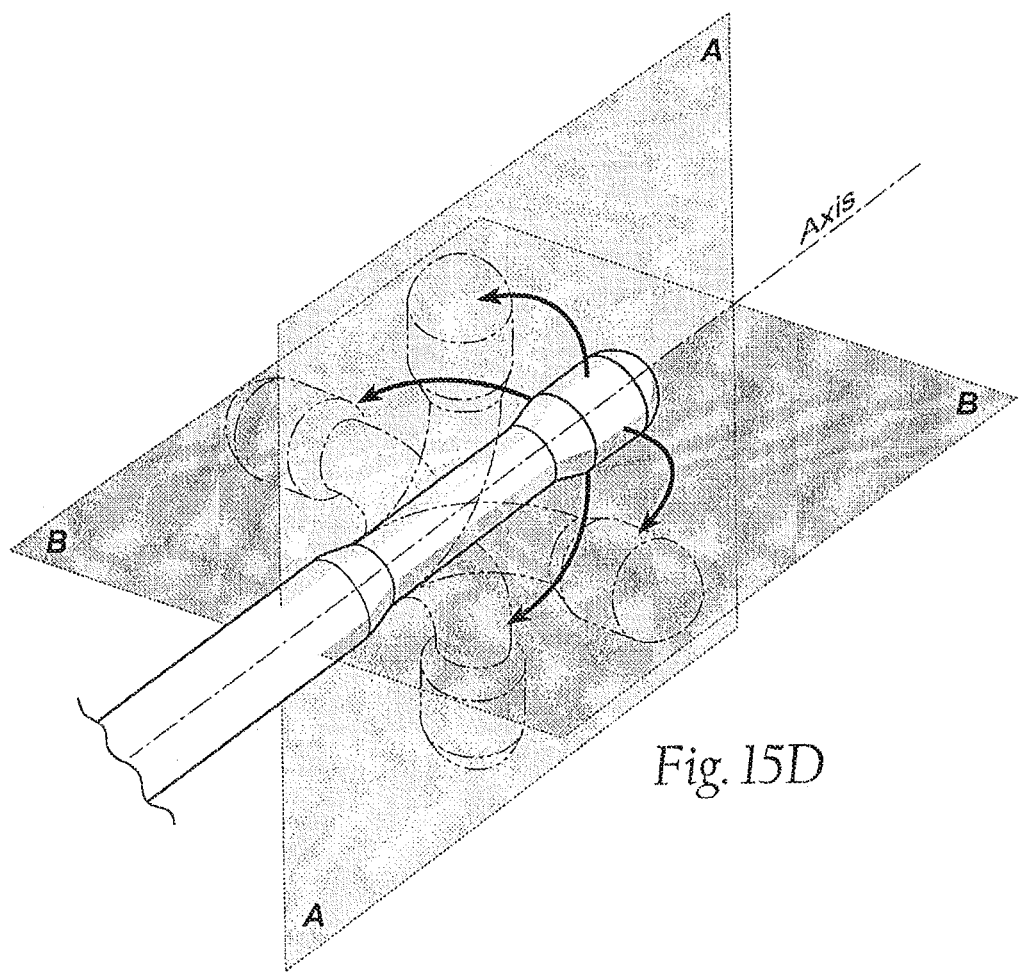
Fig. 15D
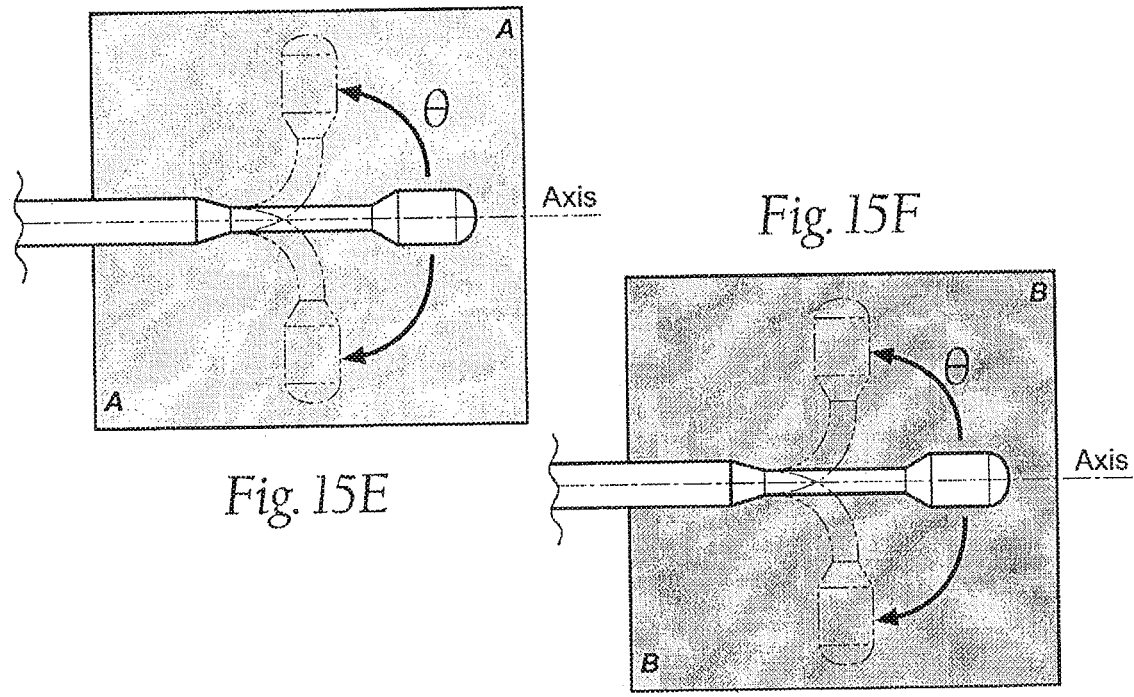
Fig. 15E
Fig. 15F

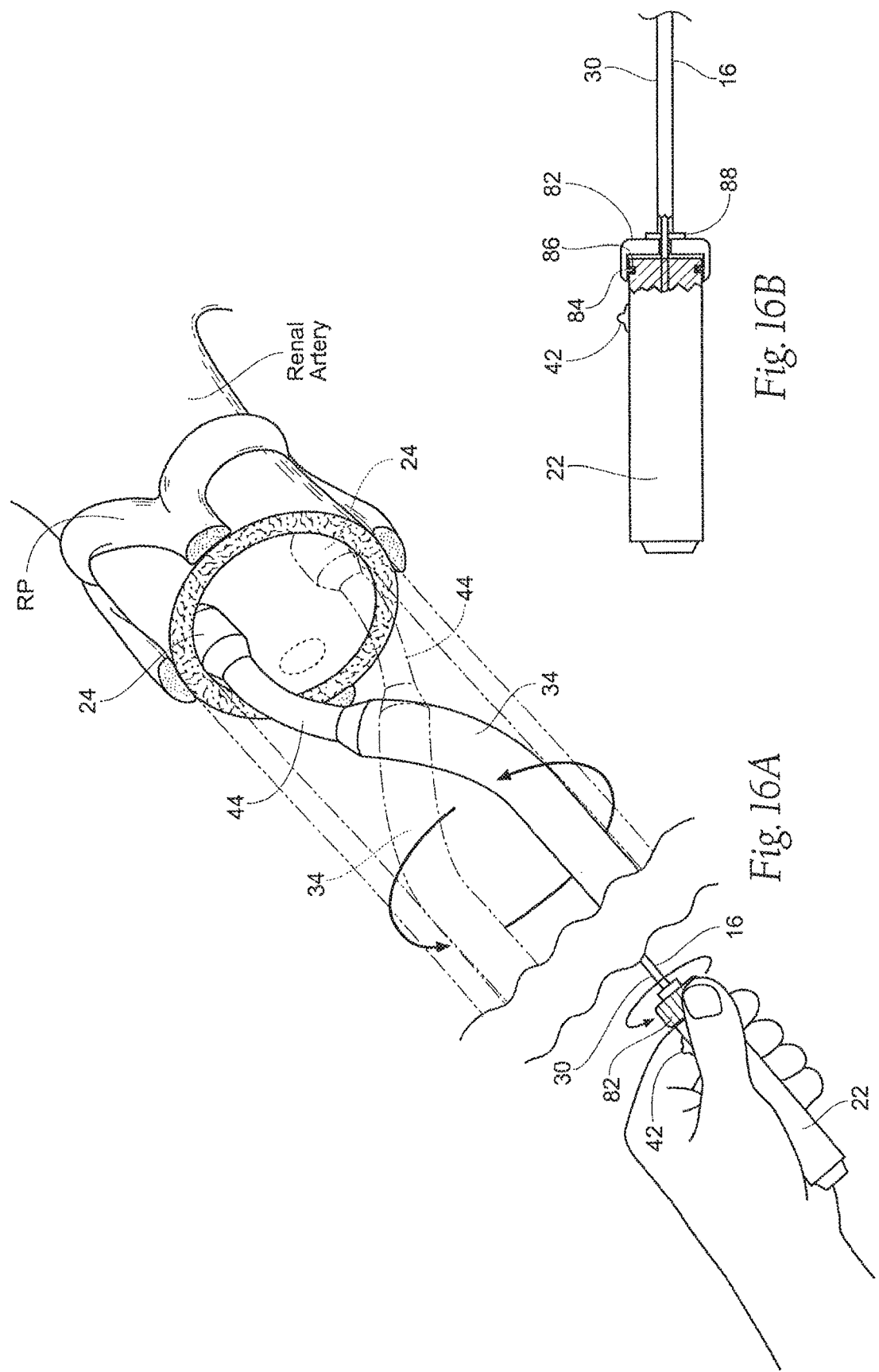

APPARATUS, SYSTEMS, AND METHODS FOR ACHIEVING INTRAVASCULAR, THERMALLY-INDUCED RENAL NEUROMODULATION RELATED APPLICATION

CROSS-REFERENCE TO RELATED APPLICATION(S)

The present application claims the benefit of the flowing pending applications:

This present application is a Continuation of U.S. Patent application Ser. No. 15/654,018, filed on Jul. 19, 2017, now abandoned; which is a Continuation of U.S. patent application Ser. No. 14/636,459, filed on Mar. 3, 2015, now abandoned; which is a Continuation of U.S. patent application Ser. No. 14/284,474, filed on May 22, 2014, now abandoned; which is a Continuation of U.S. patent application Ser. No. 12/910,631, filed on Oct. 22, 2010, now U.S. Pat. No. 8,777,942; which is a Continuation of U.S. patent application Ser. No. 12/545,648, filed on Aug. 21, 2009, now U.S. Pat. No. 8,652,129; which is a Continuation-in-Part of U.S. patent application Ser. No. 12/495,691, filed on Jun. 30, 2009, now abandoned. U.S. patent application Ser. No. 12/495,691 claims priority to U.S. Provisional Patent Application No. 61/142,128, filed on Dec. 31, 2008.

All of these applications are incorporated herein by reference in their entireties.

The present application also claims priority to European Patent Application No. 09167937.3 filed Aug. 14, 2009, now European Patent No. 2 204 134;

European Patent Application No. 09168202.1 filed Aug. 14, 2009, now abandoned; and European Patent Application No. 09168204.7 filed Aug. 14, 2009, now European Patent No. 2 206 477.

All of these applications are incorporated herein by reference in their entireties.

TECHNICAL FIELD

The technologies disclosed in the present application generally relate to apparatus, systems, and methods for intravascular neuromodulation. More particularly, the technologies disclosed herein relate to apparatus, systems, and methods for achieving intravascular renal neuromodulation via thermal heating.

BACKGROUND

Hypertension, heart failure and chronic kidney disease represent a significant and growing global health issue. Current therapies for these conditions include non-pharmacological, pharmacological and device-based approaches. Despite this variety of treatment options the rates of control of blood pressure and the therapeutic efforts to prevent progression of heart failure and chronic kidney disease and their sequelae remain unsatisfactory. Although the reasons for this situation are manifold and include issues of non-compliance with prescribed therapy, heterogeneity in responses both in terms of efficacy and adverse event profile, and others, it is evident that alternative options are required to supplement the current therapeutic treatment regimes for these conditions.

Reduction of sympathetic renal nerve activity (e.g., via denervation), can reverse these processes. Ardian, Inc. has discovered that an energy field, including and comprising an electric field, can initiate renal neuromodulation via denervation caused by irreversible electroporation, electrofusion, apoptosis, necrosis, ablation, thermal alteration, alteration of gene expression or another suitable modality.

SUMMARY

The following summary is provided for the benefit of the reader only, and is not intended to limit the disclosure in any way. The present application provides apparatus, systems and methods for achieving thermally-induced renal neuromodulation by intravascular access.

One aspect of the present application provides apparatuses, systems, and methods that incorporate a treatment device comprising an elongated shaft. The elongated shaft is sized and configured to deliver a thermal heating element to a renal artery via an intravascular path that includes a femoral artery, an iliac artery, and the aorta. Different sections of the elongated shaft serve different mechanical functions when in use. The sections are differentiated in terms of their size, configuration, and mechanical properties for (i) percutaneous introduction into a femoral artery through a small-diameter access site; (ii) atraumatic passage through the tortuous intravascular path through an iliac artery, into the aorta, and into a respective left/right renal artery, including (iii) accommodating significant flexure at the junction of the left/right renal arteries and aorta to gain entry into the respective left or right renal artery; (iv) accommodating controlled translation, deflection, and/or rotation within the respective renal artery to attain proximity to and a desired alignment with an interior wall of the respective renal artery; and (v) allowing the placement of a thermal heating element into contact with tissue on the interior wall in an orientation that optimizes the active surface area of the thermal heating element.

BRIEF DESCRIPTION OF THE DRAWINGS

FIGS. 4A and 4B are, respectively, anatomic views of the arterial and venous vasculatures of a human.

FIGS. 13A to 13C show alternative embodiments of the intermediate flexure zone of the elongated shaft of the treatment device shown in FIG. 5.

FIGS. 15A to 15C show a representative embodiment of the distal flexure zone of the elongated shaft of the treatment device shown in FIG. 5.

FIGS. 15D to 15F show multiple planar views of the bending capability of the distal flexure zone corresponding to the elongated shaft of the treatment device shown in FIG. 5.

FIGS. 16A and 16B show a representative embodiment of a rotational control mechanism coupled to the handle of the treatment device shown in FIG. 5.

FIG. 20 shows an energy delivery algorithm corresponding to the energy generator of the system shown in FIG. 5.

DETAILED DESCRIPTION

Although the disclosure hereof is detailed and exact to enable those skilled in the art to practice the disclosed technologies, the physical embodiments herein disclosed merely exemplify the various aspects of the invention, which may be embodied in other specific structure. While the preferred embodiment has been described, the details may be changed without departing from the invention, which is defined by the claims.

I. Pertinent Anatomy and Physiology

A. The Kidneys

Figure 1A:
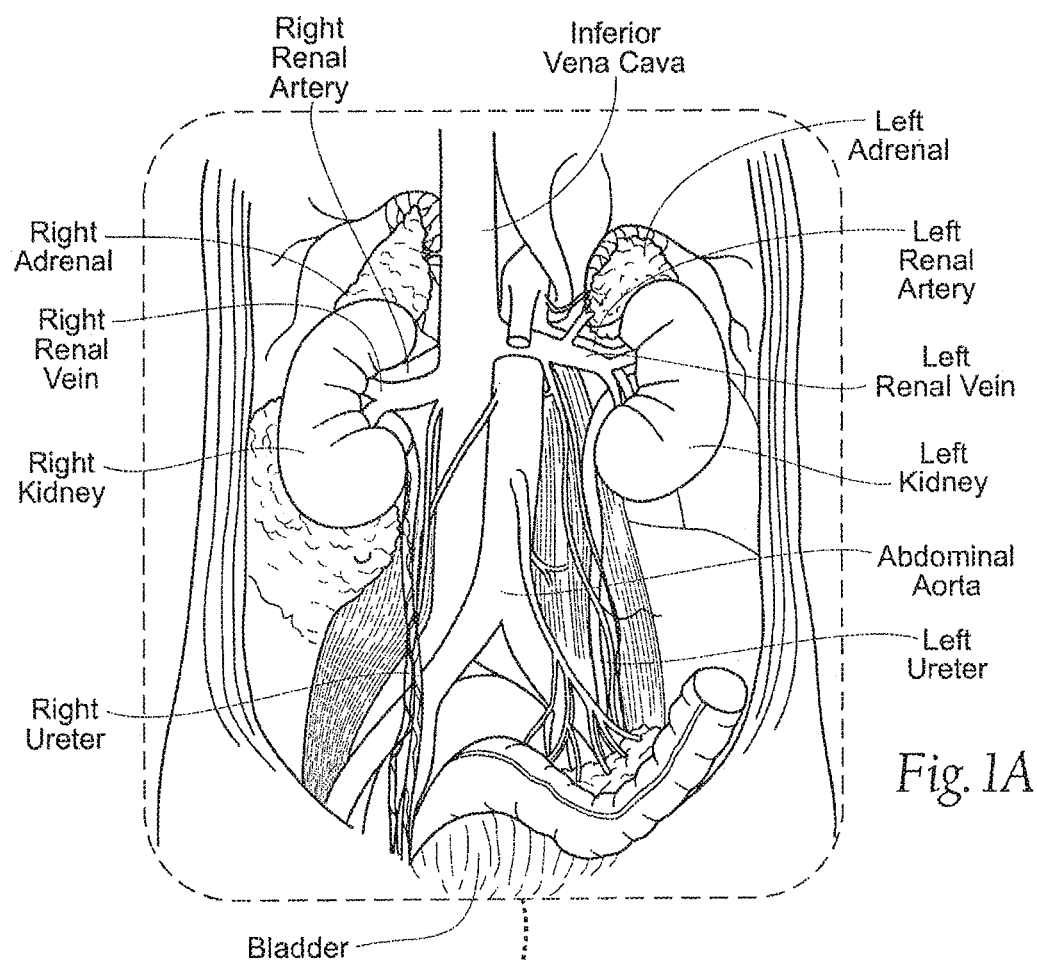
FIG. 1A is an anatomic interior view of a thoracic cavity of a human, with the intestines removed, showing the kidneys and surrounding structures.

FIG. 1A is an anatomic view of the posterior abdominal wall, showing the left and right kidneys, neighboring organs, and major blood vessels. In FIG. 1A, most of the digestive system located within the peritoneum has been omitted for clarity.

In humans, the kidneys are located in the posterior part of the abdominal cavity. There are two, one on each side of the spine. The right kidney sits just below the diaphragm and posterior to the liver. The left kidney sits below the diaphragm and posterior to the spleen. The asymmetry within the abdominal cavity caused by the liver results in the right kidney being slightly lower than the left one, while the left kidney is located slightly more medial.

Above each kidney is an adrenal gland (also called the suprarenal gland). The adrenal glands make hormones, such as (1) cortisol, which is a natural steroid hormone; (2) aldosterone, which is a hormone that helps to regulate the body's water balance; and (3) adrenalin and noradrenaline.

The kidneys are complicated organs that have numerous biological roles.

1. The Blood Filtration Functions

Figure 1B:
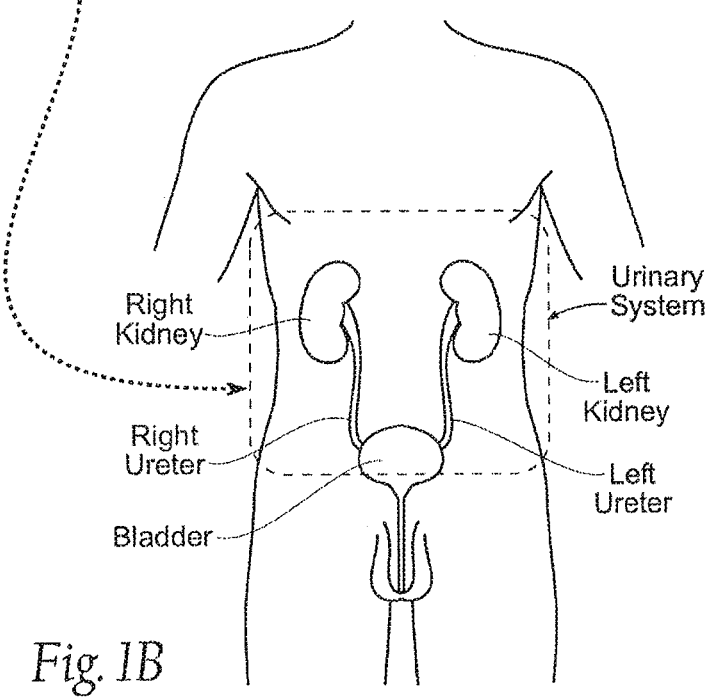
FIG. 1B in an anatomic view of the urinary system of a human, of which the kidneys shown in FIG. 1A form a part.

As FIG. 1B shows, the kidneys are part of the body system called the urinary system, which comprises the kidneys, ureters, bladder, and urethra. Generally speaking, the urinary system filters waste products out of the blood and makes urine.

A primary role of the kidneys is to maintain the homeostatic balance of bodily fluids by filtering and secreting metabolites (such as urea) and minerals from the blood and excreting them, along with water, as urine.

The kidneys perform this vital function by filtering the blood. The kidneys have a very rich blood supply. The kidneys receive unfiltered blood directly from the heart through the abdominal aorta, which branches to the left and right renal arteries to serve the left and right kidneys, respectively. Filtered blood then returns by the left and right renal veins to the inferior vena cava and then the heart. Renal blood flow accounts for approximately one quarter of cardiac output.

In each kidney, the renal artery transports blood with waste products into the respective kidney. As the blood passes through the kidneys, waste products and unneeded water and electrolytes are collected and turned into urine. Filtered blood is returned to the heart by the renal vein. From the kidneys, the urine drains into the bladder down tubes called the ureters (one for each kidney). Another tube called the urethra carries the urine from the bladder out of the body.

Figure 2A:
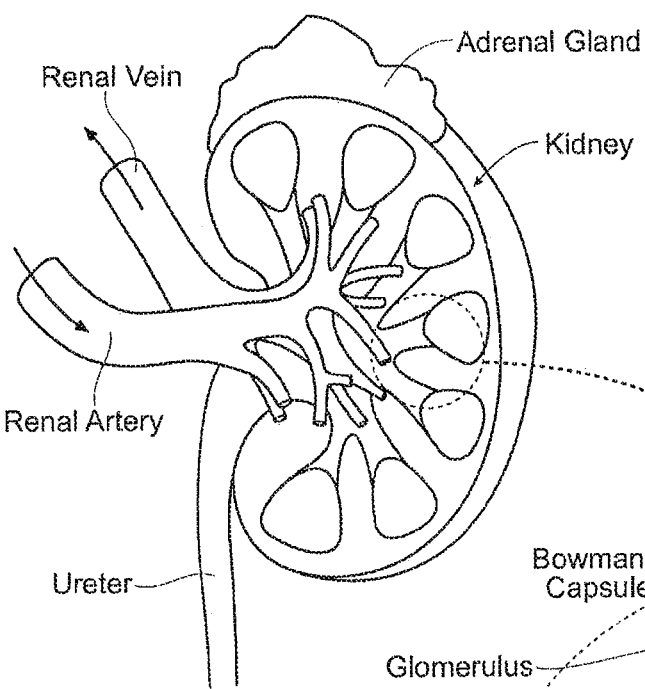
FIGS. 2A, 2B, and 20 are a series of enlarged anatomic views showing various interior regions of a human kidney.
Figure 2B:
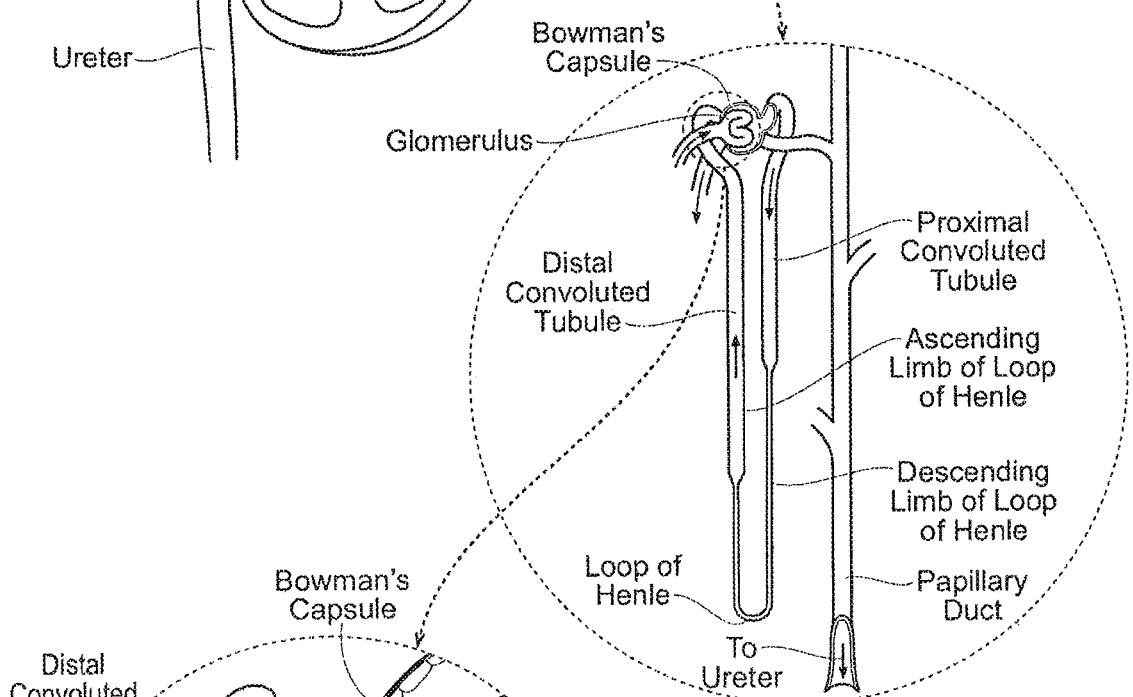
Figure 2C:
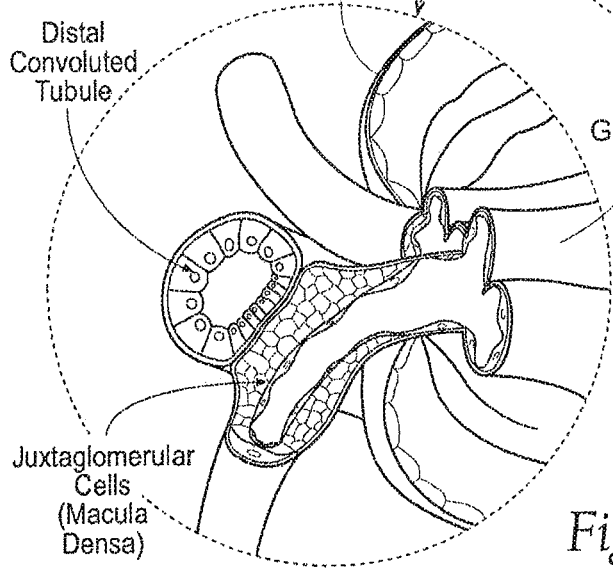

As FIGS. 2A, 2B, and 2C show, inside the kidney, the blood is filtered through very small networks of tubes called nephrons (best shown in FIG. 2B). Each kidney has about 1 million nephrons. As FIG. 2B shows, each nephron is made up of glomeruli, which are covered by sacs (called Bowman's capsules) and connected to renal tubules. Inside the nephrons, waste products in the blood move across from the bloodstream (the capillaries) into the tubules. As the blood passes through the blood vessels of the nephron, unwanted waste is taken away. Any chemicals needed by the body are kept or returned to the bloodstream by the nephrons.

About seventy-five percent of the constituents of crude urine and about sixty-six percent of the fluid are reabsorbed in the first portion of the renal tubules, called the proximal renal tubules (see FIG. 2B). Readsorption is completed in the loop of Henle and in the last portion of the renal tubules, called the distal convoluted tubules, producing urine. The urine is carried by collecting tubule of the nephron to the ureter. In this way, the kidneys help to regulate the levels of chemicals in the blood such as sodium and potassium, and keep the body healthy.

2. The Physiologic Regulation Functions

Because the kidneys are poised to sense plasma concentrations of ions such as sodium, potassium, hydrogen, oxygen, and compounds such as amino acids, creatinine, bicarbonate, and glucose in the blood, they are important regulators of blood pressure, glucose metabolism, and erythropoiesis (the process by which red blood cells are produced).

The kidney is one of the major organs involved in whole-body homeostasis. Besides filtering the blood, the kidneys perform acid-base balance, regulation of electrolyte concentrations, control of blood volume, and regulation of blood pressure. The kidneys accomplish theses homeostatic functions independently and through coordination with other organs, particularly those of the endocrine system.

The kidneys produce and secrete three important hormones: (1) erythropoietin (EPO), which tells the bone marrow to make red blood cells; (2) renin, which regulates blood pressure; and (3) calcitriol (a form of Vitamin D), which helps the intestine to absorb calcium from the diet, and so helps to keep the bones healthy.

Figure 20:
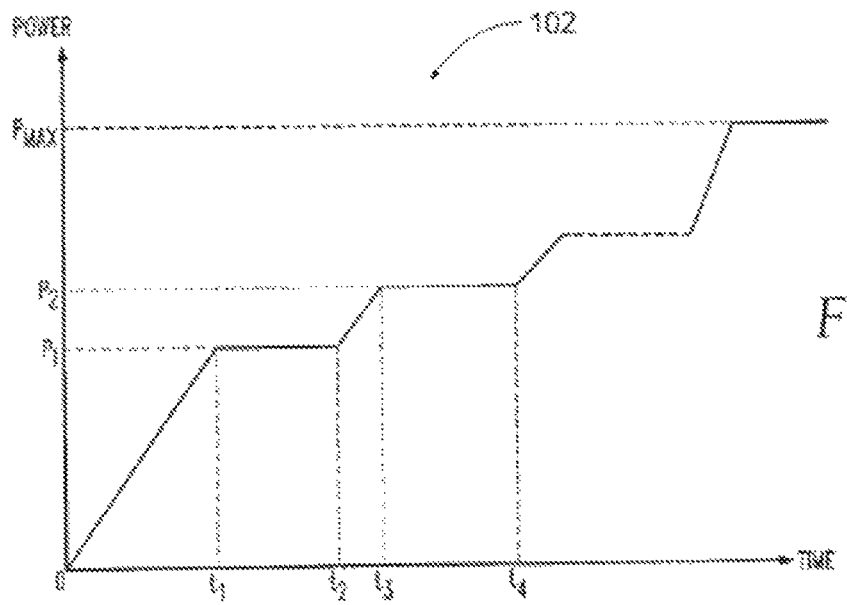

Renin is produced by a densely packed areas of specialized cells, called macula densa, in the region of juxtaglomerular cells, which line the wall of the distal convoluted tubule (DCT) (see FIG. 20). The cells of the macula densa are sensitive to the ionic content and water volume of the fluid in the DOT, producing molecular signals that promote renin secretion by other cells of the juxtaglomerular cell region. As will be described in greater detail later, the release of renin is an essential component of the renin-angiotensin-aldosterone system (RAAS), which regulates blood pressure and volume.

(i) The Renin-Angiotensin System

The renin-angiotensin system (RAS) or the renin-angiotensin-aldosterone system (RAAS) is a hormone system that regulates blood pressure and water (fluid) balance.

When blood pressure is low, the kidneys secrete renin, as explained above. Renin stimulates the production of angiotensin. Angiotensin and its derivatives cause blood vessels to constrict, resulting in increased blood pressure. Angiotensin also stimulates the secretion of the hormone aldosterone from the adrenal cortex. Aldosterone causes the tubules of the kidneys to retain sodium and water. This increases the volume of fluid in the body, which also increases blood pressure.

If the renin-angiotensin-aldosterone system is too active, blood pressure will be too high. There are many drugs which interrupt different steps in this system to lower blood pressure. These drugs are one of the main ways to control high blood pressure (hypertension), heart failure, kidney failure, and harmful effects of diabetes.

B. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation can elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 3A:
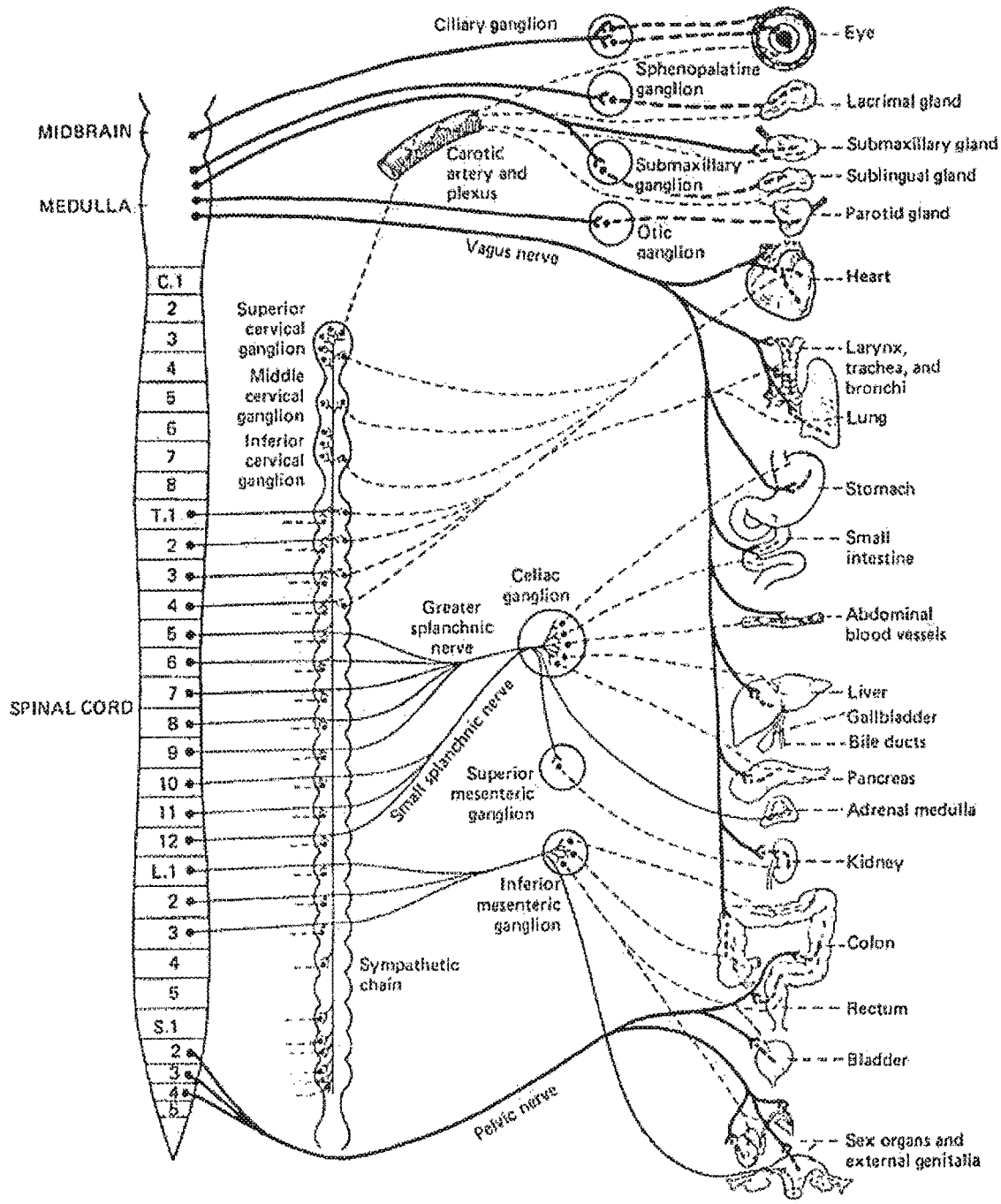
FIG. 3A is a conceptual illustration of the sympathetic nervous system (SNS) and how the brain communicates with the body via the SNS.

As shown in FIG. 3A, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to the either the paravertebral (which lie near the vertebral column) or prevertebral (which lie near the aortic bifurcation) ganglia extending alongside the spinal column.

In order to reach the target organs and glands, the axons must travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic segment and third lumbar segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 3B:
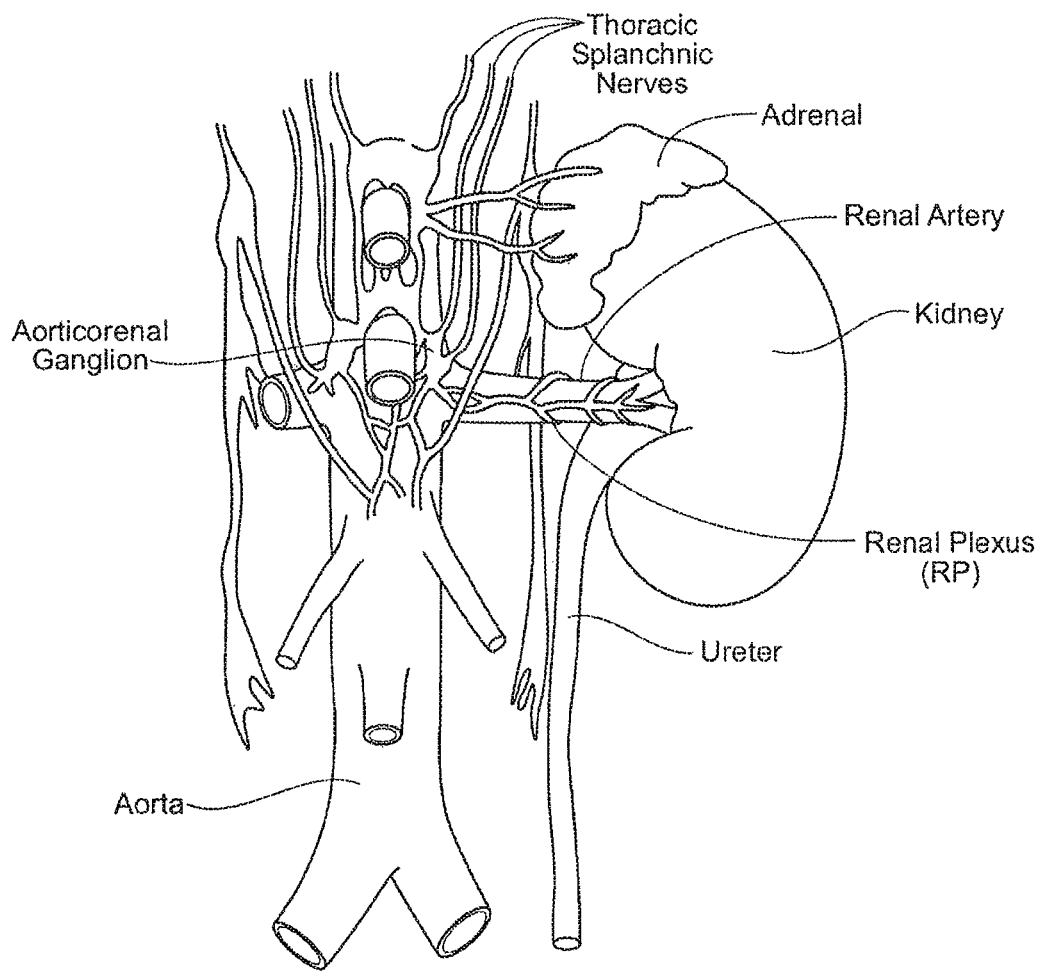
FIG. 3B is an enlarged anatomic view of nerves innervating a left kidney to form the renal plexus surrounding the left renal artery.

As FIG. 3B shows, the kidney is innervated by the renal plexus (RP), which is intimately associated with the renal artery. The renal plexus (RP) is an autonomic plexus that surrounds the renal artery and is embedded within the adventitia of the renal artery. The renal plexus extends along the renal artery until it arrives at the substance of the kidney. Fibers contributing to the renal plexus arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimum) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

3. Renal Sympathetic Neural Activity

Messages travel through the SNS in a bidirectional flow. Efferent messages can trigger changes in different parts of the body simultaneously. For example, the sympathetic nervous system can accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. As described above, pharmaceutical management of the renin-angiotensin-aldosterone system has been the longstanding for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease plasma levels of norepinephrine above the median have been demonstrated to be predictive for both all cause death and death from cardiovascular disease. This is also true for patients suffering from diabetic or contrast nephropathy. There is compelling evidence that suggests that sensory afferent signals originating from the diseased kidneys are major contributors to initiate and sustain elevated central sympathetic outflow in this patient group, which facilitates the occurrence of the well known adverse consequences of chronic sympathetic overactivity such as hypertension, left ventricular hypertrophy, ventricular arrhythmias and sudden cardiac death.

Figure 3C:
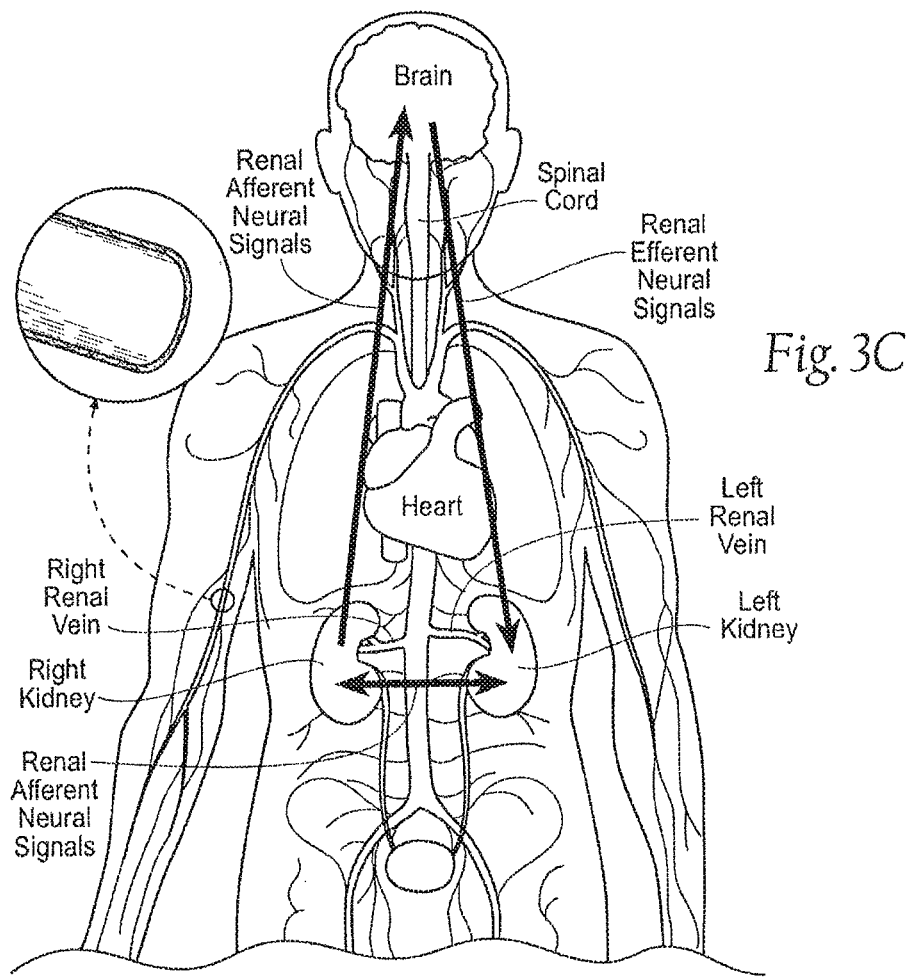
FIGS. 3C and 3D provide anatomic and conceptual views of a human body, respectively, depicting neural efferent and afferent communication between the brain and kidneys
Figure 3D:
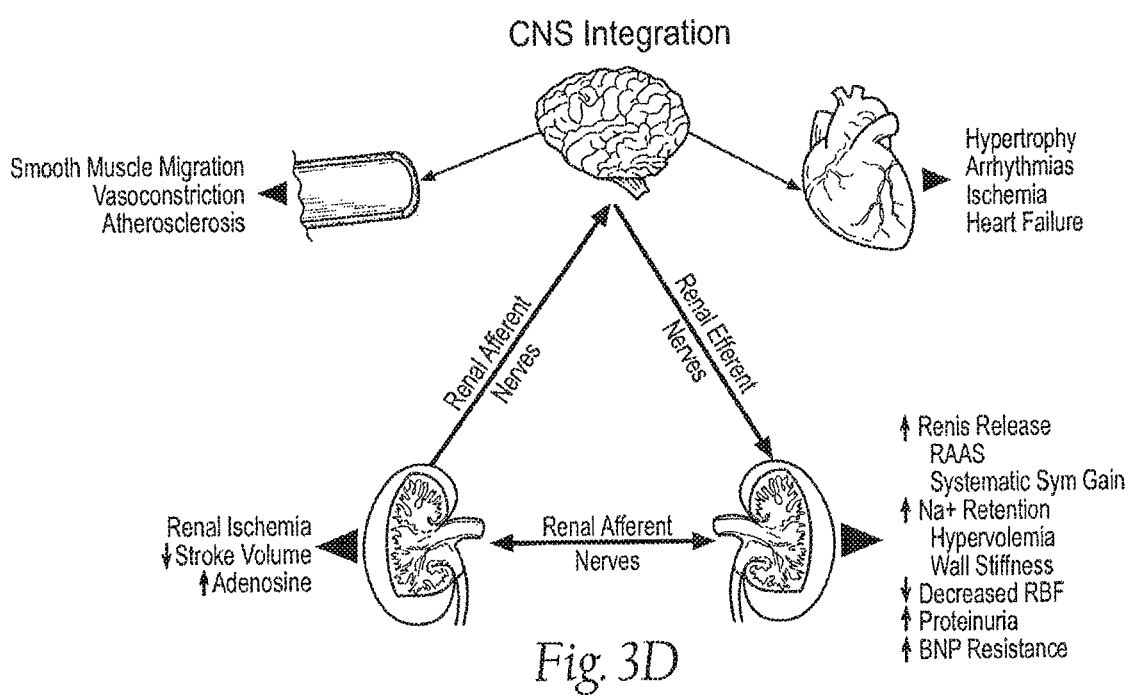

Several forms of "renal injury" can induce activation of sensory afferent signals. For example, renal ischemia, reduction in stroke volume or renal blood flow, or an abundance of adenosine enzyme may trigger activation of afferent neural communication. As shown in FIGS. 3C and 3D, this afferent communication might be from the kidney to the brain or might be from one kidney to the other kidney. These afferent signals are centrally integrated and result in increased sympathetic outflow. This sympathetic drive is directed towards the kidneys, thereby activating the RAAS and inducing increased renin secretion, sodium retention, volume retention and vasoconstriction. Central sympathetic overactivity also impacts other organs and bodily structures innervated by sympathetic nerves such as the heart and the peripheral vasculature, resulting in the described adverse effects of sympathetic activation, several aspects of which also contribute to the rise in blood pressure.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects, and others.

(ii) Renal Sensory Afferent Nerve Activity

The kidneys communicate with integral structures in the central nervous system via renal sensory afferent nerves. Intra-renal pathology, such as ischemic, hypoxia or other injury, results in an increase in renal afferent activity. Renal sensory afferent nerve activity directly influences sympathetic outflow to the kidneys and other highly innervated organs involved in cardiovascular control such as the heart and peripheral blood vessels, by modulating posterior hypothalamic activity.

The physiology therefore suggests that (i) denervation of efferent sympathetic nerves will reduce inappropriate renin release, salt retention, and reduction of renal blood flow, and that (ii) denervation of afferent sensory nerves will reduce the systemic contribution to hypertension through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

C. Additional Clinical Benefits of Renal Denervation

As provided above, renal denervation is likely to be valuable in the treatment of several clinical conditions characterized by increased overall and particularly renal sympathetic activity such as hypertension, metabolic syndrome, diabetes, left ventricular hypertrophy, chronic and end stage renal disease, inappropriate fluid retention in heart failure, cardio-renal syndrome and sudden death. Since the reduction of afferent neural signals contributes to the systemic reduction of sympathetic tone/drive, renal denervation might also be useful in treating other conditions associated with systemic sympathetic hyperactivity. Accordingly, renal denervation can also benefit other organs and bodily structures innervated by sympathetic nerves, including those identified in FIG. 3A. For example, a reduction in central sympathetic drive may reduce the insulin resistance that afflicts people with metabolic syndrome and Type II diabetics. Additionally, patients with osteoporosis are also sympathetically activated and might also benefit from the downregulation of sympathetic drive that accompanies renal denervation.

D. Achieving Intravascular Access to the Renal Artery

As FIG. 4A shows, blood moved by contractions of the heart is conveyed from the left ventricle of the heart by the aorta. The aorta descends through the thorax and branches into the left and right renal arteries (as FIG. 1A also shows). Below the renal arteries, the aorta bifurcates at the left and right iliac arteries. The left and right iliac arteries descend, respectively, through the left and right legs and join the left and right femoral arteries.

As FIG. 4B shows, the blood collects in veins and returns to the heart, through the femoral veins into the iliac veins and into the inferior vena cava. The inferior vena cave branches into the left and right renal veins (as FIG. 1A also shows). Above the renal veins, the inferior vena cave ascends to convey blood into the right atrium of the heart. From the right atrium, the blood is pumped through the right ventricle into the lungs, where it is oxygenated. From the lungs, the oxygenation blood is conveyed into the left atrium. From the left atrium, the oxygenated blood is conveyed by the left ventricle back to the aorta.

As will be described in greater detail later, the femoral artery can be exposed and cannulated at the base of the femoral triangle, just inferior to the midpoint of the inguinal ligament. A catheter can be inserted through this access site, percutaneously into the femoral artery and passed into the iliac artery and aorta, into either the left or right renal artery. This comprises an intravascular path that offers minimally invasive access to a respective renal artery and/or other renal blood vessels.

The wrist, upper arm, and shoulder region provide other locations for introduction of catheters into the arterial system. Catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

II Apparatus, Systems and Methods for Achieving Intravascular, Thermally Induced Renal Neuromodulation A. Overview FIG. 5 shows a system 10 for thermally inducing neuromodulation of a left and/or right renal plexus (RP) through intravascular access.

As just described, the left and/or right renal plexus (RP) surrounds the respective left and/or right renal artery. The renal plexus (RP) extends in intimate association with the respective renal artery into the substance of the kidney. The system thermally induces neuromodulation of a renal plexus (RP) by intravascular access into the respective left or right renal artery.

Figure 6A:
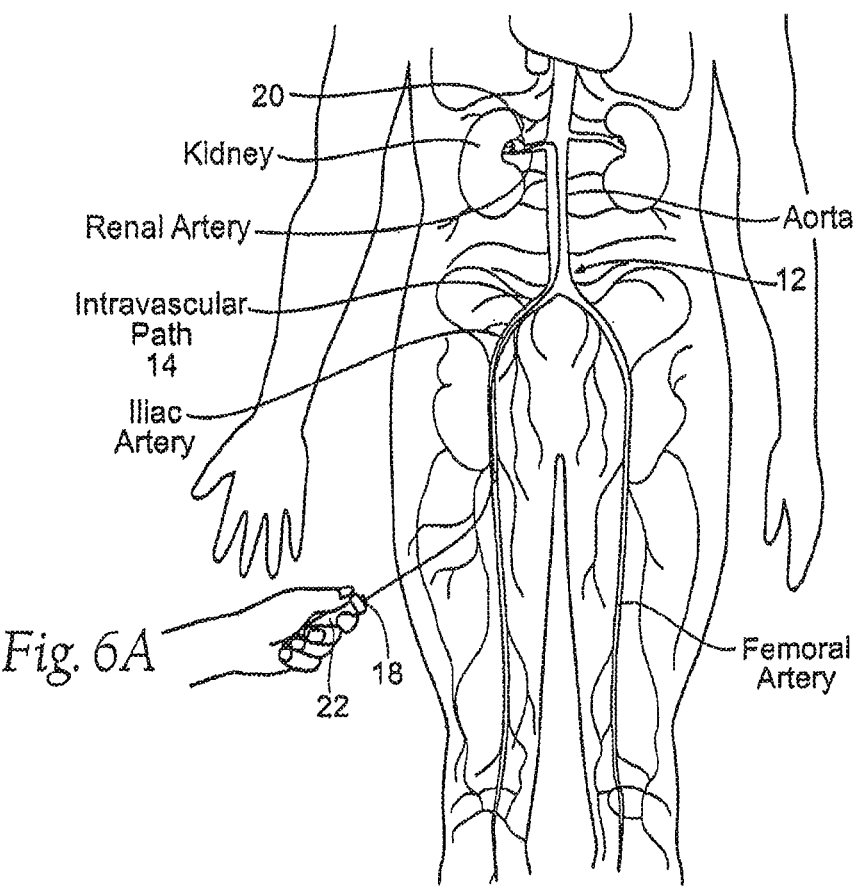
FIGS. 6A and 6B are anatomic views of the intravascular delivery, deflection and placement of the treatment device shown in FIG. 5 through the femoral artery and into a renal artery.

The system 10 includes an intravascular treatment device 12. The treatment device 12 provides access to the renal plexus (RP) through an intravascular path 14 that leads to a respective renal artery, as FIG. 6A shows.

Figure 5:
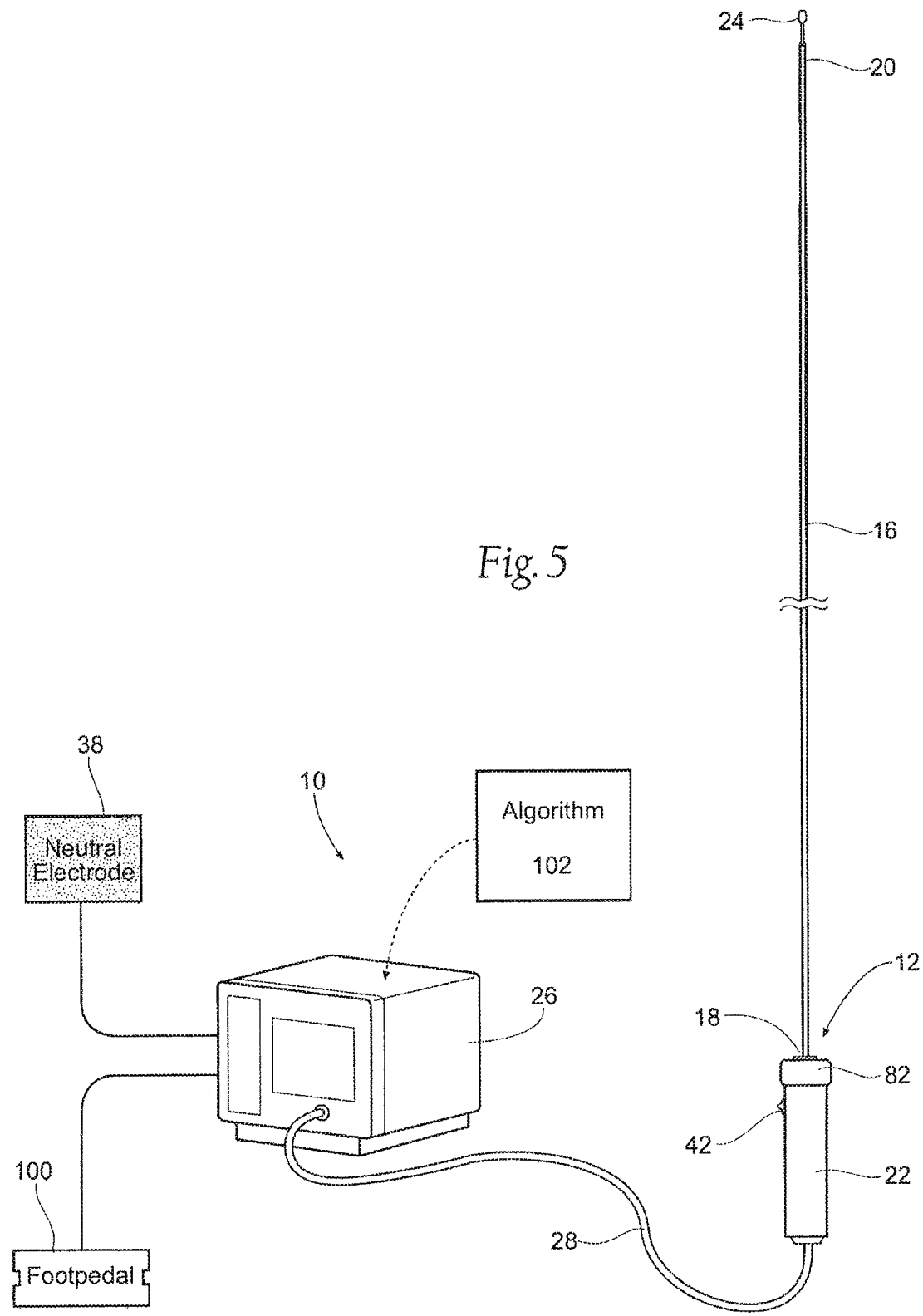
FIG. 5 is a perspective view of a system for achieving intravascular, thermally-induced renal neuromodulation, comprising a treatment device and a generator.

As FIG. 5 shows, the treatment device 12 includes an elongated shaft 16 having a proximal end region 18 and a distal end region 20.

The proximal end region 18 of the elongated shaft 16 includes a handle 22. The handle 22 is sized and configured to be securely held and manipulated by a caregiver (not shown) outside an intravascular path 14 (this is shown in FIG. 6A). By manipulating the handle 22 from outside the intravascular path 14, the caregiver can advance the elongated shaft 16 through the tortuous intravascular path 14. Image guidance, e.g., CT, radiographic, or another suitable guidance modality, or combinations thereof, can be used to aid the caregiver's manipulation.

Figure 6B:
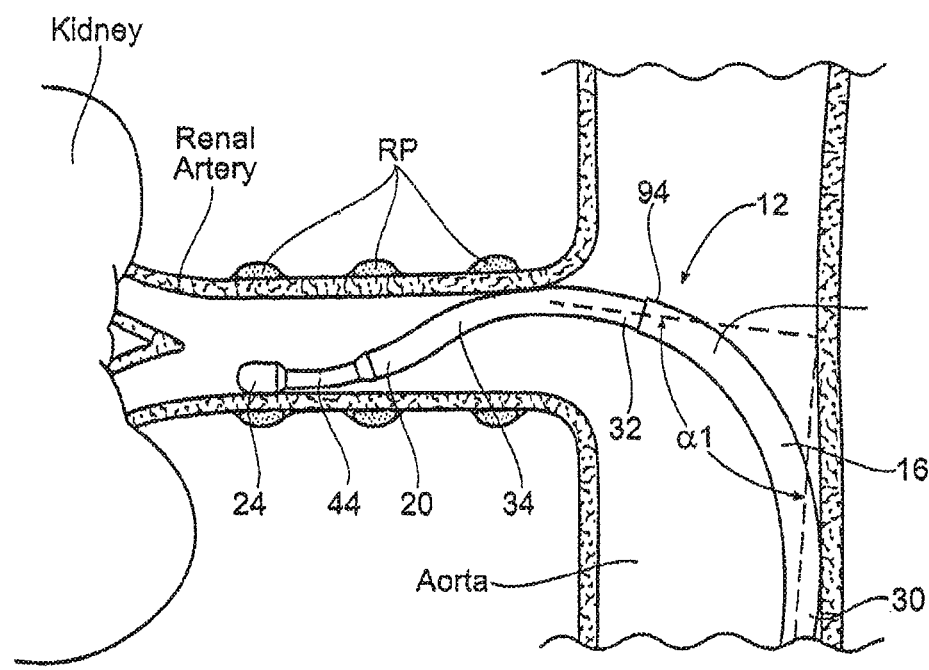
Figure 19A:
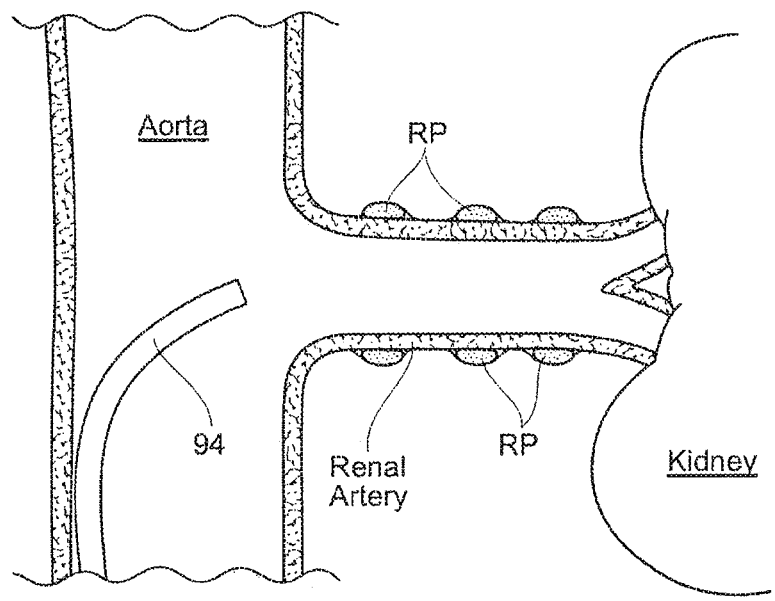
FIGS. 19A to 19H show the intravascular delivery, placement, deflection, rotation, retraction, repositioning and use of a treatment device, like that shown in FIG. 5, to achieve thermally-induced renal neuromodulation from within a renal artery.
Figure 19B:
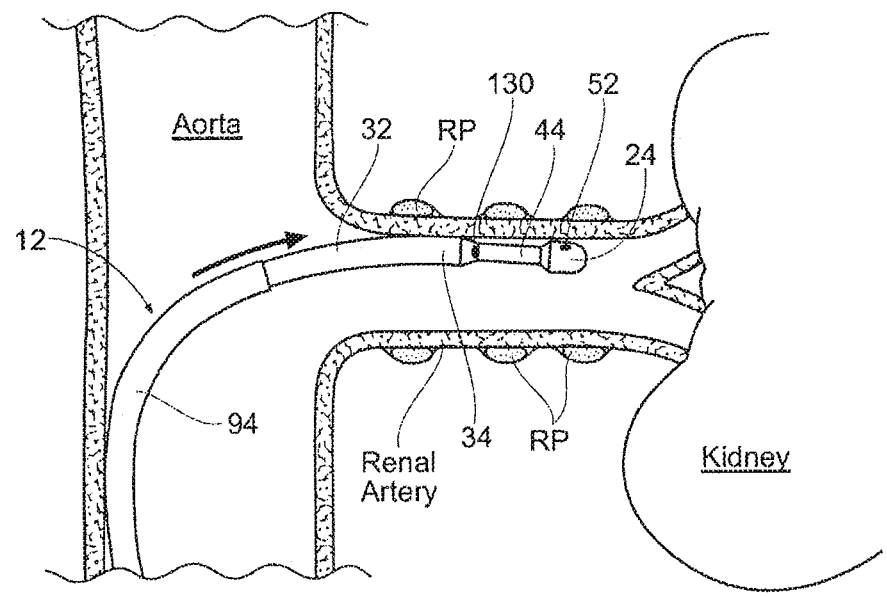

As shown in FIG. 6B, the distal end region 20 of the elongated shaft 16 can flex in a substantial fashion to gain entrance into a respective left/right renal artery by manipulation of the elongated shaft 16. As shown in FIGS. 19A and 19B, the distal end region 20 of the elongated shaft 16 can gain entrance to the renal artery via passage within a guide catheter 94. The distal end region 20 of the elongated shaft 16 carries at least one thermal element 24 (e.g., thermal heating element). The thermal heating element 24 is also specially sized and configured for manipulation and use within a renal artery.

As FIG. 6B shows (and as will be described in greater detail later), once entrance to a renal artery is gained, further manipulation of the distal end region 20 and the thermal heating element 24 within the respective renal artery establishes proximity to and alignment between the thermal heating element 24 and tissue along an interior wall of the respective renal artery. In some embodiments, manipulation of the distal end region 20 will also facilitate contact between the thermal heating element 24 and wall of the renal artery.

As will also be described in greater detail later, different sections of the elongated shaft 16 serve different mechanical functions when in use. The sections are thereby desirably differentiated in terms of their size, configuration, and mechanical properties for (i) percutaneous introduction into a femoral artery through a small-diameter access site; (ii) atraumatic passage through the tortuous intravascular path 14 through an iliac artery, into the aorta, and into a respective left/right renal artery, including (iii) significant flexure near the junction of the left/right renal arteries and aorta to gain entry into the respective left or right renal artery; (iv) controlled translation, deflection, and/or rotation within the respective renal artery to attain proximity to and a desired alignment with an interior wall of the respective renal artery; and (v) the placement of a thermal heating element 24 into contact with tissue on the interior wall.

Referring back to FIG. 5, the system 10 also includes a thermal generator 26 (e.g., a thermal energy generator). Under the control of the caregiver or automated control algorithm 102 (as will be described in greater detail later), the generator 26 generates a selected form and magnitude of thermal energy. A cable 28 operatively attached to the handle 22 electrically connects the thermal heating element 24 to the generator 26. At least one supply wire (not shown) passing along the elongated shaft 16 or through a lumen in the elongated shaft 16 from the handle 22 to the thermal heating element 24 conveys the treatment energy to the thermal heating element 24. A foot pedal 100 is electrically connected to the generator 26 to allow the operator to initiate, terminate and, optionally, adjust various operational characteristics of the generator, including, power delivery. For systems that provide for the delivery of a monopolar electric field via the thermal heating element 24, a neutral or dispersive electrode 38 can be electrically connected to the generator 26. Additionally, a sensor (not shown), such as a temperature (e.g., thermocouple, thermistor, etc.) or impedance sensor, can be located proximate to or within the thermal heating element and connected to one or more of the supply wires. With two supply wires, one wire could convey the energy to the thermal heating element and one wire could transmit the signal from the sensor. Alternatively, both wires could transmit energy to the thermal heating element.

Once proximity to, alignment with, and contact between the thermal heating element 24 and tissue are established within the respective renal artery (as FIG. 6B shows), the purposeful application of energy from the generator 26 to tissue by the thermal heating element 24 induces one or more desired thermal heating effects on localized regions of the renal artery and adjacent regions of the renal plexus (RP), which lay intimately within or adjacent to the adventitia of the renal artery. The purposeful application of the thermal heating effects can achieve neuromodulation along all or a portion of the RP.

The thermal heating effects can include both thermal ablation and non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for the ablative thermal alteration.

Further details of special size, configuration, and mechanical properties of the elongated shaft 16 and the thermal heating element 24, as well as other aspects of the system 10 will now be described. In still other embodiments, the system 10 may have a different configuration and/or include different features. For example, multi-thermal heating element devices, such as multi-electrode baskets or other balloon expandable devices may be implemented to intravascularly deliver neuromodulatory treatment with or without contact the vessel wall.

B. Size and Configuration of the Elongated Shaft for Achieving Intravascular Access to a Renal Artery As explained above, intravascular access to an interior of a renal artery can be achieved through the femoral artery. As FIG. 6B shows, the elongated shaft 16 is specially sized and configured to accommodate passage through this intravascular path 14, which leads from a percutaneous access site in the femoral artery to a targeted treatment site within a renal artery. In this way, the caregiver is able to orient the thermal heating element 24 within the renal artery for its intended purpose.

For practical purposes, the maximum outer dimension (e.g., diameter) of any section of the elongated shaft 16, including the thermal heating element 24 it carries, is dictated by the inner diameter of the guide catheter through which the elongated shaft 16 is passed. Assuming, for example, that an 8 French guide catheter (which has an inner diameter of approximately 0.091 inches) would likely be, from a clinical perspective, the largest guide catheter used to access the renal artery, and allowing for a reasonable clearance tolerance between the thermal heating element 24 and the guide catheter, the maximum outer dimension can be realistically expressed as being less than or equal to approximately 0.085 inches. However, use of a smaller 5 French guide catheter 94 may require the use of smaller outer diameters along the elongated shaft 16. For example, a thermal heating element 24 that is to be routed within a 5 French guide catheter would have an outer dimension of no greater than 0.053 inches. In another example, a thermal heating element 24 that is to be routed within a 6 French guide catheter would have an outer dimension of no great than 0.070 inches.

1. Proximal Force Transmitting Section

Figure 7A:
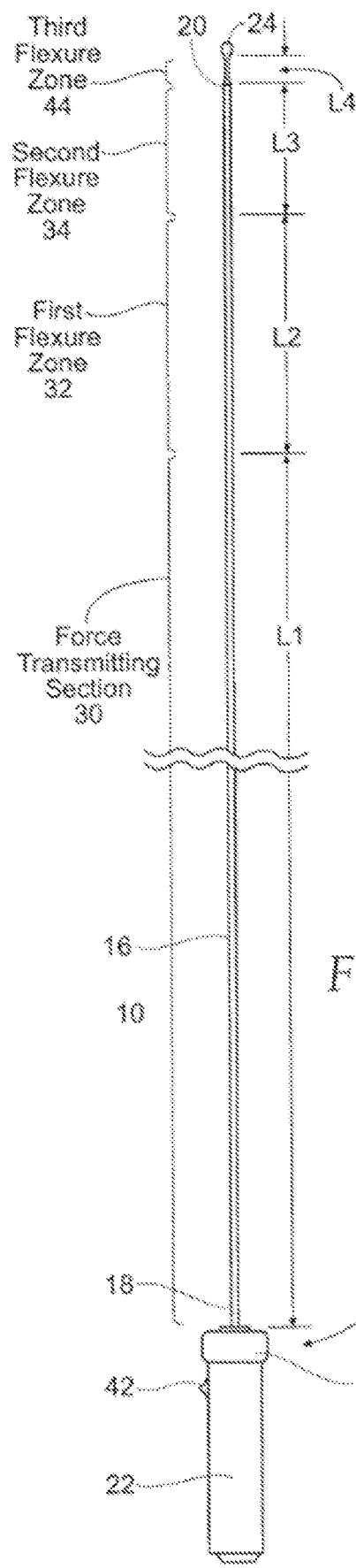
FIGS. 7A to 7D are a series of views of the elongated shaft of the treatment device shown in FIG. 5, showing the different mechanical and functional regions that the elongated shaft incorporates.

As FIG. 7A shows, the proximal end region 18 of the elongated shaft 16 includes, coupled to the handle 22, a force transmitting section 30. The force transmitting section 30 is sized and configured to possess selected mechanical properties that accommodate physical passage through and the transmission of forces within the intravascular path 14, as it leads from the accessed femoral artery (left or right), through the respective iliac branch artery and into the aorta, and in proximity to the targeted renal artery (left or right). The mechanical properties of the force transmitting section 30 include at least a preferred effective length (expressed in inches or centimeters).

As FIG. 7A shows, the force transmitting section 30 includes a preferred effective length L1. The preferred effective length L1 is a function of the anatomic distance within the intravascular path 14 between the access site and a location just proximate to the junction of the aorta and renal arteries. The preferred effective length L1 can be derived from textbooks of human anatomy, augmented by a caregiver's knowledge of the targeted site generally or as derived from prior analysis of the particular morphology of the targeted site. The preferred effective length L1 is also dependent on the length of the guide catheter that is used, if any. In a representative embodiment, for a normal human, the preferred effective length L1 comprises about 30 cm to about 110 cm. If no guide catheter is used, then the preferred effective length L1 comprises about 30 cm to about 35 cm. If a 55 cm length guide catheter is used, then the preferred effective length L1 comprises about 65 cm to about 70 cm. If a 90 cm length guide catheter is used, then the preferred effective length L1 comprises about 95 cm to about 105 cm.

The force transmitting section 30 also includes a preferred axial stiffness and a preferred torsional stiffness. The preferred axial stiffness expresses the capability of the force transmitting section 30 to be advanced or withdrawn along the length of the intravascular path 14 without buckling or substantial deformation. Since some axial deformation is necessary for the force transmitting section 30 to navigate the tortuous intravascular path 14 without providing too much resistance, the preferred axial stiffness of the force transmitting section should also provide this capability. The preferred torsional stiffness expresses the capability of the force transmitting section 30 to rotate the elongated shaft 16 about its longitudinal axis along its length without kinking or permanent deformation. As will be described in greater detail later, the ability to advance and retract, as well as rotate, the distal end region 20 of the elongated shaft 16 within the respective renal artery is desirable.

The desired magnitude of axial stiffness and rotational stiffness for the force transmitting section 30 can be obtained by selection of constituent material or materials to provide a desired elastic modulus (expressed in terms, e.g., of a Young's Modulus (E)) indicative of axial and torsional stiffnesses, as well as selecting the construct and configuration of the force transmitted section in terms of, e.g., its interior diameter, outer diameter, wall thickness, and structural features, including cross-sectional dimensions and geometry. Representative examples are described in greater detail below.

2. Proximal Flexure Zone

Figure 7B:
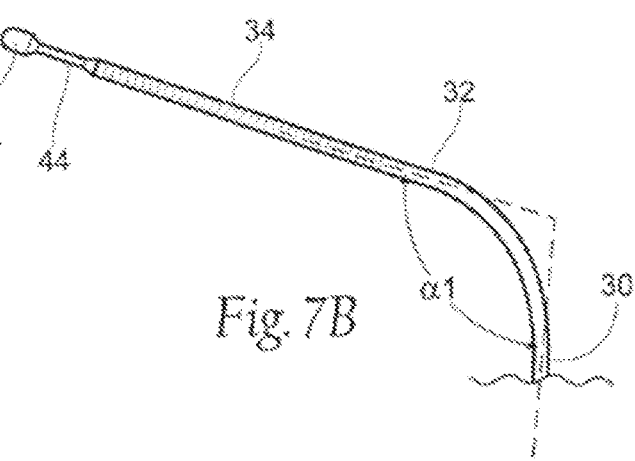

As FIGS. 7A and 7B show, the distal end region 20 of the elongated shaft 16 is coupled to the force transmitting section 30. The length L1 of the force transmitting section 30 generally serves to bring the distal end region 20 into the vicinity of the junction of the respective renal artery and aorta (as FIG. 6B shows). The axial stiffness and torsional stiffness of the force transmitting region transfer axial and rotation forces from the handle 22 to the distal end region 20, as will be described in greater detail later.

As shown in FIG. 7B, the distal end region 20 includes a first or proximal flexure zone 32 proximate to the force transmitting section 30. The proximal flexure zone 32 is sized and configured to have mechanical properties that accommodate significant flexure or bending at a prescribed preferred access angle α1 and provide for the transmission of torque during rotation, without fracture, collapse, substantial distortion, or significant twisting of the elongated shaft 16. The proximal flexure zone 32 should accommodate flexure sufficient for the distal end region 20 to advance via a guide catheter into the renal artery without substantially straightening out the guide catheter.

Angle α1 is defined by the angular deviation that the treatment device 12 must navigate to transition from the aorta (along which the force transmitting section 30 is aligned) and the targeted renal artery (along which the distal end region 20 is aligned) (this is also shown in FIG. 6B). This is the angle that the proximal flexure zone 32 must approximate to align the distal end region 20 of the elongated shaft 16 with the targeted renal artery, while the force transmitting section 30 of the elongated shaft 16 remains aligned with the native axis of the aorta (as FIG. 6B shows). The more tortuous a vessel, the greater bend the proximal flexure zone 32 will need to make for the distal end region of the treatment device to access the renal artery and the smaller the angle α1.

The proximal flexure zone 32 is sized and configured to possess mechanical properties that accommodate significant, abrupt flexure or bending at the access angle α1 near the junction of the aorta and the renal artery. Due to its size, configuration, and mechanical properties, the proximal flexure zone 32 must resolve these flexure or bending forces without fracture, collapse, distortion, or significant twisting. The resolution of these flexure or bending forces by the proximal flexure zone 32 makes it possible for the distal end region 20 of the elongated shaft 16 to gain entry along the intravascular path 14 into a targeted left or right renal artery.

The proximal flexure zone 32 is sized and configured in length L2 to be less than length L1 (see FIG. 7A). That is because the distance between the femoral access site and the junction of the aorta and renal artery (typically approximating about 40 cm to about 55 cm) is generally greater than the length of a renal artery between the aorta and the most distal treatment site along the length of the renal artery, which is typically about 4 cm to about 6 cm. The preferred effective length L2 can be derived from textbooks of human anatomy, augmented with a caregiver's knowledge of the site generally or as derived from prior analysis of the particular morphology of the targeted site.

Desirably, the length L2 is selected to make it possible to rest a portion of the proximal flexure zone 32 partially in the aorta at or near the length L1, as well as rest the remaining portion of the proximal flexure zone 32 partially within the renal artery (as FIG. 6B shows). In this way, the proximal flexure zone 32 defines a transitional bend that is supported and stable within the vasculature.

As will be described in greater detail later, and as shown in FIG. 6B, the length L2 of the proximal flexure zone 32 desirably does not extend the full length of the targeted length of the renal artery. That is because the distal end region 20 of the elongated shaft 16 desirably includes one or more additional flexure zones, distal to the proximal flexure zone 32 (toward the substance of the kidney), to accommodate other different functions important to the therapeutic objectives of the treatment device 12. As will be described later, the ability to transmit torque through the proximal flexure zone 32 makes it possible to rotate the thermal heating device to properly position the thermal heating element within the renal artery for treatment.

In terms of axial and torsional stiffness; the mechanical properties of proximal flexure zone 32 can and desirably do differ from the mechanical properties of the force transmitting section 30. This is because the proximal flexure zone 32 and the force transmitting region serve different functions while in use. Alternatively, the mechanical properties of proximal flexure zone 32 and force transmitting section 30 can be similar.

The force transmitting section 30 serves in use to transmit axial load and torque over a relatively long length (L1) within the vascular pathway. In contrast, the proximal flexure zone 32 needs to transmit axial load and torque over a lesser length L2 proximate to or within a respective renal artery. Importantly, the proximal flexure zone 32 must abruptly conform to an access angle α1 near the junction of the aorta and the respective renal artery, without fracture, collapse, substantial distortion, or significant twisting. This is a function that the force transmitting zone need not perform. Accordingly, the proximal flexure zone 32 is sized and configured to be less stiff and to possess greater flexibility than the force transmitting section 30.

The desired magnitude of axial stiffness, rotational stiffness, and flexibility for the proximal flexure zone 32 can be obtained by selection of constituent material or materials to provide a desired elastic modulus (expressed, e.g., in terms of a Young's Modulus (E)) indicative of flexibility, as well as selecting the construct and configuration of the force transmitting section, e.g., in terms of its interior diameter, outer diameter, wall thickness, and structural features, including cross-sectional dimensions and geometry. Representative examples will be described in greater detail later.

Although it is desirable that the force transmitting section 30 and the proximal flexure zone 32 have stiffness and flexibility properties that are unique to their respective functions, it is possible that the force transmitting section 30 and the proximal flexure zone 32 comprise the same materials, size and geometric configuration such that the force transmitting section 30 and the proximal flexure zone 32 constitute the same section.

3. Intermediate Flexure Zone

Figure 7C:
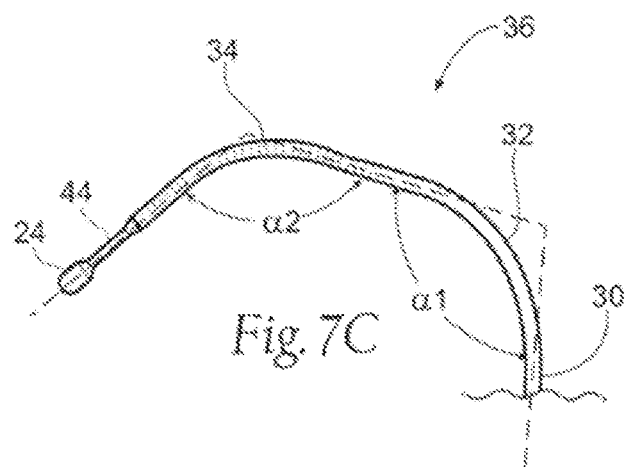

As shown in FIGS. 7A, 7B, and 7C, the distal end region 20 of the elongated shaft 16 may also include, distal to the proximal flexure zone 32, a second or intermediate flexure zone 34. The thermal heating element 24 may be supported by the intermediate flexure zone 34.

The intermediate flexure zone 34 is sized, configured, and has the mechanical properties that accommodate additional flexure or bending, independent of the proximal flexure zone 32, at a preferred contact angle α2, without fracture, collapse, substantial distortion, or significant twisting. The intermediate flexure zone 34 should also accommodate flexure sufficient for the distal end region 20 to advance via a guide catheter into the renal artery without straightening out the guide catheter.

The preferred contact angle α2 is defined by the angle through which the thermal heating element 24 can be radially deflected within the renal artery to establish contact between the thermal heating element 24 and an inner wall of the respective renal artery (as FIG. 6B shows). The size of the contact angle α2 and the intermediate flexure zone length L3 are based on the native inside diameter of the respective renal artery where the thermal heating element 24 rests, which may vary between about 2 mm and about 10 mm. It is most common for the diameter of the renal artery to vary between about 3 mm and about 7 mm.

The intermediate flexure zone 34 extends from the proximal flexure zone 32 for a length L3 into the targeted renal artery (see FIG. 6B). Desirably, the length L3 is selected, taking into account the length L2 of the proximal flexure zone 32 that extends into the renal artery, as well as the anatomy of the respective renal artery, to actively place the thermal heating element 24 (carried at the end of the distal end region 20) at or near the targeted treatment site (as FIG. 6B shows). The length L3 can be derived, taking the length L2 into account, from textbooks of human anatomy, together with a caregiver's knowledge of the site generally or as derived from prior analysis of the particular morphology of the targeted site. In a representative embodiment, L2 is about 9 cm and L3 is about 5 mm to about 15 mm. In certain embodiments, particularly for treatments in relatively long blood vessels, L3 can be as long as about 20 mm. In another representative embodiment, and as described later in greater detail, L3 is about 12.5 mm.

As FIG. 7A shows, the intermediate flexure zone 34 is desirably sized and configured in length L3 to be less than length L2. This is because, in terms of length, the distance required for actively deflecting the thermal heating element 24 into contact with a wall of the renal artery is significantly less than the distance required for bending the elongated shaft 16 to gain access from the aorta into the renal artery. Thus, the length of the renal artery is occupied in large part by the intermediate flexure zone 34 and not as much by the proximal flexure zone 32.

As FIG. 7C shows, having proximal and intermediate flexure zones 32 and 34, the distal end region 20 of the elongated shaft 16 can, in use, be placed into a complex, multi-bend structure 36. The complex, multi-bend structure 36 comprises one deflection region at the access angle α1 over a length L2 (the proximal flexure zone 32) and a second deflection region at the contact angle α2 over a length L3 (the intermediate flexure zone 34). In the complex, multi-bend, both L2 and L3 and angle α1 and angle α2 can differ. This is because the angle α1 and length L2 are specially sized and configured to gain access from an aorta into a respective renal artery through a femoral artery access point, and the angle α2 and length L3 are specially sized and configured to align a thermal heating element 24 with an interior wall inside the renal artery.

In the illustrated embodiment (see, e.g., FIG. 7C), the intermediate flexure zone 34 is sized and configured to allow a caregiver to remotely deflect the intermediate flexure zone 34 within the renal artery, to radially position the thermal heating element 24 into contact with an inner wall of the renal artery.

Figures 12A, 12B, 12C, 12D:
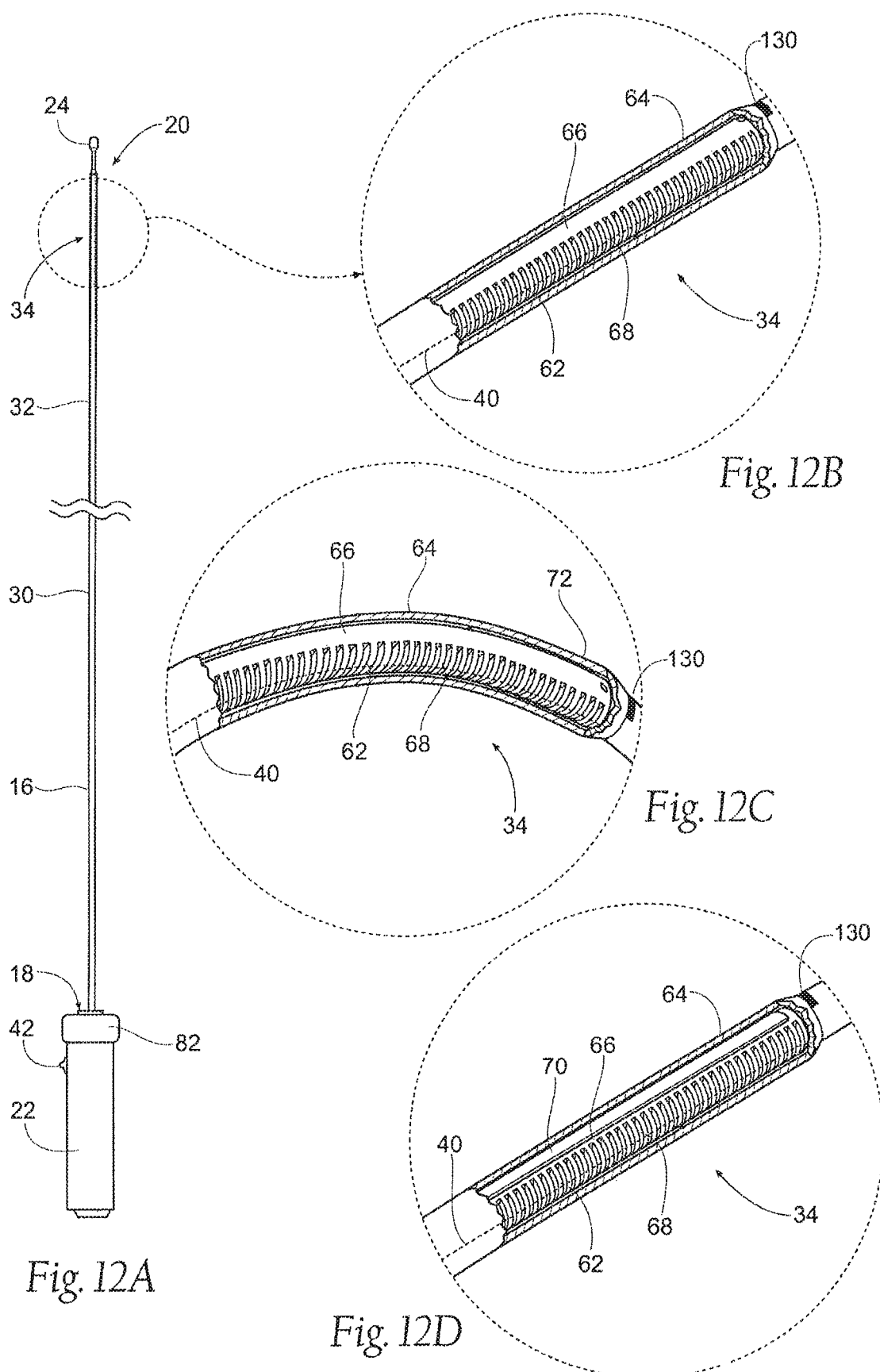
FIGS. 12A to 12D show a representative embodiment of the intermediate flexure zone of the elongated shaft of the treatment device shown in FIG. 5.

In the illustrated embodiment, a control mechanism is coupled to the intermediate flexure zone 34. The control mechanism includes a control wire 40 attached to the distal end of the intermediate flexure zone 34 (a representative embodiment is shown in FIGS. 12B and 12C and will be described in greater detail later). The control wire 40 is passed proximally through the elongated shaft 16 and coupled to an actuator 42 on the handle 22. Operation of the actuator 42 (e.g., by the caregiver pulling proximally on or pushing forward the actuator 42) pulls the control wire 40 back to apply a compressive and bending force to the intermediate flexure zone 34 (as FIGS. 7C and 120 show)

resulting in bending. The compressive force in combination with the optional directionally biased stiffness (described further below) of the intermediate flexure zone 34 deflects the intermediate flexure zone 34 and, thereby, radially moves the thermal heating element 24 toward an interior wall of the renal artery (as FIG. 6B shows).

Desirably, as will be described in greater detail later, the distal end region 20 of the elongated shaft 16 can be sized and configured to vary the stiffness of the intermediate flexure zone 34 about its circumference. The variable circumferential stiffness imparts preferential and directional bending to the intermediate flexure zone 34 (i.e., directionally biased stiffness). In response to operation of the actuator 42, the intermediate flexure zone 34 may be configured to bend in a single preferential direction. Representative embodiments exemplifying this feature will be described in greater detail later.

The compressive and bending force and resulting directional bending from the deflection of the intermediate flexure zone 34 has the consequence of altering the axial stiffness of the intermediate flexure zone. The actuation of the control wire 40 serves to increase the axial stiffness of the intermediate flexure zone.

In terms of axial and torsional stiffnesses, the mechanical properties of intermediate flexure zone 34 can and desirably do differ from the mechanical properties of the proximal flexure zone 32. This is because the proximal flexure zone 32 and the intermediate flexure zone 34 serve different functions while in use.

The proximal flexure zone 32 transmits axial load and torque over a longer length (L2) than the intermediate flexure zone 34 (L3). Importantly, the intermediate flexure zone 34 is also sized and configured to be deflected remotely within the renal artery by the caregiver. In this arrangement, less resistance to deflection is desirable. This is a function that the proximal flexure zone 32 need not perform. Accordingly, the intermediate flexure zone 34 is desirably sized and configured to be less stiff (when the control wire 40 is not actuated) and, importantly, to possess greater flexibility than the proximal flexure zone 32 in at least one plane of motion.

Still, because the intermediate flexure zone 34, being distal to the proximal flexure zone 32, precedes the proximal flexure zone 32 through the access angle access angle α1, the intermediate flexure zone 34 also includes mechanical properties that accommodate its flexure or bending at the preferred access angle α1, without fracture, collapse, substantial distortion, or significant twisting of the elongated shaft 16.

The desired magnitude of axial stiffness, rotational stiffness, and flexibility for the intermediate flexure zone 34 can be obtained by selection of constituent material or materials to provide a desired elastic modulus (expressed, e.g., in terms of a Young's Modulus (E)) indicative of flexibility, as well as by selecting the construct and configuration of the intermediate flexure zone 34, e.g., in terms of its interior diameter, outer diameter, wall thickness, and structural features, including cross-sectional dimensions and geometry. Representative examples will be described in greater detail later. Axial stiffness, torsional stiffness, and flexibility are properties that can be measured and characterized in conventional ways.

As before described, both the proximal and intermediate flexure zones 32 and 34 desirably include the mechanical properties of axial stiffness sufficient to transmit to the thermal heating element 24 an axial locating force. By pulling back on the handle 22, axial forces are transmitted by the force transmitting section 30 and the proximal and intermediate flexure zones 32 and 34 to retract the thermal heating element 24 in a proximal direction (away from the kidney) within the renal artery. Likewise, by pushing forward on the handle 22, axial forces are transmitted by the force transmitting section 30 and the proximal and intermediate flexure zones 32 and 34 to advance the thermal heating element 24 in a distal direction (toward the kidney) within the renal artery. Thus, proximal retraction of the distal end region 20 and thermal heating element 24 within the renal artery can be accomplished by the caregiver by manipulating the handle 22 or shaft from outside the intravascular path 14.

As before described, both the proximal and intermediate flexure zones 32 and 34 also desirably include torsional strength properties that will allow the transmission of sufficient rotational torque to rotate the distal end region 20 of the treatment device 12 such that the thermal heating element 24 is alongside the circumference of the blood vessel wall when the intermediate flexure zone 34 is deflected. By pulling or pushing on the actuator to deflect the thermal heating element 24 such that it achieves vessel wall contact, and then rotating the force transmitting section 30 and, with it, the first and intermediate flexure zones 32 and 34, the thermal heating element 24 can be rotated in a circumferential path within the renal artery. As described later, this rotating feature enables the clinical operator to maintain vessel wall contact as the thermal heating element 24 is being relocated to another treatment site. By maintaining wall contact in between treatments, the clinical operator is able to achieve wall contact in subsequent treatments with higher certainty in orientations with poor visualization.

4. Distal Flexure Zone

As FIGS. 7A, 7B, 7C, and 70, the distal end region 20 of the elongated shaft 16 can also include, distal to the intermediate flexure zone 34, a third or distal flexure zone 44. In this arrangement, the length L3 of the intermediate flexure zone 34 may be shortened by a length L4, which comprises the length of the distal flexure zone 44. In this arrangement, the thermal heating element 24 is carried at the end of the distal flexure zone 44. In effect the distal flexure zone 44 buttresses the thermal heating element 24 at the distal end of distal end region 20.

Figure 7D:
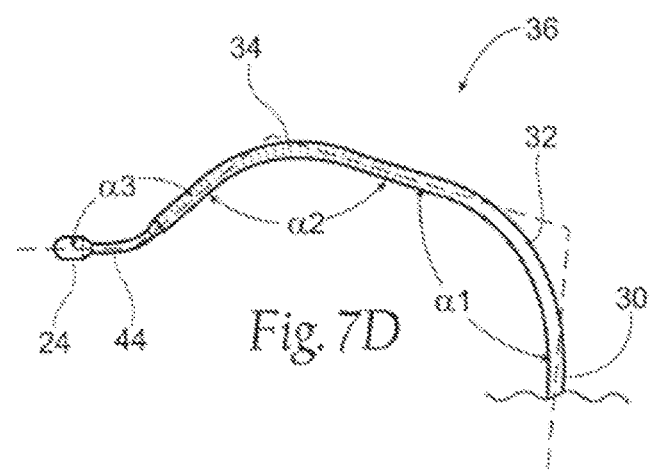

As FIG. 7D shows, the distal flexure zone 44 is sized, configured, and has the mechanical properties that accommodate additional flexure or bending, independent of the proximal flexure zone 32 and the intermediate flexure zone 34, at a preferred treatment angle α3. The distal flexure zone 44 should also accommodate flexure sufficient for the distal end region 20 to advance via a guide catheter into the renal artery without straightening out the guide catheter or causing injury to the blood vessel. The treatment angle α3 provides for significant flexure about the axis of the distal end region 20 (a representative embodiment is shown in FIG. 15C). Not under the direct control of the physician, flexure at the distal flexure zone occurs in response to contact between the thermal heating element 24 and wall tissue occasioned by the radial deflection of the thermal heating element 24 at the intermediate flexure zone 34 (see FIG. 6B). Passive deflection of the distal flexure zone provides the clinical operator with visual feedback via fluoroscopy or other angiographic guidance of vessel wall contact. Additionally, the distal flexure zone desirably orients the region of tissue contact along a side of the thermal heating element 24, thereby increasing the area of contact. The distal flexure zone 44 also biases the thermal heating element 24 against tissue, thereby stabilizing the thermal heating element 24.

The function of the distal flexure zone 44 provides additional benefits to the therapy. As actuation of the control wire 40 increases the axial stiffness of the intermediate flexure zone 34, the distal flexure zone effectively reduces the contact force between the thermal heating element 24 and the vessel wall. By relieving or reducing this contact force, the distal flexure zone minimizes the chance of mechanical injury to the vessel wall and avoids excessive contact between the thermal heating element and vessel wall (see discussion of active surface area).

As FIG. 7A shows, the distal flexure zone 44 is desirably sized and configured in length L4 to be less than length L3. This is because, in terms of length, the distance required for orienting and stabilizing the thermal heating element 24 in contact with a wall of the renal artery is significantly less than the distance required for radially deflecting the thermal heating element 24 within the renal artery. In some embodiments, length L4 can be as long as about 1 cm. In other embodiments, the length L4 is from about 2 mm to about 5 mm. In a preferred embodiment, the length L4 is about 5 mm. In other embodiments, the length L4 is about 2 mm.

The mechanical properties of distal flexure zone 44 and the intermediate flexure zone 34 in terms of axial stiffness, torsional stiffness, and flexibility can be comparable. However, the distal flexure zone 44 can be sized and configured to be less stiff and, importantly, to possess greater flexibility than the intermediate flexure zone 34.

In the embodiment just described (and as shown in FIG. 7D), the distal end region 20 may comprise a proximal flexure zone 32, a intermediate flexure zone 34, and a distal flexure zone 44. The proximal, intermediate and distal flexure zones function independent from each other, so that the distal end region 20 of the elongated shaft 16 can, in use, be placed into a more compound, complex, multi-bend structure 36. The compound, complex, multi-bend structure 36 comprises a proximal deflection region at the access angle $\alpha 1$ over a length L2 (the proximal flexure zone 32); an intermediate deflection region at the contact angle $\alpha 2$ over a length L3 (the intermediate flexure zone 34); and a distal deflection region at the treatment angle $\alpha 3$ over a length L4 (the distal flexure zone 44). In the compound, complex, multi-bend structure 36, all lengths L2, L3, and L3 and all angles $\alpha 1$, $\alpha 2$, and $\alpha 3$ can differ. This is because the angle $\alpha 1$ and length L2 are specially sized and configured to gain access from an aorta into a respective renal artery through a femoral artery access point; the angle $\alpha 2$ and length L3 are specially sized and configured to align a thermal heating element 24 element with an interior wall inside the renal artery; and the angle $\alpha 3$ and length L4 are specially sized and configured to optimize surface contact between tissue and the thermal heating element/heat transfer element.

C. Size and Configuration of the Thermal Heating Element for Achieving Neuromodulation in a Renal Artery As described in co-pending patent application Ser. No. 11/599,890 filed Nov. 14, 2006, which is incorporated herein by reference in its entirety, it is desirable to create multiple focal lesions that are circumferentially spaced along the longitudinal axis of the renal artery. This treatment approach avoids the creation of a full-circle lesion, thereby mitigating and reducing the risk of vessel stenosis, while still providing the opportunity to circumferentially treat the renal plexus, which is distributed about the renal artery. It is desirable for each lesion to cover at least 10% of the vessel circumference to increase the probability of affecting the renal plexus. However, it is important that each lesion not be too large (e.g., >60% of vessel circumference) lest the risk of a stenotic effect increases (or other undesirable healing responses such as thrombus formation or collateral damage).

It is also important that each lesion be sufficiently deep to penetrate into and beyond the adventitia to thereby affect the renal plexus.

Figure 8A:
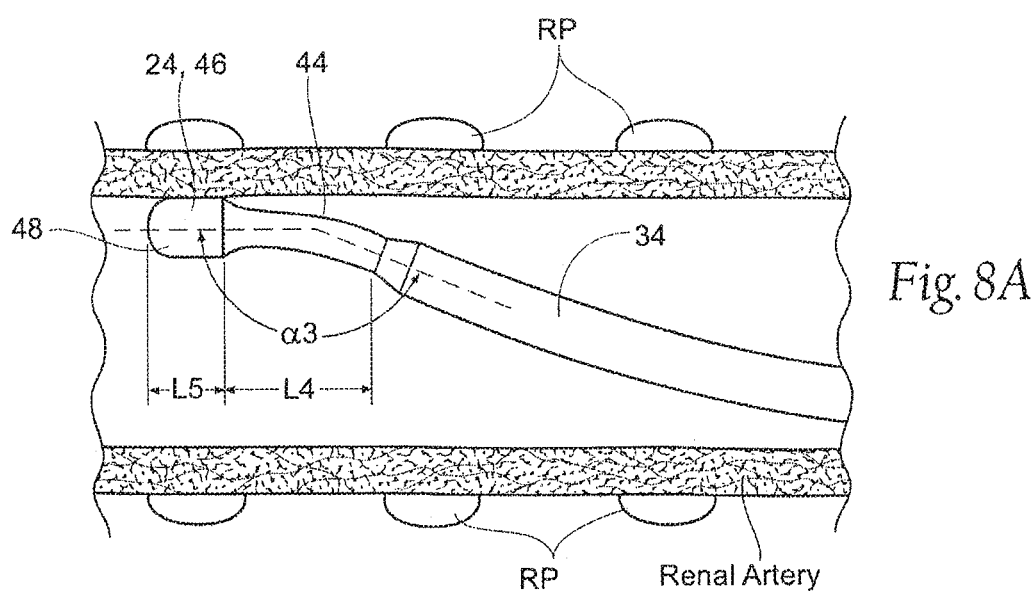
FIG. 8A to 8C show the placement of a thermal heating element, which is carried at the distal end of the elongated shaft of the treatment device shown in FIG. 5, into contact with tissue along a renal artery.

As described (and as FIG. 8A shows), the thermal heating element 24 is sized and configured, in use, to contact an internal wall of the renal artery. In the illustrated embodiment (see FIG. 8A), the thermal heating element 24 takes the form of an electrode 46 sized and configured to apply an electrical field comprising radiofrequency (RF) energy from the generator 26 to a vessel wall. In the illustrated embodiment, the electrode 46 is operated in a monopolar or unipolar mode. In this arrangement, a return path for the applied RF electric field is established, e.g., by an external dispersive electrode (not shown), also called an indifferent electrode or neutral electrode. The monopolar application of RF electric field energy serves to ohmically or resistively heat tissue in the vicinity of the electrode 46. The application of the RF electrical field thermally injures tissue. The treatment objective is to thermally induce neuromodulation (e.g., necrosis, thermal alteration or ablation) in the targeted neural fibers. The thermal injury forms a lesion in the vessel wall, which is shown, e.g., in FIG. 9B.

The active surface area of contact (ASA) between the thermal heating element 24 or electrode 46 and the vessel wall has great bearing on the efficiency and control of the transfer of a thermal energy field across the vessel wall to thermally affect targeted neural fibers in the renal plexus (RP). The active surface area of the thermal heating element 24 and electrode 46 is defined as the energy transmitting area of the element 24 or electrode 46 that can be placed in intimate contact against tissue. Too much contact between the thermal heating element and the vessel wall may create unduly high temperatures at or around the interface between the tissue and the thermal heating element, thereby creating excessive heat generation at this interface. This excessive heat can create a lesion that is circumferentially too large. This can also lead to undesirable thermal damage at the vessel wall. In addition to potentially causing stenotic injury, this undesirable thermal damage can cause tissue desiccation dehydration) which reduces the thermal conductivity of the tissue, thereby potentially creating a lesion that is too shallow to reach the neural fibers. Too little contact between the thermal heating element and the vessel wall may result in superficial heating of the vessel wall, thereby creating a lesion that is too small (e.g., <10% of vessel circumference) and/or too shallow.

While the active surface area (ASA) of the thermal heating element 24 and electrode 46 is important to creating lesions of desirable size and depth, the ratio between the active surface area (ASA) and total surface area (TSA) of the thermal heating element 24 and electrode 46 is also important. The ASA to TSA ratio influences lesion formation in two ways: (1) the degree of resistive heating via the electric field, and (2) the effects of blood flow or other convective cooling elements such as injected saline. As discussed above, the RF electric field causes lesion formation via resistive heating of tissue exposed to the electric field. The higher the ASA to TSA ratio (i.e., the greater the contact between the electrode and tissue), the greater the resistive heating. As discussed in greater detail below, the flow of blood over the exposed portion of the electrode (TSA-ASA) provides conductive and convective cooling of the electrode, thereby carrying excess thermal energy away from the interface between the vessel wall and electrode. If the ratio of ASA to TSA is too high (e.g., 50%), resistive heating of the tissue can be too aggressive and not enough excess thermal energy is being carried away, resulting in excessive heat generation and increased potential for stenotic injury, thrombus formation and undesirable lesion size. If the ratio of ASA to TSA is too low (e.g., 10%), then there is too little resistive heating of tissue, thereby resulting in superficial heating and smaller and shallower lesions.

Various size constraints for the thermal heating element 24 may be imposed for clinical reasons by the maximum desired dimensions of the guide catheter as well as by the size and anatomy of the renal artery itself. Typically, the maximum outer diameter (or cross-sectional dimension for non-circular cross-section) of the electrode 46 comprises the largest diameter encountered along the length of the elongated shaft 16 distal to the handle 22. Thus, the outer diameters of the force transmitting section 30 and proximal, intermediate and distal flexure zones 32, 34, and 44 are equal to or (desirably) less than the maximum outer diameter of the electrode 46.

In a representative embodiment shown in FIG. 8A, the electrode 46 takes the form of a right circular cylinder, possessing a length L5 that is greater than its diameter. The electrode 46 further desirably includes a distal region that is rounded to form an atraumatic end surface 48. In the representative embodiment shown in FIG. 8B, the electrode 46 is spherical in shape. The spherical shape, too, presents an atraumatic surface to the tissue interface.

Figure 8B:
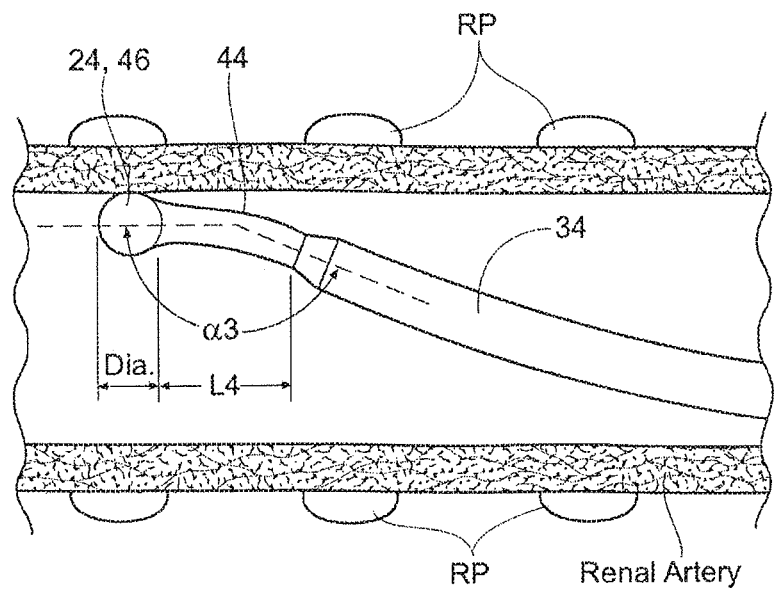
Figure 8C:
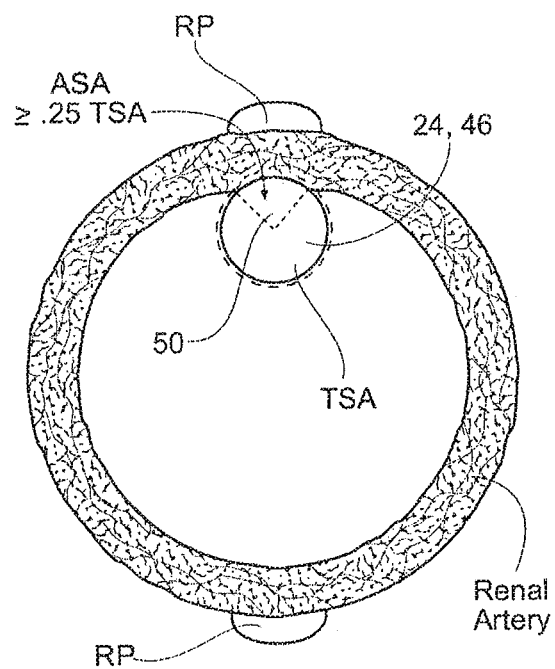

As shown in FIGS. 8A and 8B, the angle α3 and length L4 of the distal flexure zone 44 are specially sized and configured, given the TSA of the respective electrode, to optimize an active surface area of contact between tissue and the respective electrode 46 (ASA). The angle α3 and the length L4 of the distal flexure zone 44 make it possible to desirably lay at least a side quadrant 50 of the electrode 46 against tissue (see FIG. 8C). The active surface area of the electrode 46 contacting tissue (ASA) can therefore be expressed ASA≥0.25 TSA and ASA≤0.50 TSA.

The above ASA-TSA relationship applies to the power delivery algorithm described in co-pending patent application Ser. No. 12/147,154, filed Jun. 26, 2008, which is incorporated herein by reference in its entirety. An ASA to TSA ratio of over 50% may be effective with a reduced power delivery profile. Alternatively, a higher ASA to TSA ratio can be compensated for by increasing the convective cooling of the electrode that is exposed to blood flow. As discussed further below, this could be achieved by injecting cooling fluids such as chilled saline over the electrode and into the blood stream.

The stiffnesses of each of the intermediate and distal flexure zones 34 and 44 are also selected to apply via the electrode a stabilizing force that positions the electrode 46 in substantially secure contact with the vessel wall tissue. This stabilizing force also influences the amount of wall contact achieved by the thermal heating element (i.e., the ASA to TSA ratio). With greater stabilizing force, the thermal heating element has more wall contact and with less stabilizing force, less wall contact is achieved. Additional advantages of the stabilizing force include, (1) softening the contact force between the distal end 20 and vessel wall to minimize risk of mechanical injury to vessel wall, (2) consistent positioning of the electrode 46 flat against the vessel wall, and (3) stabilizing the electrode 46 against the vessel wall. The stabilizing force also allows the electrode to return to a neutral position after the electrode is removed from contact with the wall.

As previously discussed, for clinical reasons, the maximum outer diameter (or cross-sectional dimension) of the electrode 46 is constrained by the maximum inner diameter of the guide catheter through which the elongated shaft 16 is to be passed through the intravascular path 14. Assuming that an 8 French guide catheter 94 (which has an inner diameter of approximately 0.091 inches) is, from a clinical perspective, the largest desired catheter to be used to access the renal artery, and allowing for a reasonable clearance tolerances between the electrode 46 and the guide catheter, the maximum diameter of the electrode 46 is constrained to about 0.085 inches. In the event a 6 French guide catheter is used instead of an 8 French guide catheter, then the maximum diameter of the electrode 46 is constrained to about 0.070 inches. In the event a 5 French guide catheter is used, then maximum diameter of the electrode 46 is constrained to about 0.053 inches. Based upon these constraints and the aforementioned power delivery considerations, the electrode 46 desirably has an outer diameter of from about 0.049 to about 0.051 inches.

While it may be possible to provide a catheter apparatus or device having multiple electrodes at or proximate to the distal end of the apparatus, it is desirable for the catheter apparatus described herein to have only a single electrode at or proximate to the distal end. There are several reasons why a single electrode apparatus may have clinical and/or functional benefits over a multiple electrode apparatus. For example, as indicated below, an electrode with a relatively large surface area may create larger, more effective lesions via increased energy delivery and higher power since blood flow carries away excess heat and effectively cools the electrode. As discussed above, the maximum diameter/crossing profile of the electrode is constrained by the inner diameter of the guide catheter through which the electrode is delivered. It would be difficult for a multiple electrode apparatus to have electrodes that are as large as a single electrode at the distal end of the apparatus since the crossing profile of the multiple electrodes would have to take into account the diameter of the apparatus shaft. Attempts to design an apparatus having multiple electrodes that individually approach the surface area of a single electrode at the distal end are expected to increase complexity and cost. Additionally, multiple electrode arrangements can also increase stiffness of the apparatus, which may not only compromise the deliverability of the apparatus, but also increase risk of injury to the blood vessels. For example, a catheter apparatus that is too stiff would not be able to make the significant bend that is necessary to access a renal artery from the abdominal aorta.

Not only may delivery to and through a tortuous blood vessel, such as a renal artery, be difficult with a multiple electrode apparatus, but placement and use within a tortuous blood vessel may also be challenging. Since vascular anatomy may vary significantly because of tortuosity and the unpredictable location of vessel branches and vessel disease (e.g., atherosclerosis) successful delivery and placement of an apparatus can be very complicated with multiple electrodes. Additionally, it would be very difficult to ensure proper wall contact for all electrodes due to the variable anatomy of the vessel where treatment is to be administered. Although sensors and software could be developed and implemented to address some of these issues, it would increase the cost of the system and increase complexity for the user. Hence, a single electrode apparatus such as that described herein may be more effective than a multiple electrode apparatus, particularly in tortuous blood vessels where there is a high degree of anatomic variability.

D. Applying Energy to Tissue Via the Thermal Heating Element

Referring back to FIG. 5, in the illustrated embodiment, the generator 26 may supply to the electrode 46 a pulsed or continuous RF electric field. Although a continuous delivery of RF energy is desirable, the application of thermal energy in pulses may allow the application of relatively higher energy levels (e.g., higher power), longer or shorter total duration times, and/or better controlled intravascular renal neuromodulation therapy. Pulsed energy may also allow for the use of a smaller electrode.

The thermal therapy may be monitored and controlled, for example, via data collected with thermocouples, impedance sensors, pressure sensors, optical sensors or other sensors 52 (see FIG. 9A), which may be incorporated into or on electrode 46 or in/on adjacent areas on the distal end region 20. Additionally or alternatively, various microsensors can be used to acquire data corresponding to the thermal heating element, the vessel wall and/or the blood flowing across the thermal heating element. For example, arrays of micro thermocouples and/or impedance sensors can be implemented to acquire data along the thermal heating element or other parts of the treatment device. Sensor data can be acquired or monitored prior to, simultaneous with, or after the delivery of energy or in between pulses of energy, when applicable. The monitored data may be used in a feedback loop to better control therapy, e.g., to determine whether to continue or stop treatment, and it may facilitate controlled delivery of an increased or reduced power or a longer or shorter duration therapy.

Figure 9A:
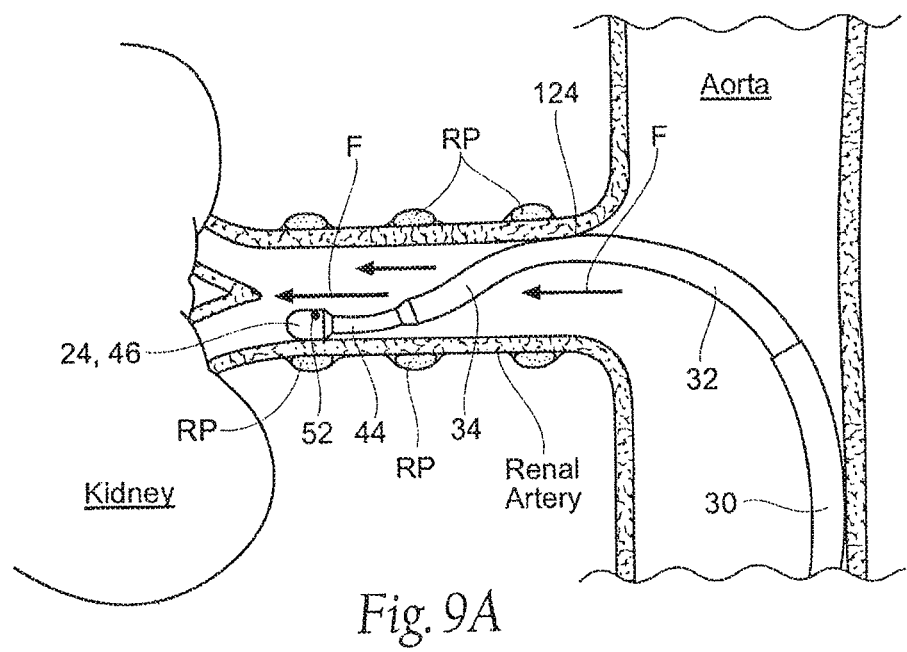
FIGS. 9A and 9B show placement of the thermal heating element shown in FIGS. 8A to 8C into contact with tissue along a renal artery and delivery of thermal treatment to the renal plexus.
Figure 9B:
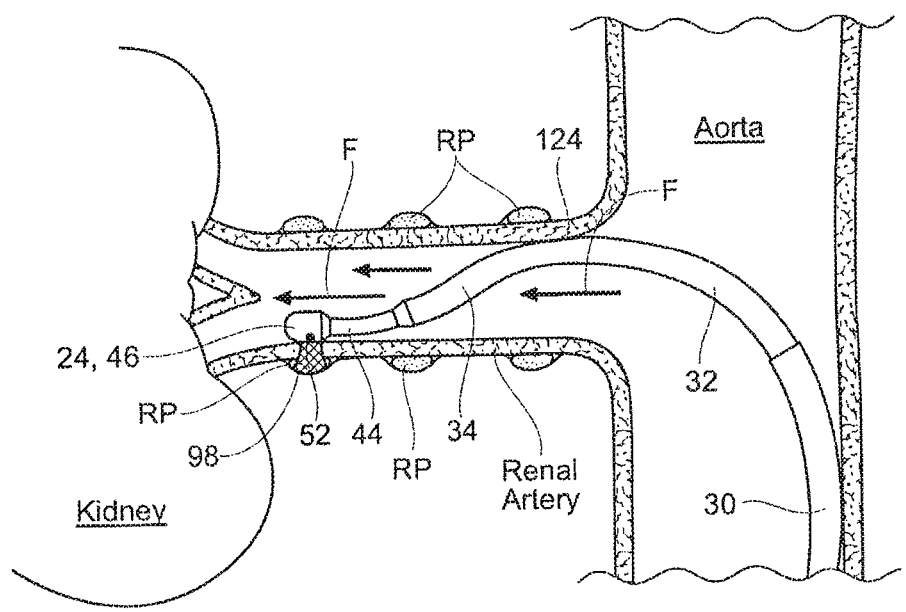

Non-target tissue may be protected by blood flow (F) within the respective renal artery as a conductive and/or convective heat sink that carries away excess thermal energy. For example (as FIGS. 9A and 9B show), since blood flow (F) is not blocked by the elongated shaft 16 and the electrode 46 it carries, the native circulation of blood in the respective renal artery serves to remove excess thermal energy from the non-target tissue and the thermal heating element. The removal of excess thermal energy by blood flow also allows for treatments of higher power, where more energy can be delivered to the target tissue as thermal energy is carried away from the electrode and non-target tissue. In this way, intravascularly-delivered thermal energy heats target neural fibers located proximate to the vessel wall to modulate the target neural fibers, while blood flow (F) within the respective renal artery protects non-target tissue of the vessel wall from excessive or undesirable thermal injury. When energy is delivered in pulses, the time interval between delivery of thermal energy pulses may facilitate additional convective or other cooling of the non-target tissue of the vessel wall compared to applying an equivalent magnitude or duration of continuous thermal energy.

In addition, or as an alternative, to utilizing blood flow (F) as a heat sink, a thermal fluid may be injected, infused, or otherwise delivered into the vessel to remove excess thermal energy and protect the non-target tissues. The thermal fluid may, for example, comprise a saline or other biocompatible fluid. The thermal fluid may, for example, be injected through the treatment device 12 via an infusion lumen and/or port (not shown) or through a guide catheter at a location upstream from an energy delivery element, or at other locations relative to the tissue for which protection is sought. The use of a thermal fluid may allow for the delivery of increased/higher power, smaller electrode size and/or reduced treatment time.

Although many of the embodiments described herein pertain to electrical systems configured for the delivery of RF energy, it is contemplated that the desired treatment can be can be accomplished by other means, e.g., by coherent or incoherent light; heated or cooled fluid; microwave; ultrasound (including high intensity focused ultrasound); diode laser; a tissue heating fluid; or cryogenic fluid.

III. Representative Embodiments

A. First Representative Embodiment (Proximal, Intermediate, and Distal Flexure Zones with Distally Carried Thermal Heating Element 24)

FIGS. 10A to 15H show a representative embodiment of an elongated shaft 16 that includes a proximal force transmitting section 30, as well as proximal, intermediate and distal flexure zones 32, 34, and 44, having the physical and mechanical features described above. In this embodiment, the thermal heating element 24 is carried distally of the distal flexure zone 44 (see, e.g., FIG. 11A).

1. Force Transmitting Section

Figures 10A, 10B:
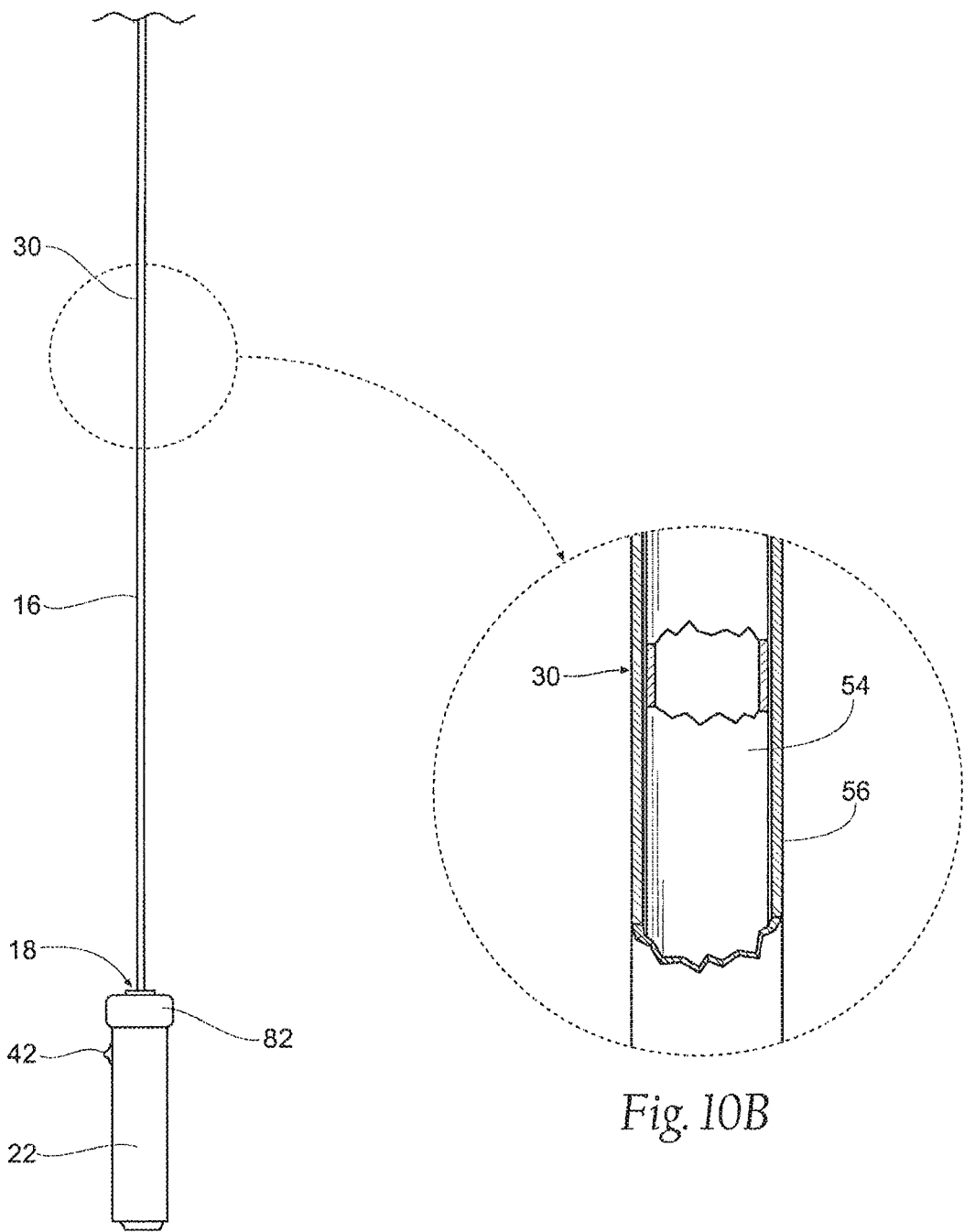
FIGS. 10A and 10B show a representative embodiment of the force transmitting section of the elongated shaft of the treatment device shown in FIG. 5.

In the illustrated embodiment, as shown in FIGS. 10A and 10B, the proximal force transmitting section 30 comprises a first elongated and desirably tubular structure, which can take the form of, e.g., a first tubular structure 54. The first tubular structure 54 is desirably a hypo tube that is made of a metal material, e.g. of stainless steel, or a shape memory alloy, e.g., nickel titanium (a.k.a., nitinol or NiTi), to possess the requisite axial stiffness and torsional stiffness, as already described, for the force transmitting section 30. As already described, the force transmitting section 30 comprises the most stiff section along the elongated shaft 16, to facilitate axially movement of the elongated shaft 16, as well as rotational manipulation of the elongated shaft 16 within the intravascular path 14. Alternatively, the first tubular structure 54 may comprise a hollow coil, hollow cable, solid cable (w/embedded wires), braided shaft, etc.

The stiffness is a function of material selection as well as structural features such as interior diameter, outside diameter, wall thickness, geometry and other features that are made by micro-engineering, machining, cutting and/or skiving the hypo tube material to provide the desired axial and torsional stiffness characteristics. For example, the elongated shaft can be a hypo tube that is laser cut to various shapes and cross-sectional geometries to achieve the desired functional properties.

When the first tubular structure 54 is made from an electrically conductive metal material, the first tubular structure 54 includes a sheath 56 or covering made from an electrically insulating polymer material or materials, which is placed over the outer diameter of the underlying tubular structure. The polymer material can also be selected to possess a desired durometer (expressing a degree of stiffness or lack thereof) to contribute to the desired overall stiffness of the first tubular structure 54. Candidate materials for the polymer material include polyethylene terephthalate (PET); Pebax® material; nylon; polyurethane, Grilamid® material or combinations thereof. The polymer material can be laminated, dip-coated, spray-coated, or otherwise deposited/attached to the outer diameter of the tube.

2. Proximal Flexure Zone

Figures 11A, 11B, 11C:
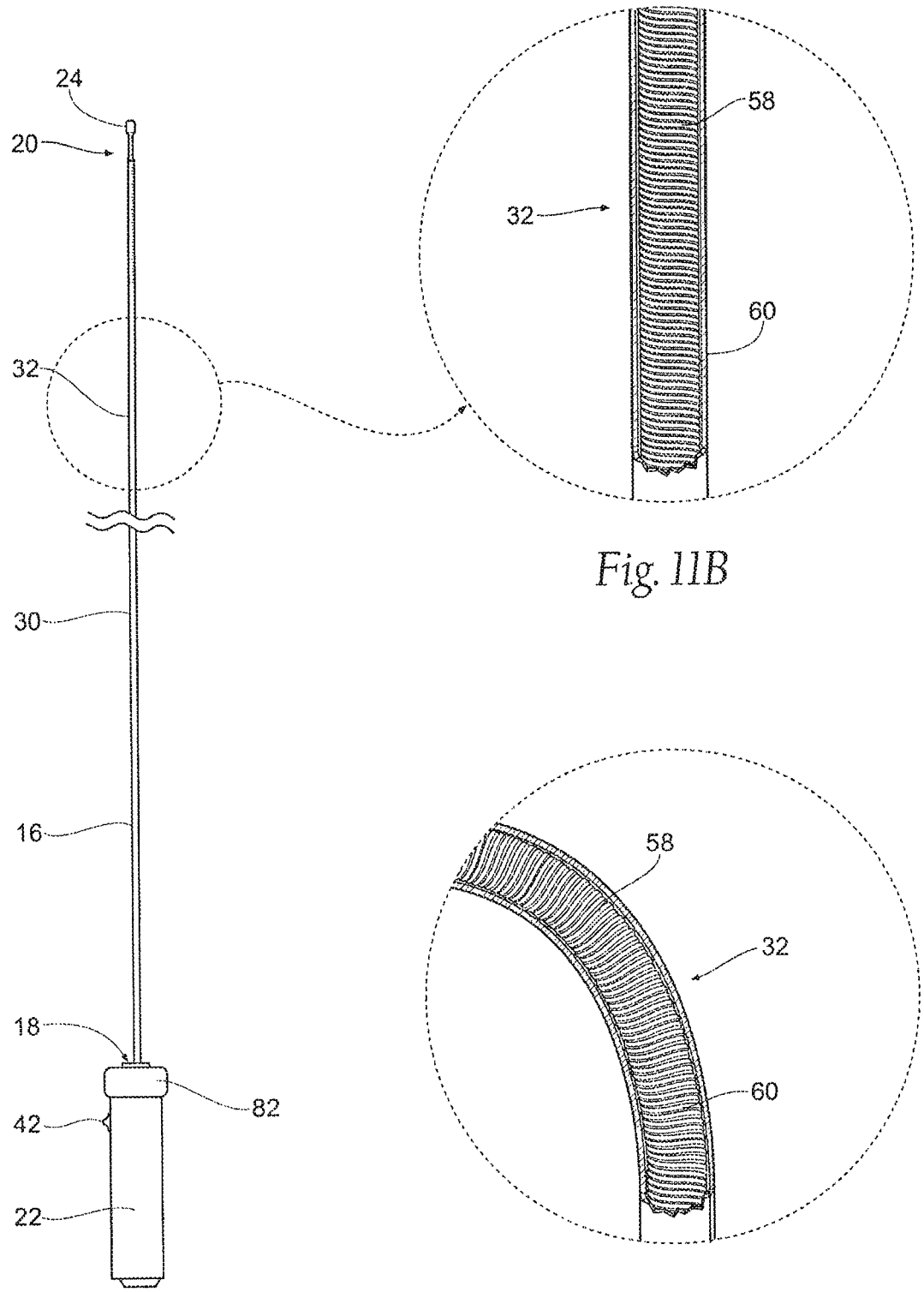
FIGS. 11A to 11C show a representative embodiment of the proximal flexure zone of the elongated shaft of the treatment device shown in FIG. 5.

As FIGS. 11A, 11B, and 11C show, the proximal flexure zone 32 comprises a second elongated and desirably tubular structure, which can take the form of, e.g., a second tubular structure 58. The second tubular structure 58 can be made from the same or different material as the first tubular structure 54. The axial stiffness and torsional stiffness of the second tubular structure 58 possesses the requisite axial stiffness and torsional stiffness, as already described, for the proximal flexure zone 32. As already described, the proximal flexure zone 32 may be less stiff and more flexible than the force transmitting section 30, to navigate the severe bend at and prior to the junction of the aorta and respective renal artery. The second tubular structure is desirably a hypo tube, but can alternatively comprise a hollow coil, hollow cable, braided shaft, etc.

It may be desirable for the first and second tubular structures 54 and 58 to share the same material. In this event, the form and physical features of the second tubular structure 58 may be altered, compared to the first tubular structure 54, to achieve the desired stiffness and flexibility differences. For example, the interior diameter, outside diameter, wall thickness, and other engineered features of the second tubular structure 58 can be tailored to provide the desired axial and torsional stiffness and flexibility characteristics. For example, the second tubular structure 58 can be laser cut along its length to provide a bendable, spring-like structure. Depending on the ease of manufacturability the first and second tubular structures may be produced from the same piece of material or from two separate pieces. In the event the first tubular structure and second tubular structure are not of the same material, the outside diameter of the second tubular structure 58 can be less than the outer diameter of first tubular structure 54 (or have a smaller wall thickness) to create the desired differentiation in stiffness between the first and second tubular structures 54 and 58.

When the second tubular structure 58 is made from an electrically conductive metal material, the second tubular structure 58, like the first tubular structure 54, includes a sheath 60 (see FIGS. 11B and 11C) or covering made from an electrically insulating polymer material or materials, as already described. The sheath 60 or covering can also be selected to possess a desired durometer to contribute to the desired differentiation in stiffness and flexibility between the first and second tubular structures 58.

The second tubular structure 58 can comprise a different material than the first tubular structure 54 to impart the desired differentiation in stiffness and flexibility between the first and second tubular structures 58. For example, the second tubular structure 58 can comprise a cobalt-chromium-nickel alloy, instead of stainless steel. Alternatively, the second tubular structure 58 can comprise a less rigid polymer, braid-reinforced shaft, nitinol or hollow cable-like structure. In addition to material selection, the desired differentiation in stiffness and overall flexibility can be achieved by selection of the interior diameter, outside diameter, wall thickness, and other engineered features of the second tubular structure 58, as already described. Further, a sheath 60 or covering made from an electrically insulating polymer material, as above described, can also be placed over the outer diameter of the second tubular structure 58 to impart the desired differentiation between the first and second tubular structures 54 and 58.

3. Intermediate Flexure Zone

As FIGS. 12A, 12B, 12C, and 12D show, the intermediate flexure zone 34 comprises a third elongated and desirably tubular structure, which can take the form of, e.g., a third tubular structure 62. The third tubular structure 62 can be made from the same or different material as the first and/or second tubular structures 54 and 58. The axial stiffness and torsional stiffness of the third tubular structure 62 possesses the requisite axial stiffness and torsional stiffness, as already described, for the intermediate flexure zone 34. As already described, the intermediate flexure zone 34 may be less stiff and more flexible than the proximal flexure zone 32, to facilitate controlled deflection of the intermediate flexure zone 34 within the respective renal artery.

If the second and third tubular structures 58 and 62 share the same material, the form and physical features of the third tubular structure 62 are altered, compared to the second tubular structure 58, to achieve the desired stiffness and flexibility differences. For example, the interior diameter, outside diameter, wall thickness, and other engineered features of the third tubular structure 62 can be tailored to provide the desired axial and torsional stiffness and flexibility characteristics. For example, the third tubular structure 62 can be laser cut along its length to provide a more bendable, more spring-like structure than the second tubular structure 58.

When the third tubular structure 62 is made from an electrically conductive metal material, the third tubular structure 62 also includes a sheath 64 (see FIGS. 12B, 12C, and 12D) or covering made from an electrically insulating polymer material or materials, as already descried. The sheath 64 or covering can also be selected to possess a desired durometer to contribute to the desired differentiation in stiffness and flexibility between the second and third tubular structure 62s.

The third tubular structure 62 can comprise a different material than the second tubular structure to impart the desired differentiation in stiffness and flexibility between the second and third tubular structures 62. For example, the third tubular structure 62 can include a Nitinol material, to impart the desired differentiation in stiffness between the second and third tubular structures 58 and 62. In addition to material selection, the desired differentiation in stiffness and overall flexibility can be achieved by selection of the interior diameter, outside diameter, wall thickness, and other engineered features of the third tubular structure 62, as already described.

For example, in diameter, the outside diameter of the third tubular structure 62 is desirably less than the outer diameter of second tubular structure 58. Reduction of outside diameter or wall thickness influences the desired differentiation in stiffness between the second and third tubular structures 58 and 62.

As discussed in greater detail above, preferential deflection of the intermediate flexure zone is desirable. This can be achieved by making the third tubular structure 62 less stiff in the desired direction of deflection and/or more stiff opposite the direction of deflection. For example, as shown in FIGS. 12B and 12C, the third tubular structure 62 (unlike the second tubular structure 58) can include a laser-cut pattern that includes a spine 66 with connecting ribs 68. The pattern biases the deflection of the third tubular structure 62, in response to pulling on the control wire 40 coupled to the distal end of the third tubular structure 62, toward a desired direction. The control wire 40 is attached to a distal end of the intermediate flexure zone with solder 130. The benefits of preferential deflection within a renal artery have already been described.

As also shown in FIG. 12D, a flat ribbon material 70 (e.g., Nitinol, stainless steel, or spring stainless steel) can be attached to the third tubular structure 62. When the pulling force is removed from the control wire 40, the flat ribbon, which serves to reinforce the deflectable third tubular structure 62, will straighten out the deflectable third tubular structure 62.

Further, a sheath 72 (see FIGS. 12B, 120, and 12D) or covering made from an electrically insulating polymer material, as above described, and having a desired durometer can also be placed over the outer diameter of the second tubular structure 58 to impart the desired differentiation between the first and second tubular structures 54 and 58.

Preferential deflection from reduced stiffness in the direction of deflection, as described above, can be achieved in a number of additional ways. For example, as FIGS. 13B and 13C show, the third tubular structure 62 can comprise a tubular polymer or metal/polymer composite having segments with different stiffnesses D1 and D2, in which D1>D2 (that is, the segment with D1 is mechanically stiffer than the segment with D2. The third tubular structure 62 can also take the form of an oval, or rectangular, or flattened metal coil or polymer having segments with different stiffnesses D1 and D2, in which D1>D2 (as shown in FIG. 13C). In either arrangement, the segment having the lower stiffness D2 is oriented on the third tubular structure 62 on the same side as the actuator wire is attached.

Figure 14A:
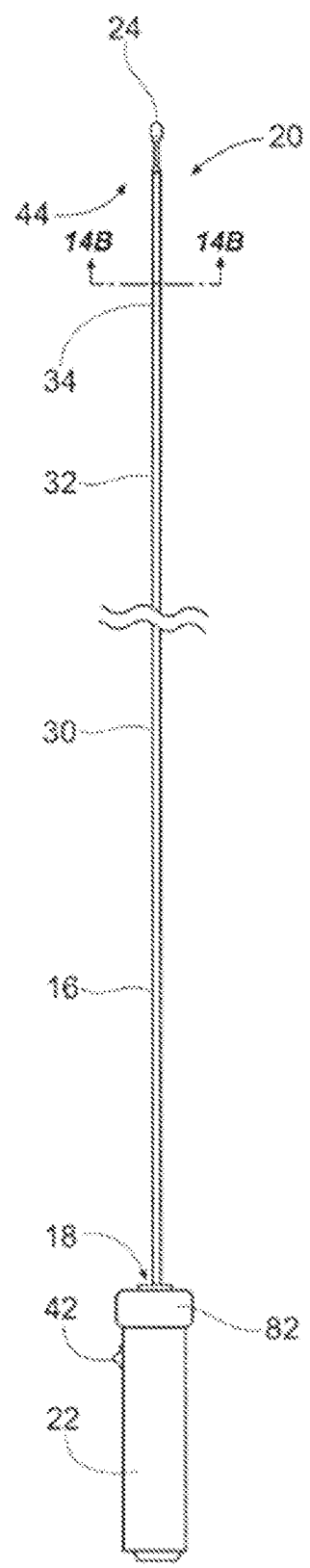
FIGS. 14A to 14C show alternative embodiments of the intermediate flexure zone of the elongated shaft of the treatment device shown in FIG. 5.
Figure 14B:
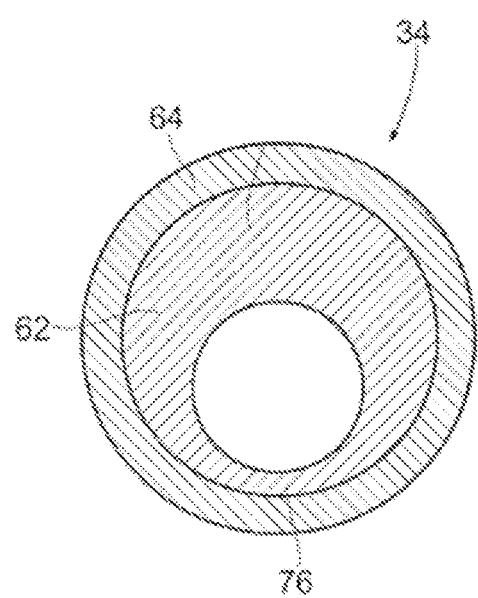
Figure 14C:
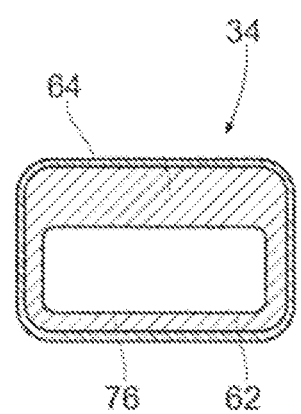

Alternatively, as FIGS. 14B and 140 show, the third tubular structure 62 can comprise an eccentric polymer or metal/polymer composite, which can be braided or coiled. The third tubular structure 62 can also take the form of an eccentric oval, or rectangular, or flattened metal coil or polymer (as FIG. 14C shows). In either arrangement, the thinner wall segment 76 (less stiff) is oriented on the third tubular structure 62 on the same side as the actuator wire attached.

4. Distal Flexure Zone

As shown in FIGS. 15A to 15H, the distal flexure zone 44 comprises a spring-like flexible tubular structure 74. The flexible structure 74 can comprise a metal, a polymer, or a metal/polymer composite. The material and physical features of the flexible structure 74 are selected so that the axial stiffness and torsional stiffness of the flexible structure 74 is not greater than the axial stiffness and torsional stiffness of the third tubular structure 62. The overall flexibility of the flexible structure 74 is at least equal to and desirably greater than the flexibility of third tubular structure 62 when the third tubular structure has not been deflected by the control wire 40.

As shown in FIG. 15B, the thermal heating element 24 is carried at the distal end of the flexible structure 74 for placement in contact with tissue along a vessel wall of a respective renal artery.

The material selected for the flexible structure 74 can be radiopaque or non-radiopaque. Desirably, the flexible member includes a radiopaque material, e.g., stainless steel, platinum, platinum iridium, or gold, to enable visualization and image guidance. Alternatively, a non-radiopaque material can be used that is doped with a radiopaque substance, such as barium sulfate.

The configuration of the flexible structure 74 can vary. For example, in the embodiment depicted in FIGS. 15B and 15C, the flexible structure 74 comprises a thread 104 encased in or covered with a polymer coating or wrapping 110. The thread 104 is routed through a proximal anchor 108, which is attached to the distal end of the intermediate flexure zone 34, and a distal anchor 106, which is fixed within or integrated into the heating element 24/electrode 46 using solder. Although various types of materials can be used to construct the aforementioned structures, in order to have a flexible structure 74 that securely connects to the intermediate flexure zone 34 and the thermal heating element 24, it is desirable for thread 104 to be comprised of Kevlar or similar polymer thread and for the proximal anchor 108 and distal anchor 106 to be comprised of stainless steel. While the coating 110 can be comprised of any electrically insulative material, and particularly those listed later with respect to sheath 80, is desirable for the structures of the flexible structure 74 to be encased/coated/covered by a low-durometer polymer such as carbothane laminate 110. As shown in FIG. 15C, one or more supply wires 112 may run alongside or within the flexible structure 74. As previously mentioned these wires may provide the thermal heating element 24 with electrical current/energy from the generator 26 and also convey data signals acquired by sensor 52. Also as previously mentioned and depicted in FIG. 15C, the control wire 40 from the handle actuator 42 can be formed into the proximal anchor 108 and attached to the elongated shaft using solder 130.

One advantage of the above-described configuration of the flexible structure 74 is that the flexible structure 74 creates a region of electrical isolation between the thermal heating element and the rest of the elongated shaft. Both the Kevlar thread 104 and laminate 110 are electrically insulative, thereby providing the supply wire(s) 112 as the sole means for electrical connectivity.

As shown in FIGS. 15D through 15F, the flexible structure 74 allows considerable passive deflection of the distal flexure zone 44 when the thermal heating element 24 is put into contact with the vessel wall. As already described, this flexibility has several potential benefits. The size and configuration of the flexible structure 74 enables the thermal heating element to deflect in many directions because the distal flexure zone may bend by angle $\Theta$ in any plane through the axis of the distal end region. For treatments within a peripheral blood vessel such as the renal artery, it is desirable that angle $\Theta \leq 90$ degrees.

Figure 15G:
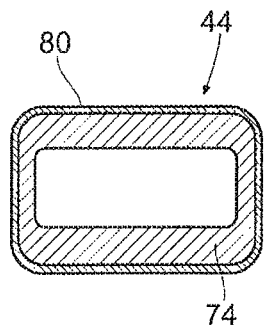
FIGS. 15G and 15H show alternative embodiments of the distal flexure zone corresponding to the elongated shaft of the treatment device shown in FIG. 5.
Figure 15H:
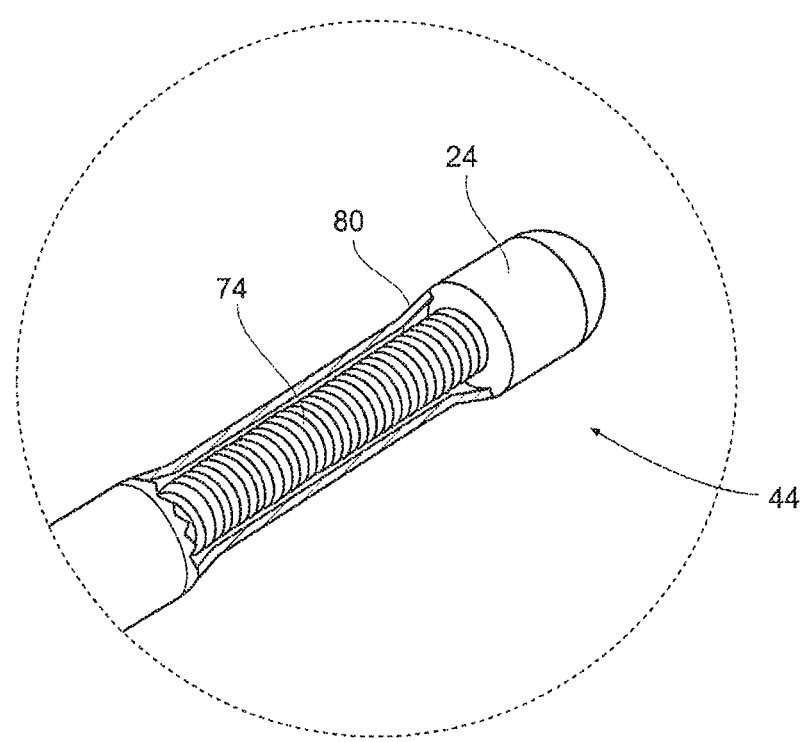

In alternative embodiments for the distal flexure zone 44, the flexible structure 74 can take the form of a tubular metal coil, cable, braid or polymer, as FIG. 15H shows. Alternatively, the flexible structure 74 can take the form of an oval, or rectangular, or flattened metal coil or polymer, as FIG. 15G shows. In alternate embodiments, the flexible structure 74 may comprise other mechanical structures or systems that allow the thermal heating element 24 to pivot in at least one plane of movement. For example, the flexible structure 74 may comprise a hinge or ball/socket combination.

Figures 15I, 15J:
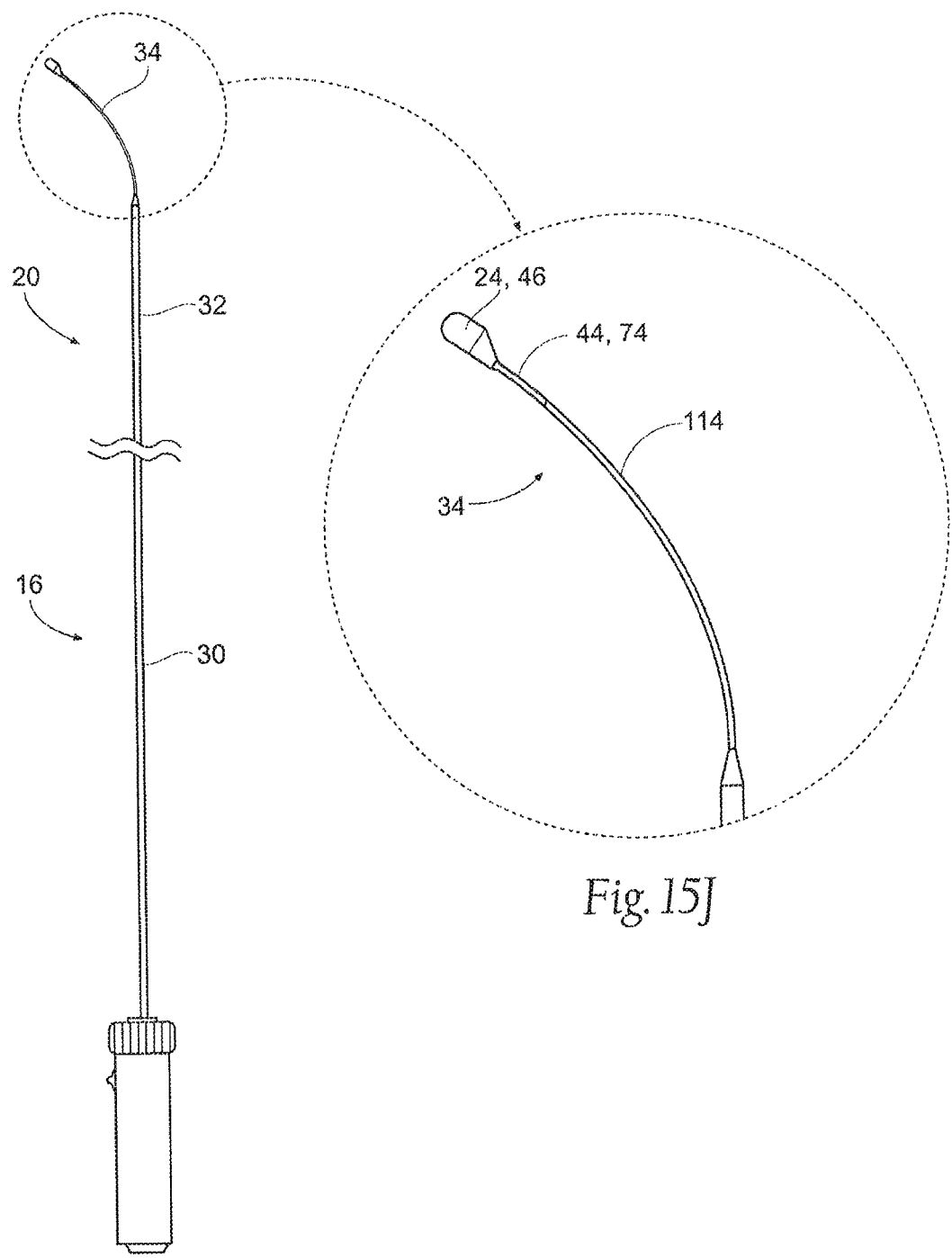
FIGS. 15I and 15J show an alternative catheter embodiment of the treatment device shown in FIG. 5 comprising an intermediate section comprising an arch wire.

The flexible structure 74 as a part of the distal flexure zone can be coupled to the intermediate flexure zone as describe above. Alternatively, in embodiments that do not provide an intermediate flexure zone, the distal flexure zone can be coupled to the proximal flexure zone. Still alternatively, the distal flexure zone can be coupled to an intermediate section comprising an arch wire as described in co-pending patent application Ser. No. 12/159,306, filed Jun. 26, 2008, which is incorporated herein in its entirety. For example, FIGS. 15I and 15J provide a catheter comprising a shaft 16 and a distal end region 20, wherein the distal end region 20 comprises an intermediate section 34, a distal flexure zone 44 and a thermal heating element 24. More specifically, the catheter may comprise an intermediate section comprising an arch wire 114, a distal flexure zone comprising a flexible structure, and a thermal heating element comprising an electrode 46, wherein the flexible structure is coupled to the arch wire and electrode.

If the flexible member comprises, in whole or in part, an electrically conductive material, the distal flexure zone 44 desirably includes an outer sheath 80 (see FIGS. 15G and 15M) or covering over the flexible structure 74 made from an electrically insulating polymer material. The polymer material also possesses a desired durometer for flexibility of the flexible member (e.g., 25D to 55D).

Candidate materials for the polymer material include polyethylene terephthalate (PET); Pebax; polyurethane; urethane, carbothane, tecothane, low density polyethylene (LDPE); silicone; or combinations thereof. The polymer material can be laminated, dip-coated, spray-coated, or otherwise deposited/applied over the flexible structure 74. Alternatively, a thin film of the polymer material (e.g., PTFE) can be wrapped about the flexible structure 74.

Alternatively, the flexible structure 74 can be inherently insulated, and not require a separate sheath 56 or covering. For example, the flexible member can comprise a polymer-coated coiled wire.

5. Rotation Controller

As will be discussed later in greater detail, it is desirable to rotate the device within the renal artery after the thermal heating element is in contact the vessel wall. However, it may be cumbersome and awkward for a clinical practitioner to rotate the entire handle at the proximal end of the device, particularly given the dimensions of the renal anatomy. In one representative embodiment, as shown in FIGS. 16A and 16B, the proximal end of the shaft 16 is coupled to the handle 22 by a rotating fitting 82.

The rotating fitting 82 is mounted by a tab 84 (see FIG. 16B) carried in a circumferential channel 86 formed on the distal end of the handle 22. The rotating fitting 82 can thus be rotated at the distal end of the handle 22 independent of rotation of the handle 22.

The proximal end of the force transmitting section 30 is attached to a stationary coupling 88 on the rotating fitting 82. Rotation of the rotating fitting 82 (as FIG. 16A shows) thereby rotates the force transmitting section 30, and, with it, the entire elongated shaft 16, without rotation of the handle 22. As FIG. 16A shows, a caregiver is thereby able to hold the proximal portion of the handle 22 rotationally stationary in one hand and, with the same or different hand, apply a torsional force to the rotating fitting 82 to rotate the elongated shaft 16. This allows the actuator to remain easily accessed for controlled deflection.

Figure 16C:
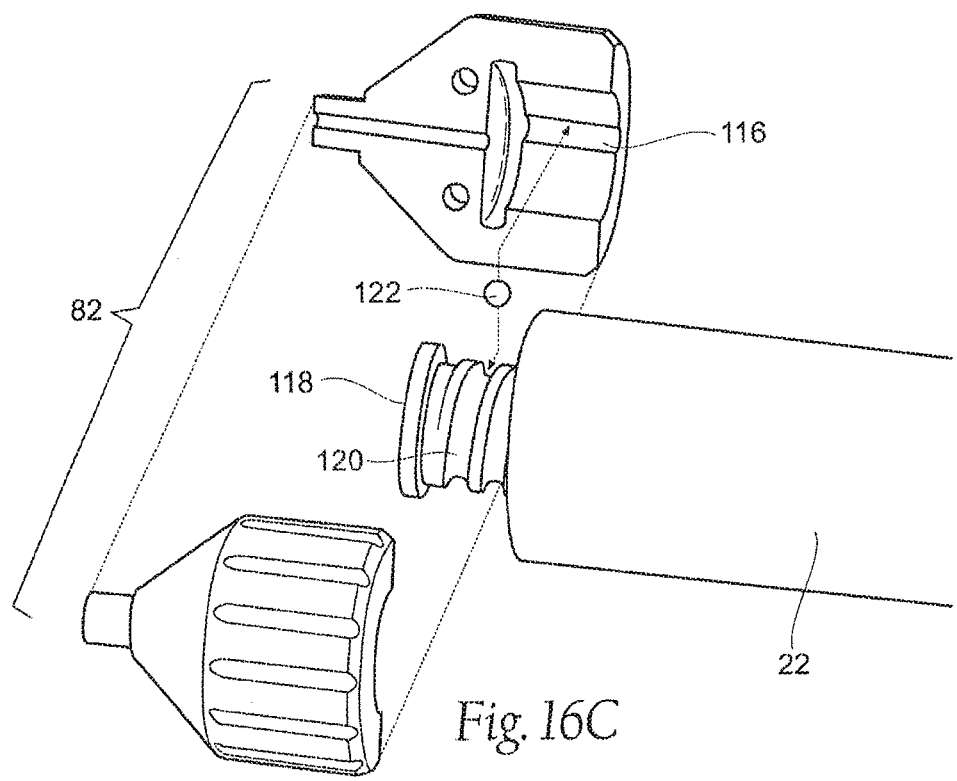
FIGS. 16C and 16D show a handle of the treatment device shown in FIG. 5 with a rotational control mechanism having a rotational limiting element and an actuator lever.

Since there are cables and wires running from the handle through the shaft of the device (e.g., actuation wire/cable, electrical transmission wire(s), thermocouple wire(s), etc.), it is desirable to limit rotation of the shaft relative to these wires in order to avoid unnecessary entanglement and twisting of these wires. The handle embodiment depicted in FIG. 16C provides a rotational limiting element to address this need. In this embodiment, the rotating fitting 82 includes an axial groove 116 and the distal portion of the handle 22 comprises a fitting interface 118 having a helical channel 120. A ball 122 comprising stainless steel or another metal or a polymer is placed within the fitting interface 118 so that it, upon rotation of the fitting, may simultaneously travel within the helical channel 120 of the fitting interface 118 and along the axial groove 116 of the fitting. When the ball 122 reaches the end of the channel and/or groove, the ball will no longer move and, consequently, the fitting will not be able to rotate any further in that direction. The rotational fitting 82 and handle fitting interface 118 can be configured to allow for the optimal number of revolutions for the shaft, given structural or dimensional constraints (e.g., wires). For example, the components of the handle could be configured to allow for two revolutions of the shaft independent of the handle.

As has been described and will be described in greater detail later, by intravascular access, the caregiver can manipulate the handle 22 to locate the distal end region 20 of the elongated shaft 16 within the respective renal artery. The caregiver can then operate the actuator 42 on the handle 22 (see FIG. 16A) to deflect the thermal heating element 24 about the intermediate flexure zone 34. The caregiver can then operate the rotating fitting 82 on the handle 22 (see FIGS. 16A and 16D) to apply a rotational force along the elongated shaft 16. The rotation of the elongated shaft 16 when the intermediate flexure zone 34 is deflected within the respective renal artery rotates the thermal heating element 24 within the respective renal artery, making it easier to achieve contact with the vessel wall and determine whether there is wall contact, particularly in planes where there is poor angiographic visualization.

Figure 16D:
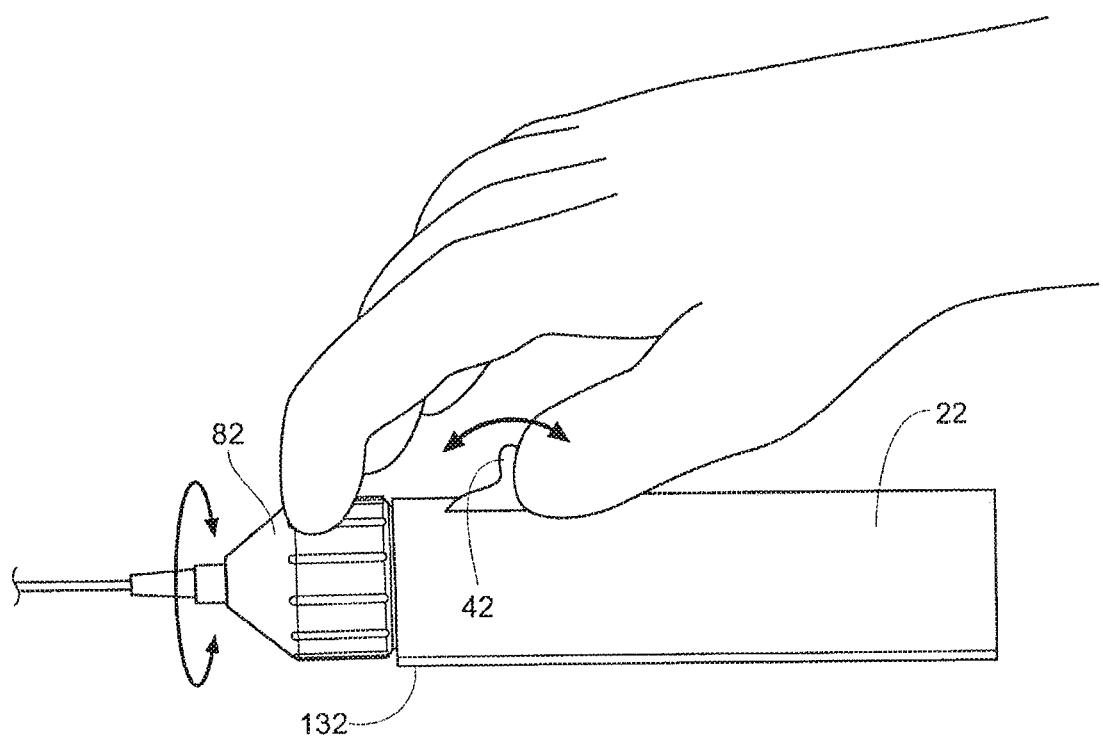

In an additional aspect of the disclosed technology, the handle 22 may be configured to minimize operator/caregiver handling of the device while it is within the patient. As shown in FIG. 16D, the handle also comprises a lower surface 132 that substantially conforms to the surface beneath (e.g., operating table). This lower surface 132, which is shown to be substantially flat in FIG. 16D, can alternatively be curved, shaped or angled depending on the configuration and/or geometry of the beneath surface. The conforming lower surface 132 enables the clinical operator to keep the handle 22 stable when the treatment device 12 is within the patient. In order to rotate the device when it is inside the patient, the operator can simply dial the rotating fitting 82 without any need to lift the handle. When the operator desires to retract the device for subsequent treatments, the operator can simply slide the handle along the beneath surface to the next position. Again, this mitigates the risk of injury due to operator error or over handling of the treatment device. Additionally or alternatively, the lower surface can engage the surface underneath using clips, texture, adhesive, etc.

Additional enhancements to the rotation mechanism disclosed herein include providing tactile and/or visual feedback on the rotational fitting so that the operator can exercise greater control and care in rotating the device. The rotating fitting 82 can also be selectively locked to the interface, thereby preventing further rotation, if the operator wishes to hold the treatment device in a particular angular position. Another potential enhancement includes providing distance markers along the shaft/handle to enable the operator to gage distance when retracting the treatment device.

B. Second Representative Embodiment (Distal Flexure Zone Comprises a Flexible Active Electrode)

Figure 17A:
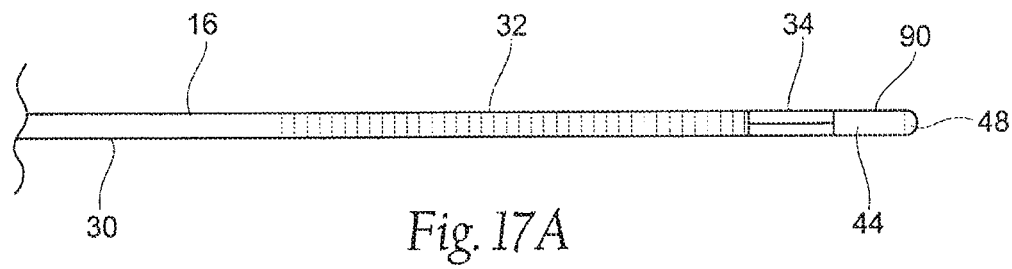
FIGS. 17A and 17B show an alternative representative embodiment of an elongated shaft for a treatment device like that shown in FIG. 5, showing examples of the different mechanical and functional regions that the elongated shaft can incorporate.
Figure 17B:
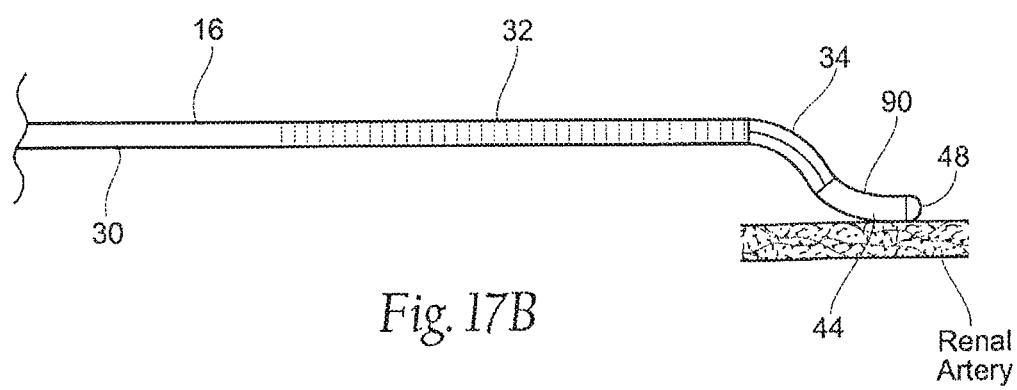

FIGS. 17A and 17B show a representative embodiment of an elongated shaft 16 that includes a proximal force transmitting section 30, proximal flexure zone 32, intermediate flexure zone 34, and a distal flexure zone 44. In this embodiment, the materials, size, and configuration of the proximal force transmitting section 30, proximal flexure zone 32, and intermediate flexure zone 34 are comparable to the respective counterparts described in the first representative embodiment.

In this embodiment, however, the distal flexure zone 44 is sized and configured to itself serve as an active, flexible electrode 90. In diameter, the active, flexible electrode 90 is sized and configured to be equal to or greater than the intermediate flexure zone 34. The total surface area TSA of the active, flexible electrode 90 is thereby increased, so that the possible active surface area of the electrode 46 is increased as well.

Also, in this arrangement, the entire length of the active flexible electrode 90 shares the flexibility properties of the distal flexure zone 44, as previously described. Materials are selected that, in addition to imparting the desired flexibility, are electrically conductive as well. The active electrode 90 is thereby flexible enough along its entire length to conform closely against the vessel wall, thereby further increasing the possible active surface area of the electrode. The active flexible electrode 90 may also more readily deflect away from the vessel wall when engaging the vessel wall head-on, to thereby minimize the forces exerted against the vessel wall as the electrode 90 is placed into side-on relationship with the vessel wall. The active, flexible electrode 90 can thereby be considered more atraumatic.

In the illustrated embodiment, the active, flexible electrode 90 further desirably includes a distal region that is tapered to form a blunt, atraumatic end surface 48. The end surface 48 can be formed from metal materials by laser, resistive welding, or machining techniques. The end surface 48 can also be formed from polymer materials by bonding, lamination, or insert molding techniques.

C. Third Representative Embodiment (Distal flexure zone Includes Substantially Spherical Active Electrode)

Figure 18A:
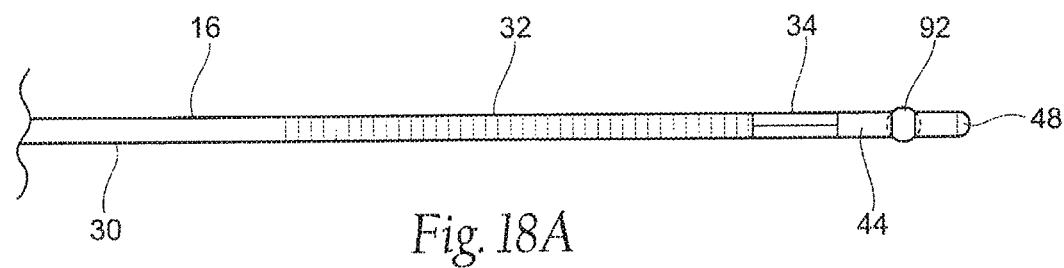
FIGS. 18A and 18B show another alternative representative embodiment of an elongated shaft for a treatment device like that shown in FIG. 5, showing examples of the different mechanical and functional regions that the elongated shaft can incorporate.
Figure 18B:
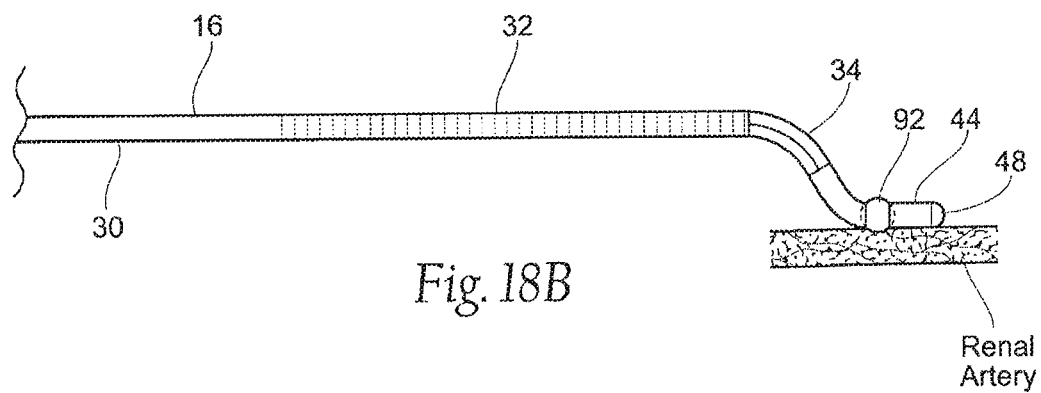

FIGS. 18A and 18B show a representative embodiment of an elongated shaft 16 that includes a proximal force transmitting section 30, proximal flexure zone 32, and a intermediate flexure zone 34, and a distal flexure zone 44. In this embodiment, the materials, size, and configuration of the proximal force transmitting section 30, proximal flexure zone 32, and intermediate flexure zone 34 are comparable to the respective counterparts in the first and second embodiments.

In this embodiment, however, the distal flexure zone 44 is sized and configured to carry a substantially spherical or cylindrical active electrode 92 at a location more proximally spaced from its distal end. In this embodiment, the distal flexure zone 44 shares the flexibility characteristics of the distal flexure zone 44, as previously described. In diameter, however, the distal flexure zone 44 is sized and configured to be approximately equal to the intermediate flexure zone 34. In diameter, the spherical active electrode 92 is sized to be larger than the diameter of the distal flexure zone 44. Therefore, flexure of the distal flexure zone 44 can place the spherical electrode 92 into contact with a greater tissue area, thereby increasing the active surface area (ASA) of the electrode.

In the illustrated embodiment, the distal flexure zone 44 desirably includes a distal region that is tapered to form a blunt, atraumatic end surface 48. The end surface 48 can be formed from metal materials by laser, resistive welding, or machining techniques. The end surface 48 can also be formed from polymer materials by bonding, lamination, or insert molding techniques.

The spherical electrode 92 can be attached to the distal flexure zone 44 e.g., by spot welding, laser welding, or soldering techniques. The placement of the spherical electrode 92 along the length of the distal flexure zone 44 can vary. It can be placed, e.g., in the approximate mid-region of the distal flexure zone 44, or closer to the distal end than the proximal end, or vice versa.

IV. Use of the System

A. Intravascular Delivery, Deflection and Placement of the Treatment Device

Any one of the embodiments of the treatment devices 12 described herein can be delivered over a guide wire using conventional over-the-wire techniques. When delivered in this manner (not shown), the elongated shaft 16 includes a passage or lumen accommodating passage of a guide wire.

Alternatively, any one of the treatment devices 12 described herein can be deployed using a conventional guide catheter or pre-curved renal guide catheter 94.

When using a guide catheter 94 (see FIG. 6A), the femoral artery is exposed and cannulated at the base of the femoral triangle, using conventional techniques. In one exemplary approach, a guide wire (not shown) is inserted through the access site and passed using image guidance through the femoral artery, into the iliac artery and aorta, and into either the left or right renal artery. A guide catheter can be passed over the guide wire into the accessed renal artery. The guide wire is then removed. Alternatively, a renal guide catheter (shown in FIG. 19A), which is specifically shaped and configured to access a renal artery, can be used to avoid using a guide wire. Still alternatively, the treatment device can be routed from the femoral artery to the renal artery using angiographic guidance and without the need of a guide catheter.

When a guide catheter is used, at least three delivery approaches can be implemented. In one exemplary approach, one or more of the aforementioned delivery techniques can be used to position a guide catheter within the renal artery just distal to the entrance of the renal artery. The treatment device is then routed via the guide catheter into the renal artery. Once the treatment device is properly positioned within the renal artery, the guide catheter is retracted from the renal artery into the abdominal aorta. In this approach, the guide catheter should be sized and configured to accommodate passage of the treatment device. For example, a 6 French guide catheter can be used.

In a second exemplary approach, a first guide catheter is placed at the entrance of the renal artery (with or without a guide wire). A second guide catheter is passed via the first guide catheter (with or without the assistance of a guide wire) into the renal artery. The treatment device is then routed via the second guide catheter into the renal artery. Once the treatment device is properly positioned within the renal artery the second guide catheter is retracted, leaving the first guide catheter at the entrance to the renal artery. In this approach the first and second guide catheters should be sized and configured to accommodate passage of the second guide catheter within the first guide catheter (i.e., the inner diameter of the first guide catheter should be greater than the outer diameter of the second guide catheter). For example, the first guide catheter could be 8 French in size and the second guide catheter could be 5 French in size.

In a third exemplary approach, and as shown in FIG. 19A, a renal guide catheter 94 is positioned within the abdominal aorta, just proximal to the entrance of the renal artery. As now shown in FIG. 19B, the treatment device 12 as described herein is passed through the guide catheter 94 and into the accessed renal artery. The elongated shaft makes atraumatic passage through the guide catheter 94, in response to forces applied to the force transmitting section 30 through the handle 22. The proximal flexure zone 32 accommodates significant flexure at the junction of the left/right renal arteries and aorta to gain entry into the respective left or right renal artery through the guide catheter 94 (as FIG. 19B shows).

Figure 19C:
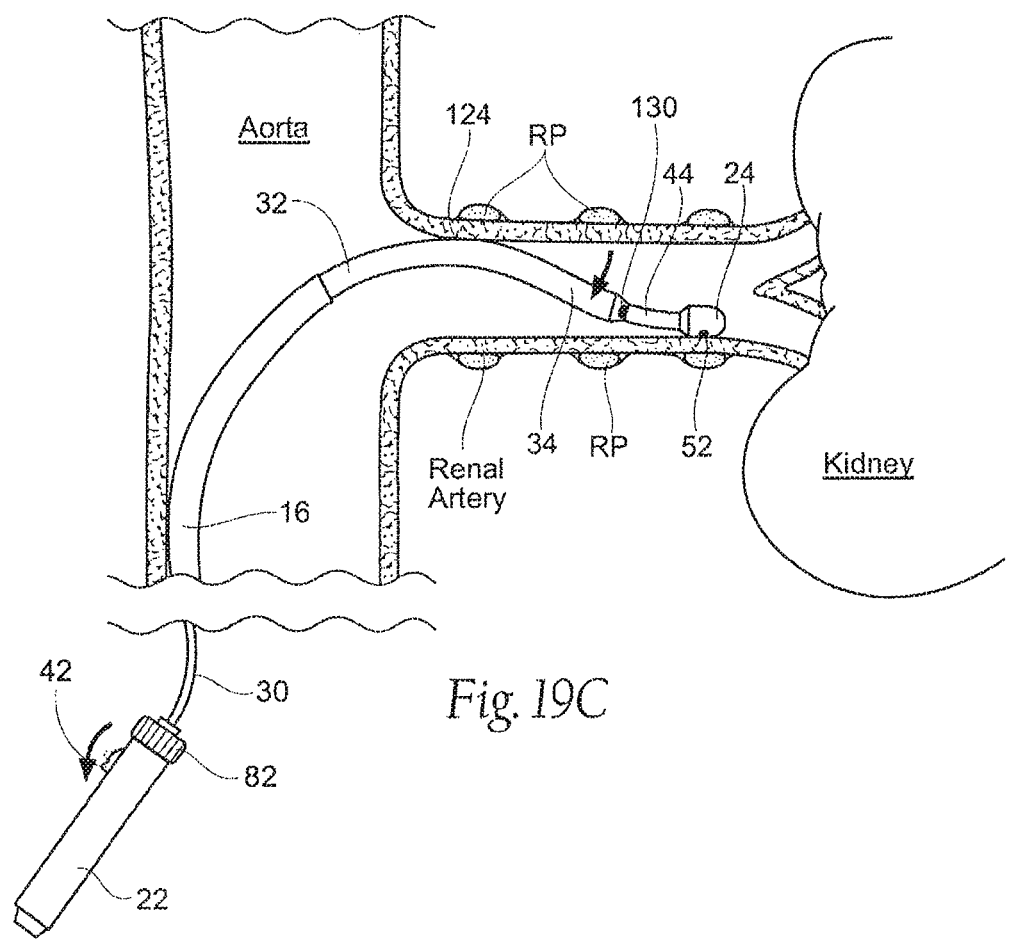

As FIG. 19C shows, the intermediate flexure zone 34 on the distal end portion of the elongated shaft 16 can now be axially translated into the respective renal artery, remotely deflected and/or rotated in a controlled fashion within the respective renal artery to attain proximity to and a desired alignment with an interior wall of the respective renal artery. As FIG. 19C further shows, the distal flexure zone 44 bends to place the thermal energy heating element into contact with tissue on the interior wall.

Figure 19D:
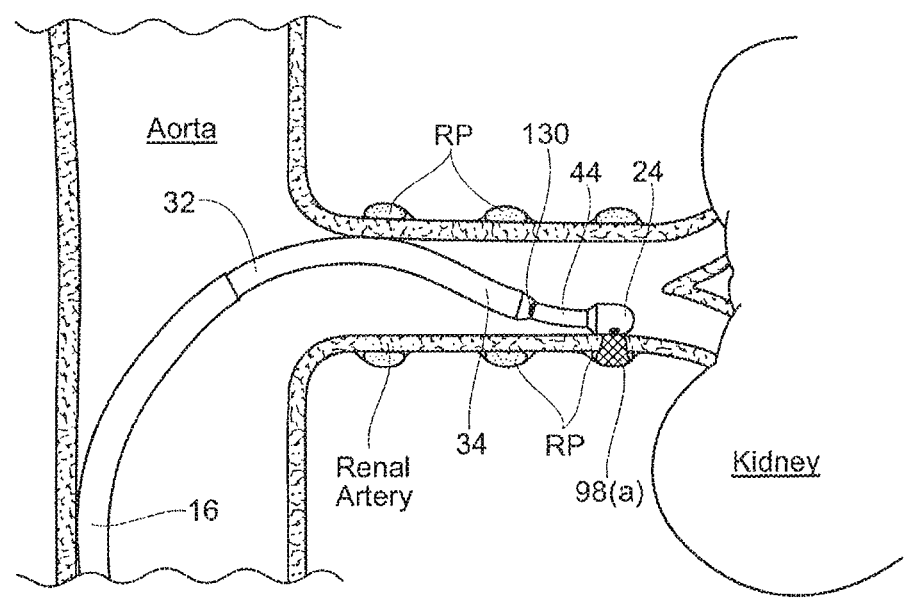

As FIG. 19D shows, the complex, multi-bend structure formed by the proximal, intermediate and distal zones 32, 24, and 44 of the distal end region 20 of the elongated shaft 16 creates a consistent and reliable active surface area of contact between the thermal heating element 24 and tissue within the respective renal artery (refer back to FIG. 8C). Thermal energy can now be applied through the thermal heating element 24 to induce one or more thermal heating effects on localized regions of tissue along the respective renal artery.

B. Facilitating Contact with the Vessel Wall

Figure 19E:
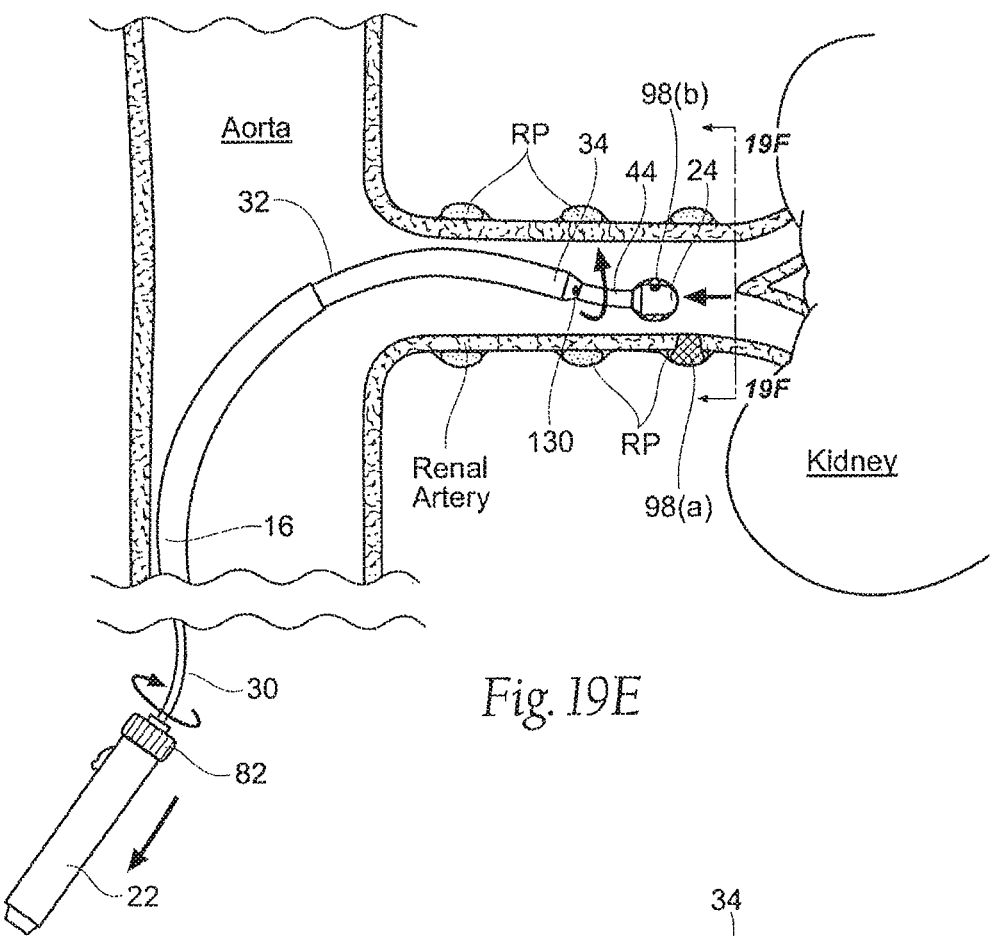

As previously described, the actuation of the control wire 40 to deflect the intermediate flexure zone 32 helps position the thermal heating element 24 in contact with the vessel wall. This is particularly useful when the distal end region 20 of the treatment device 12 is delivered into the renal artery, as shown in FIG. 19B. Due to the curve and placement of the renal guide catheter 94 and orientation of the treatment device 12, the distal end region 20 of the treatment device is oriented up against the superior region of the vessel wall when first delivered into the renal artery, as shown in FIG. 19B. Once the distal end region is positioned at the most distal portion of the main renal artery, the operator may deflect the intermediate flexure zone 34 via the actuator 42 to position the thermal heating element 24 into contact with the vessel wall at a more inferior location, as shown in FIG. 19C. This deflection of the intermediate flexure zone 34 establishes wall contact and provides, via the distal flexure zone 44, a stabilizing force between the thermal heating element 24 and vessel wall to position the thermal heating element in contact with the vessel wall. The operator can then initiate treatment at this generally inferior (bottom) location or rotate the treatment device as shown in FIG. 19E for an alternate treatment location.

Figure 19F:
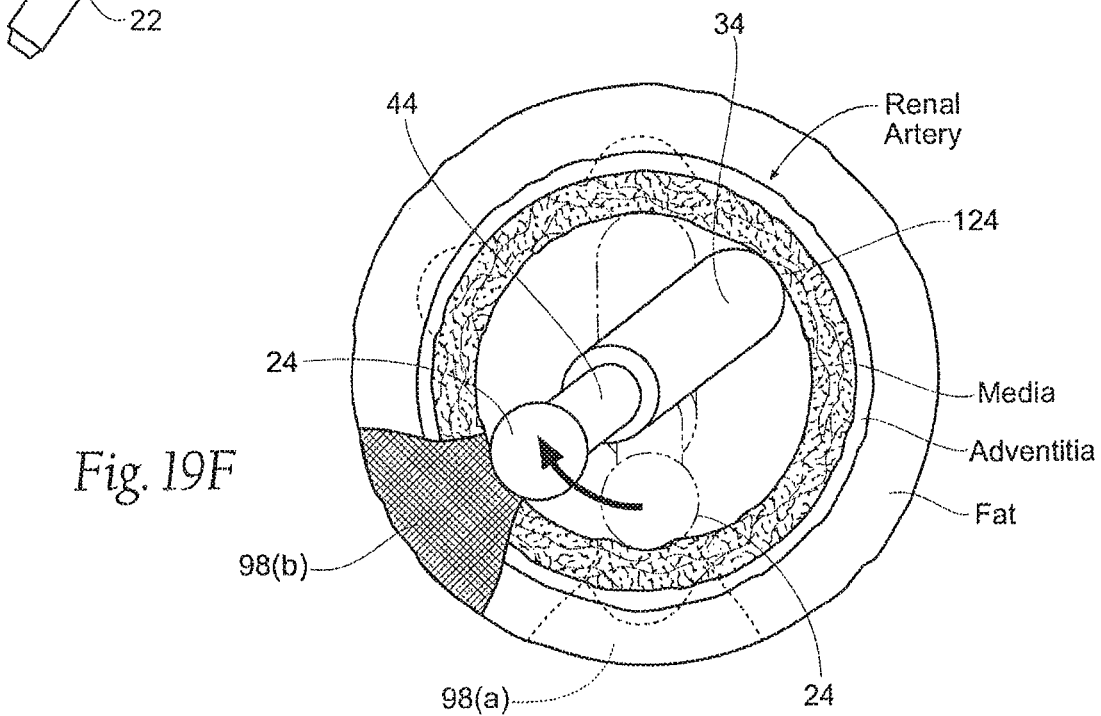

The active deflection of intermediate flexure zone 34 is facilitated by not only operation of actuator 42, but also contact between a proximal region of the intermediate flexure zone 44 and a superior region of the renal artery. As shown in FIG. 19O, this contact region 124 generally occurs at the apex of the bend of the intermediate flexure zone 34. This contact region 124 is in radial opposition to the contact between the thermal heating element 24 and vessel wall following deflection of the intermediate flexure zone 34. The stabilizing force provided by the intermediate flexure zone 44 to the thermal heating element 24 is also facilitated by the opposing force at contact region 124. Even when the operator rotates the treatment device to circumferentially reposition the thermal heating element, as shown in FIG. 19E, this opposition contact will be maintained, but at a different circumferential position. FIG. 19F shows the circumferential rotation of the thermal heating element 24 from a first treatment location corresponding to lesion 98($a$) to a second treatment location corresponding to lesion 98($b$) and the circumferential translation of the intermediate flexure zone 32 to a new contact region 124. It should be noted, however, that while having such opposition contact at contact region 124 facilitates wall contact and the stabilizing force, it is not generally required to achieve contact between the thermal heating element 24 and the vessel wall.

It certain embodiments, it may also be beneficial to equip the catheter apparatus with a second thermal heating element (not shown) at or in the vicinity of the intermediate flexure zone. Placement of the second thermal heating element on or proximate to the intermediate flexure zone may enable the creation of a thermally affected tissue region at or around contact region 124 (i.e., the portion of the vessel wall that is in contact with the intermediate flexure zone). Activation of the first thermal, element and the second thermal element would allow the operator to create two treatment zones that are circumferentially and longitudinally offset during a single placement of the catheter apparatus.

As described above, the size and configuration of the intermediate flexure zone 34 play a valuable role in the positioning of the device for treatment and in facilitating contact between the thermal heating element and the vessel wall. The dimensioning of the intermediate flexure zone also plays a valuable role in this regard, particularly with respect to the constraints imposed by the renal anatomy.

Figure 7E:
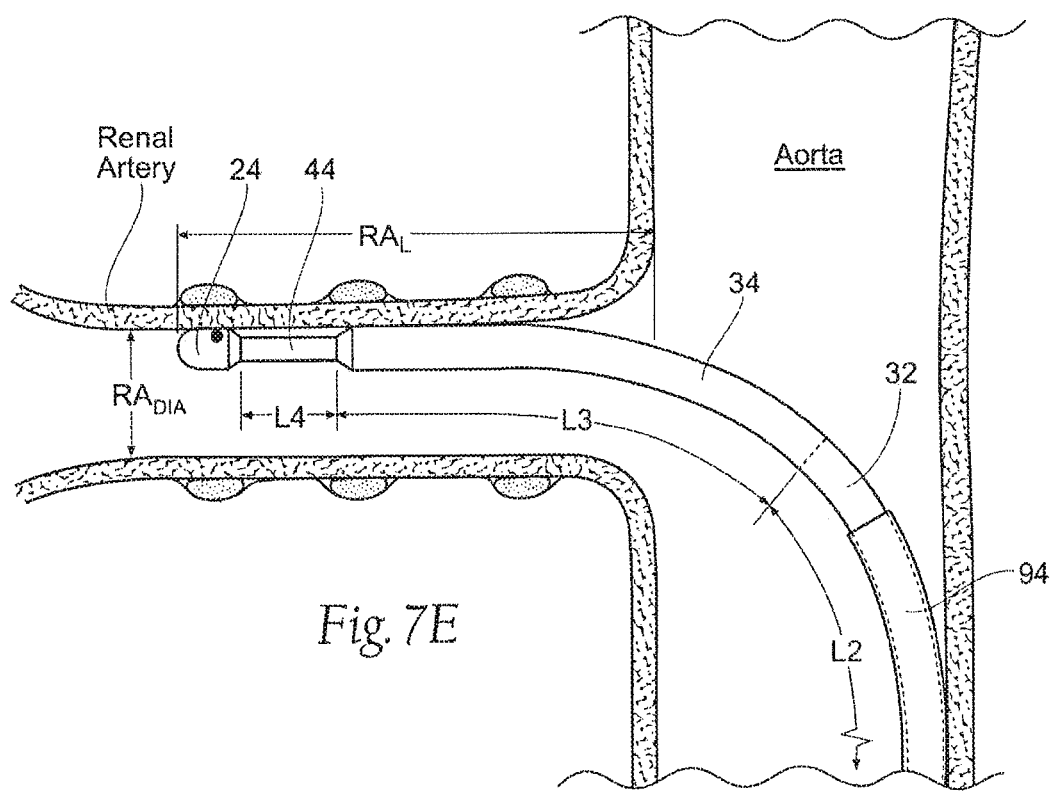
FIG. 7E shows an anatomic view of the placement of the treatment device shown in FIG. 5 within the dimensions of the renal artery.

Referring back to FIG. 7E, the length of the main branch of a renal artery (i.e., from the junction of the aorta and renal artery to just before the artery branches into multiple blood vessels going to the kidney) is $RA_L$ and the diameter of the main branch of a renal artery is $RA_{DIA}$. It is desirable for the length L3 of the intermediate flexure zone 34 to be long enough for the distal end region 20 of the treatment device 12 to reach a distal treatment location within the renal artery and, to be able to, upon deflection, translate the thermal heating element 24 to the radially opposite wall of the renal artery. However, if L3 were too long, then too much of the intermediate flexure zone's proximal region would reside within the aorta (even for distal treatments), thereby preventing contact at contact region 124 since the apex of the bend of the intermediate flexure zone would likely be in the aorta. Also, an L3 that is too long would deflect with a large radius of curvature (i.e., $\alpha 2$) and make it difficult for the operator to reliably achieve wall contact at both distal and proximal locations.

Additionally, as a practical matter, L3 is limited by the most distal treatment location (i.e., length of the renal artery) on one end and the location within the aorta of the renal guide catheter 94 on the other end. It would be undesirable for L3 to be so long that a portion of the intermediate flexure zone resides within the renal guide catheter during distal treatments since the deflection of the intermediate flexure zone within the guide could impair the ability of the operator to rotate and torque the catheter without whipping.

In an average human renal artery, $RA_L$ is about 20 mm to about 30 mm from the junction of the aorta and renal artery and the diameter of the main branch of a renal artery $RA_{DIA}$ is typically about 3 mm to about 7 mm or 8 mm. Given these and the above considerations, it is desirable that L3 range from about 5 mm to about 15 mm. In certain embodiments, particularly for treatments in relatively long blood vessels, L3 can be as long as about 20 mm. In another representative embodiment, L3 can be about 12.5 mm.

C. Creation of Thermally Affected Tissue Regions

As previously described (and as FIG. 19B shows), the thermal heating element 24 can be positioned by bending along the proximal flexure zone 32 at a first desired axial location within the respective renal artery. As FIG. 19C shows, the thermal heating element 24 can be radially positioned by deflection of intermediate flexure zone 34 toward the vessel wall. As FIG. 19O also shows, the thermal heating element 24 can be placed into a condition of optimal surface area contact with the vessel wall by further deflection of the distal flexure zone 44.

Once the thermal heating element 24 is positioned in the desired location by a combination of deflection of the intermediate flexure zone 34, deflection of the distal flexure zone 44 and rotation of the catheter, the first focal treatment can be administered. By applying energy through the thermal heating element 24, a first thermally affected tissue region 98($a$) can be formed, as FIG. 19D shows. In the illustrated embodiment, the thermally affected region 98($a$) takes the form of a lesion on the vessel wall of the respective renal artery.

After forming the first thermally affected tissue region 98($a$), the catheter needs to be repositioned for another thermal treatment. As described above in greater detail, it is desirable to create multiple focal lesions that are circumferentially spaced along the longitudinal axis of the renal artery. To achieve this result, the catheter is retracted and, optionally, rotated to position the thermal heating element proximally along the longitudinal axis of the blood vessel. Rotation of the elongated shaft 16 from outside the access site (see FIG. 19E) serves to circumferentially reposition the thermal heating element 24 about the renal artery. Once the thermal heating element 24 is positioned at a second axial and circumferential location within the renal artery spaced from the first-described axial position, as shown in FIG. 19E (e.g., 98(b)), another focal treatment can be administered. By repeating the manipulative steps just described (as shown in FIGS. 19F through 19K), the caregiver can create several thermally affected tissue regions 98(a), 98(b), 98(c) and 98(d) on the vessel wall that are axially and circumferentially spaced apart, with the first thermally affected tissue region 98(a) being the most distal and the subsequent thermally affected tissue regions being more proximal. FIG. 19I provides a cross-sectional view of the lesions formed in several layers of the treated renal artery. This figure shows that several circumferentially and axially spaced-apart treatments (e.g., 98(a)-98(d)) can provide substantial circumferential coverage and, accordingly, cause a neuromodulatory affect to the renal plexus. Clinical investigation indicates that each lesion will cover approximately 20-30 percent of the circumferential area surrounding the renal artery. In other embodiments, the circumferential coverage of each lesion can be as much as 50 percent.

In an alternative treatment approach, the treatment device can be administered to create a complex pattern/array of thermally affected tissue regions along the vessel wall of the renal artery. As FIG. 19L shows, this alternative treatment approach provides for multiple circumferential treatments at each axial site (e.g., 98, 99 and 101) along the renal artery. Increasing the density of thermally affected tissue regions along the vessel wall of the renal artery using this approach might increase the probability of thermally-blocking the neural fibers within the renal plexus.

Figure 19G:
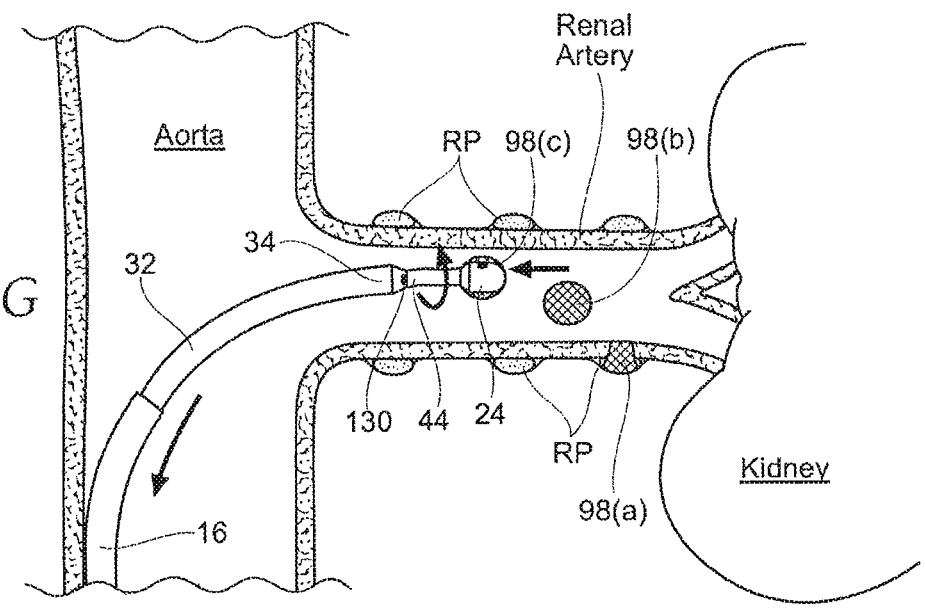
Figure 19H:
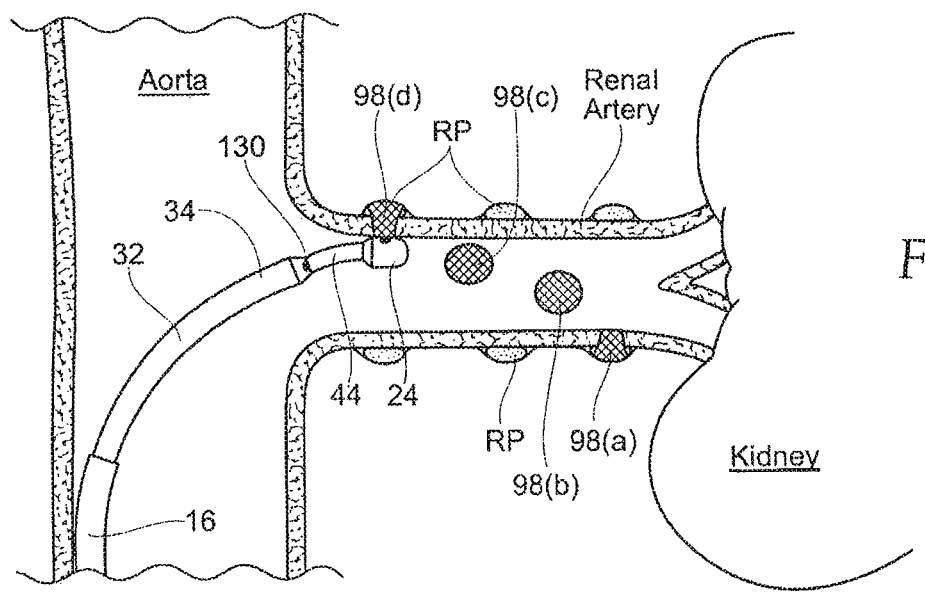
Figure 19I:
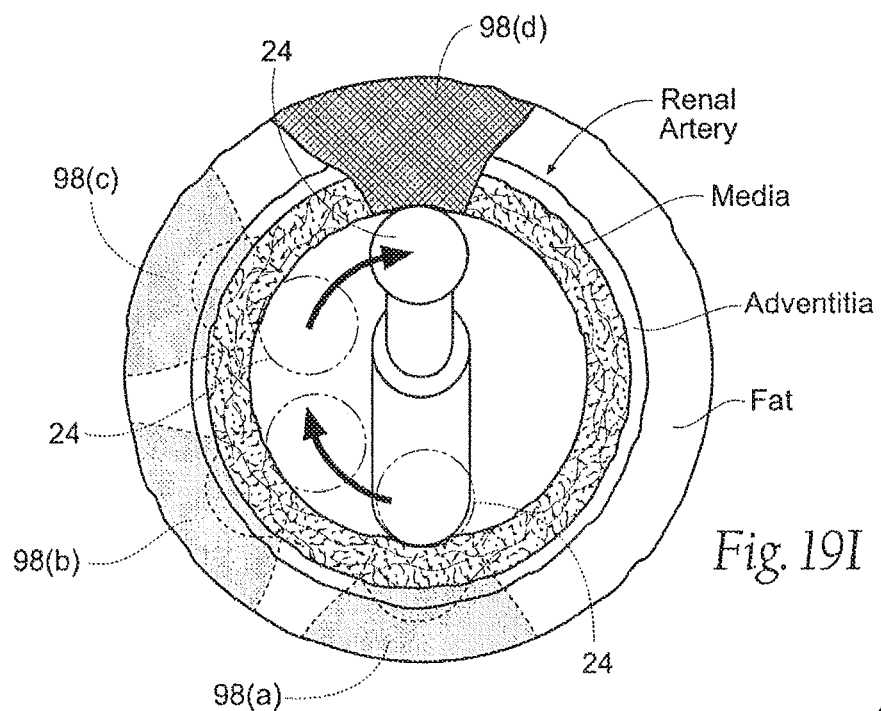
FIGS. 19I to 19K show the circumferential treatment effect resulting from intravascular use of a treatment device, like that shown in FIG. 5.
Figure 19J:
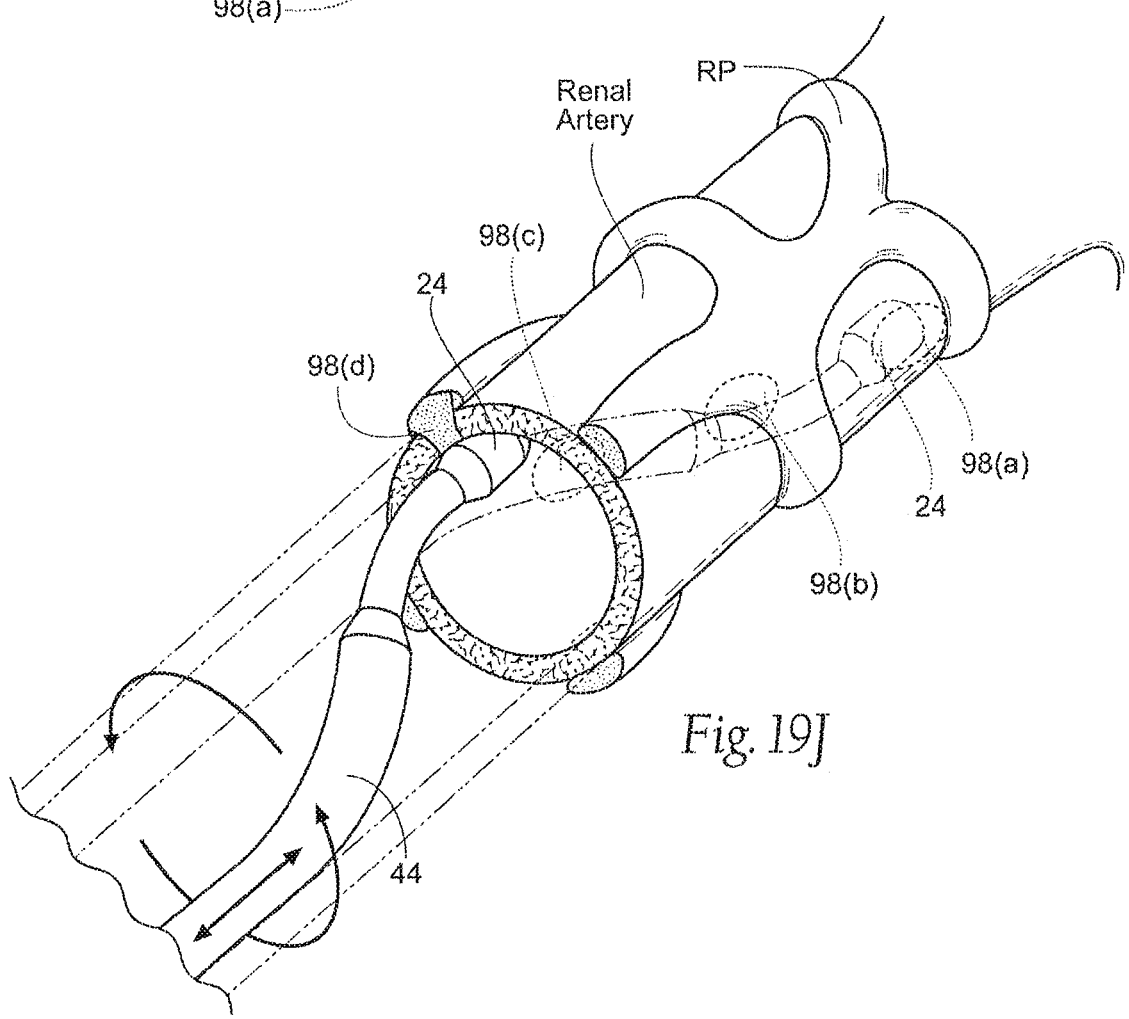
Figure 19K:
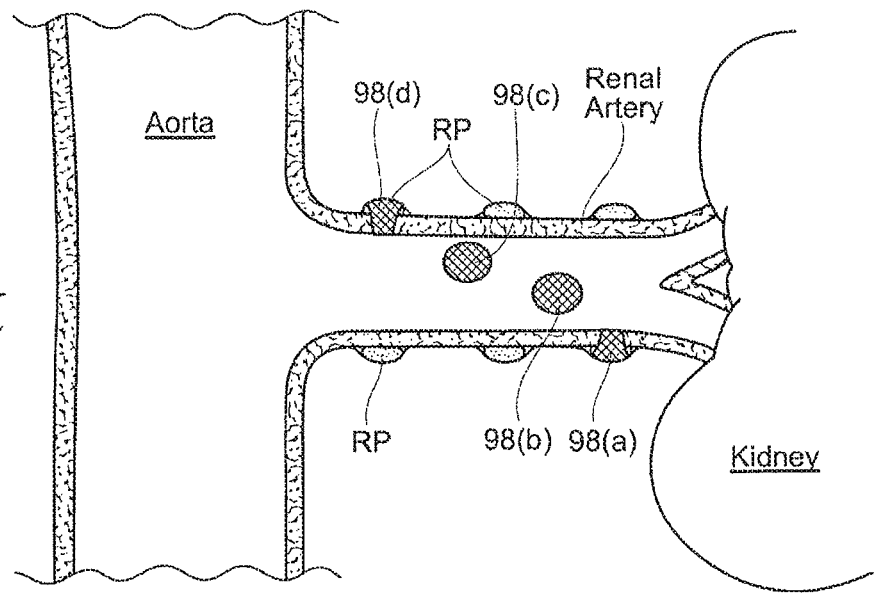
Figure 19L:
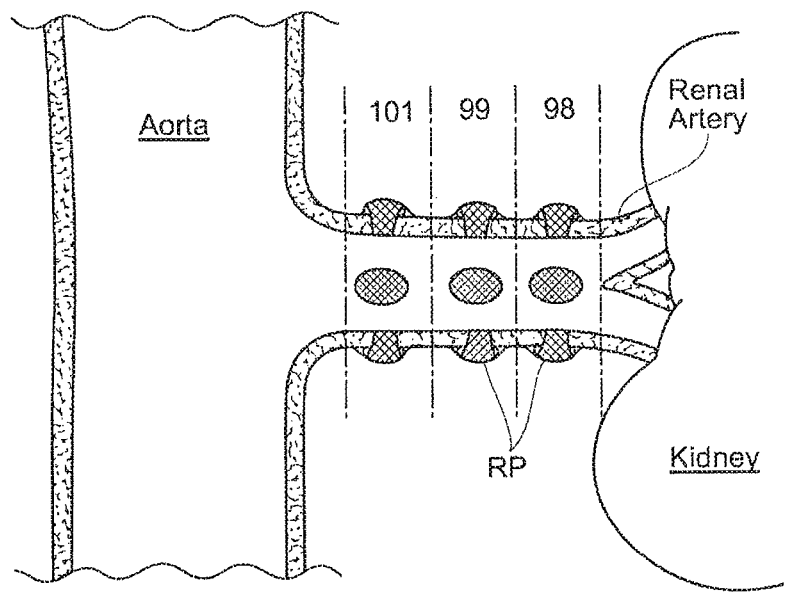
FIG. 19L shows an alternative intravascular treatment approach using the treatment device shown in FIG. 5.

The rotation of the thermal heating element 24 within the renal artery as shown in FIG. 19G helps improve the reliability and consistency of the treatment. Since angiographic guidance such as fluoroscopy only provides visualization in two dimensions, it is generally only possible in the anterior/posterior view to obtain visual confirmation of wall contact at the superior (vertex) and inferior (bottom) of the renal artery. For anterior and posterior treatments, it is desirable to first obtain confirmation of contact at a superior or inferior location and then rotate the catheter such that the thermal heating element travels circumferentially along the vessel wall until the desired treatment location is reached. Physiologic data such as impedance can be concurrently monitored to ensure that wall contact is maintained or optimized during catheter rotation. Alternatively, the C-arm of the fluoroscope can be rotated to achieve a better angle for determining wall contact.

Figure 22A:
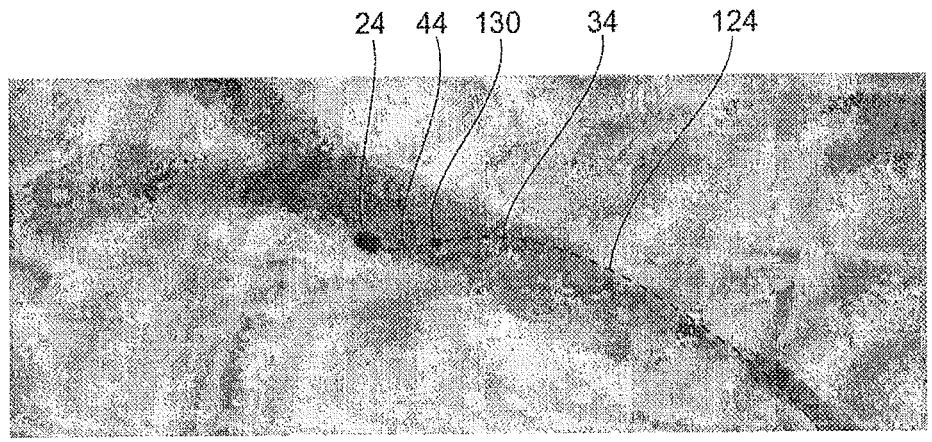
FIGS. 22A to 22C show fluoroscopic images of the treatment device shown in FIG. 5 in multiple treatment positions within a renal artery.
Figure 22B:
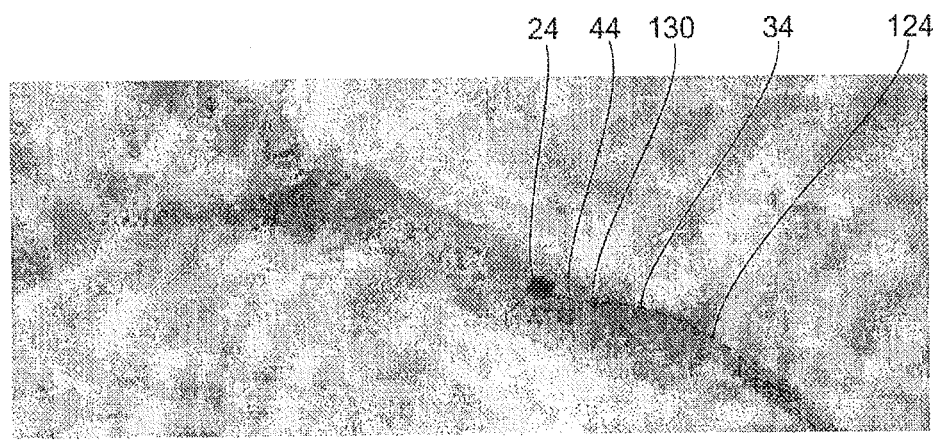
Figure 22C:

FIGS. 22A to 22C provide fluoroscopic images of the treatment device within a renal artery during an animal study. FIG. 22A shows positioning of the treatment device and thermal heating element 24 at a distal treatment location. The intermediate flexure zone 34 has been deflected to position the thermal heating element 24 in contact with the vessel wall and to cause flexure in the distal flexure zone 44. FIG. 22A also shows contact region 124 where the apex of the bend of the intermediate flexure zone 34 is in contact with the vessel wall in radial opposition to contact between the thermal heating element and vessel wall. FIG. 22B shows the placement of the treatment device at a more proximal treatment location following circumferential rotation and axial retraction. FIG. 22C shows the placement of the treatment device at a proximal treatment location just distal to the junction of the aorta and renal artery.

Since both the thermal heating element 24 and solder 130 at the distal end of the intermediate flexure zone 34 can be radiopaque, as shown in FIGS. 22A to 22C, the operator using angiographic visualization can use the image corresponding to the first treatment location to relatively position the treatment device for the second treatment. For example, in renal arteries of average length, it is desirable for the clinical operator to treat at about every 5 mm along the length of the main artery. In embodiments where the length of the distal flexure zone 44 is 5 mm, the operator can simply retract the device such that the current position of the thermal heating element 24 is longitudinally aligned with the position of the solder 130 in the previous treatment.

In another embodiment, solder 130 can be replaced by a different type of radiopaque marker. For example, a band of platinum can be attached to the distal end of the intermediate flexure zone to serve as a radiopaque marker.

Since angiographic visualization of the vasculature generally requires contrast agent to be infused into the renal artery, it may be desirable to incorporate within or alongside the treatment device a lumen and/or port for infusing contrast agent into the blood stream. Alternatively, the contrast agent can be delivered into the blood alongside the treatment device within the annular space between the treatment device and the guide catheter through which the device is delivered.

Exposure to thermal energy (heat) in excess of a body temperature of about 37° C., but below a temperature of about 45° C., may induce thermal alteration via moderate heating of the target neural fibers or of vascular structures that perfuse the target fibers. In cases where vascular structures are affected, the target neural fibers are denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity ("RSNA") is expected.

D. Control of Applied Energy

Desirably, the generator 26 includes programmed instructions comprising an algorithm 102 (see FIG. 5) for controlling the delivery of energy to the thermal heating device. The algorithm 102, as shown in FIG. 20, can be implemented as a conventional computer program for execution by a processor coupled to the generator 26. Algorithm 102 is substantially similar to the power delivery algorithm described in co-pending patent application Ser. No. 12/147,154, filed Jun. 26, 2008, which is incorporated herein by reference in its entirety. The algorithm 102 can also be implemented manually by a caregiver using step-by-step instructions.

When a caregiver initiates treatment (e.g., via the foot pedal), the algorithm 102 commands the generator 26 to gradually adjust its power output to a first power level $P_1$ (e.g., 5 watts) over a first time period $t_1$ (e.g., 15 seconds). The power increase during the first time period is generally linear. As a result, the generator 26 increases its power output at a generally constant rate of $P_1/t_1$. Alternatively, the power increase can be non-linear (e.g., exponential or parabolic) with a variable rate of increase. Once $P_1$ and $t_1$ are achieved, the algorithm can hold at $P_1$ until a new time $t_2$ for a predetermined period of time $t_2-t_1$ (e.g., 3 seconds). At $t_2$ power is increased by a predetermined increment (e.g., 1 watt) to $P_2$ over a predetermined period of time, $t_3-t_2$ (e.g., 1 second). This gradual power ramp can continue until a maximum power $P_{MAX}$ is achieved or some other condition is satisfied. In one embodiment, $P_{MAX}$ is 8 watts. In another embodiment $P_{MAX}$ is 10 watts.

The algorithm 102 includes monitoring certain operating parameters (e.g., temperature, time, impedance, power, etc.). The operating parameters can be monitored continuously or periodically. The algorithm 102 checks the monitored parameters against predetermined parameter profiles to determine whether the parameters individually or in combination fall within the ranges set by the predetermined parameter profiles. If the monitored parameters fall within the ranges set by the predetermined parameter profiles, then treatment can continues at the commanded power output. If monitored parameters fall outside the ranges set by the predetermined parameter profiles, the algorithm 102 adjusts the commanded power output accordingly. For example, if a target temperature (e.g., 65 degrees C.) is achieved, then power delivery is kept constant until the total treatment time (e.g., 120 seconds) has expired. If a first power threshold (e.g., 70 degrees C.) is achieved or exceeded, then power is reduced in predetermined increments (e.g., 0.5 watts, 1.0 watts, etc.) until a target temperature is achieved. If a second power threshold (e.g., 85 degrees C.) is achieved or exceeded, thereby indicating an undesirable condition, then power delivery can be terminated. The system can be equipped with various audible and visual alarms to alert the operator of certain conditions.

Figure 21:
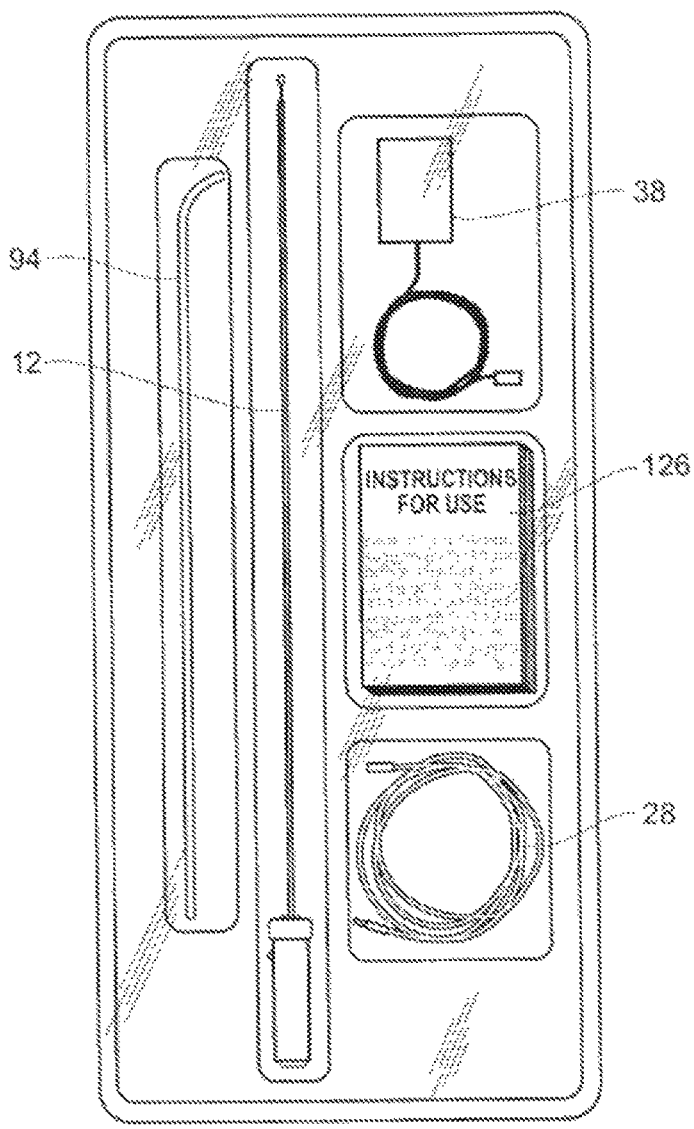
FIG. 21 shows several components of the system and treatment device shown in FIG. 5 packaged within a single kit.

V. Prepackaged Kit for Distribution, Transport and Sale of the Disclosed Apparatuses and Systems As shown in FIG. 21, one or more components of the system 10 shown in FIG. 5 can be packaged together for convenient delivery to and use by the customer/clinical operator. Components suitable for packaging include, the treatment device 12, the cable 28 for connecting the treatment device 12 to the generator 26, the neutral or dispersive electrode 38, and one or more guide catheters 94 (e.g., a renal guide catheter). Cable 28 can also be integrated into the treatment device 12 such that both components are packaged together. Each component may have its own sterile packaging (for components requiring sterilization) or the components may have dedicated sterilized compartments within the kit packaging. This kit may also include step-by-step instructions for use 126 that provides the operator technical product features and operating instructions for using the system 10 and treatment device 12, including all methods of insertion, delivery, placement and use of the treatment device disclosed herein.

VI. Additional Clinical Uses of the Disclosed Apparatuses, Methods and Systems

Although much of the disclosure in this Specification relates to at least partially denervating a kidney of a patient to block afferent and/or efferent neural communication from within a renal blood vessel (e.g., renal artery), the apparatuses, methods and systems described herein may also be used for other intravascular treatments. For example, the aforementioned catheter system, or select aspects of such system, can be placed in other peripheral blood vessels to deliver energy and/or electric fields to achieve a neuromodulatory affect by altering nerves proximate to these other peripheral blood vessels. There are a number of arterial vessels arising from the aorta which travel alongside a rich collection of nerves to target organs. Utilizing the arteries to access and modulate these nerves may have clear therapeutic potential in a number of disease states. Some examples include the nerves encircling the celiac trunk, superior mesenteric artery, and inferior mesenteric artery.

Sympathetic nerves proximate to or encircling the arterial blood vessel known as the celiac trunk may pass through the celiac ganglion and follow branches of the celiac trunk to innervate the stomach, small intestine, abdominal blood vessels, liver, bile ducts, gallbladder, pancreas, adrenal glands, and kidneys. Modulating these nerves either in whole (or in part via selective modulation) may enable treatment of conditions including (but not limited to) diabetes, pancreatitis, obesity, hypertension, obesity related hypertension, hepatitis, hepatorenal syndrome, gastric ulcers, gastric motility disorders, irritable bowel syndrome, and autoimmune disorders such as Chron's disease.

Sympathetic nerves proximate to or encircling the arterial blood vessel known as the inferior mesenteric artery may pass through the inferior mesenteric ganglion and follow branches of the inferior mesenteric artery to innervate the colon, rectum, bladder, sex organs, and external genitalia. Modulating these nerves either in whole (or in part via selective modulation) may enable treatment of conditions including (but not limited to) GI motility disorders, colitis, urinary retention, hyperactive bladder, incontinence, infertility, polycystic ovarian syndrome, premature ejaculation, erectile dysfunction, dyspareunia, and vaginismus.

While arterial access and treatments have received attention in this Specification, the disclosed apparatuses, methods and systems can also be used to deliver treatment from within a peripheral vein or lymphatic vessel.

VII. Additional Description

The term apparatus makes reference to any apparatus of the disclosure. In particular, this term relates to devices for achieving intravascular renal neuromodulation via thermal effects, such as heating. This term covers references to apparatus catheters, catheters, and treatment devices in general. In the specific description, the term catheter is used, but it should be understood that this is merely a particular example of the apparatuses of the disclosure.

Generally, the apparatus comprises an elongated shaft. The elongated shaft is sized and configured to deliver a thermal element to a renal artery via an intravascular path that includes a femoral artery, an iliac artery, and the abdominal aorta. As described in more detail above, different sectors of the elongated shaft serve different mechanical functions when in use. The elongated shaft may be in the form of a flexible tube.

The term apparatus includes, but is not necessarily limited to, a catheter. As will be appreciated by one skilled in the art, a catheter is a solid or tubular structure that can be inserted into a body cavity, lumen, duct or vessel. A process of inserting a catheter is catheterisation. The catheter, for example, may be an intravascular catheter suitable for insertion into and delivery through an intravascular path.

The intravascular path may be via a femoral artery, an iliac artery, and/or the aorta. The passage may be through an access site, percutaneously into the femoral artery and passed into the iliac artery and aorta, into either the left or right renal artery. This comprises an intravascular path that offers minimally invasive access to a respective renal artery and/or other renal blood vessels. For example, passage through an intravascular path comprises a first vascular region and a second vascular region deviating from the first vascular region at an angular junction.

An angular junction could, for example, be the junction of the left/right renal arteries and the aorta. Such an angular junction requires significant flexure of the apparatus in order to gain entry into the respective left or right renal artery;

A force transmitting section is sized and configured to possess selected mechanical properties that accommodate physical passage through and the transmission of forces within the intravascular path. For example, as it leads from an accessed femoral artery (left or right), through the respective iliac branch artery and into the aorta, and in proximity to the targeted renal artery (left or right).

The axis of the elongated shaft, as used above, refers to the longitudinal access of the elongated shaft.

The proximal region of the apparatus refers to the proximal end region of the elongated shaft. This region may include, for example, the handle and the force transmitting section of the apparatus.

The distal region or distal section of the apparatus refers to the distal end region of the apparatus; the end of the apparatus that is furthest away from the handle. The distal end region includes, for example, a first or proximal flexure zone, a second or intermediate flexure zone, and/or a distal flexure zone.

The first flexure zone refers to the flexure zone that is closest to the proximal end region of the apparatus. The first flexure zone is equivalent to the proximal flexure zone (see discussion of FIGS. 11A to 11C above). The first or proximal flexure zone is proximal to the handle or the force transmitting section, which is part of the proximal end region.

The first flexure zone or proximal flexure zone may also be referred to as a proximal section. The proximal section may be flexible to enable it to be placed into the angular junction. For example, a proximal flexible section is adapted to bend within a guide catheter to form a transitional bend.

A transitional bend that is supported and stable within the vasculature is defined as a proximal flexure zone or proximal section.

The second flexure zone refers to the flexure zone distal from the first flexure zone (or proximal flexure zone). In embodiments having more than two flexure zones, the second flexure zone is equivalent to the intermediate flexure zone described in more detail above. The thermal element may be supported by the second or intermediate flexure zone. In embodiments having only two flexure zones, the second flexure zone is equivalent to the distal flexure zone outlined above.

The second flexure zone or intermediate flexure zone may also be referred to as an intermediate section. The intermediate section may be deflectable to enable it to extend distally from an angular junction. For example, an intermediate section may extend distally from a transitional bend of a flexible proximal section.

The third flexure zone refers to the flexure zone distal to the second flexure zone (or intermediate flexure zone). The third flexure zone is equivalent to the distal flexure zone described in more detail above. The thermal element may be carried at the end of or coupled to the distal flexure zone. The thermal element is positioned at the distal end or buttresses the distal end of the distal flexure zone.

The third flexure zone or distal flexure zone may also be referred to as a flexible distal section. The flexible distal section may extend distally from an intermediate section, as described in more detail above.

The thermal element may be any suitable element for thermal heating. The thermal element is sized and configured for manipulation and use within a renal artery. The thermal element is coupled to or carried by the distal flexure zone. Additionally, the distal flexure zone is configured to orient a portion of the thermal element alongside a region of tissue, thereby providing consistent tissue contact at each treatment location. The distal flexure zone also biases the thermal heating element against tissue, thereby stabilizing the thermal element.

The apparatus may further comprise a second thermal element coupled to the second or intermediate flexure zone, wherein the second thermal element is configured to contact the first wall region of the peripheral blood vessel.

The distal flexure zone separates the thermal element from the elongated shaft. In certain embodiments of the disclosure, the apparatus may have only one flexure zone, i.e. a distal flexure zone. The distal flexure zone having the flexible structure creates a region of electrical isolation between the thermal element and the rest of the elongated shaft, whereby the thermal element is operatively coupled to the rest of the apparatus via at least one supply wire.

In one embodiment, the distal flexure zone is approximately 2 to 5 mm in length. In other embodiments, however, the distal flexure zone can be as long as about 1 cm.

In some embodiments, the length of the intermediate flexure zone can range from approximately 5 mm to 15 mm. In other embodiments, particularly for treatments in relatively long blood vessels, the length of the intermediate flexure zone can be as long as about 20 mm. In another embodiment, the length of the intermediate flexure zone can be about 12.5 mm.

A flexure control element may be coupled to the first or second flexure zones, or proximal, or intermediate flexural zones. The flexure control element is configured to apply a force to the coupled zone such that the zone flexes in a radial direction from the axis of the longitudinal axis of the zone. The flexure control element may be carried by the handle.

A flexure controller is coupled to the flexure control element and can be operated to cause the flexure control element to apply a first force suitable to flex or move the respective zone that is coupled to the flexure control element. The flexure controller may be part of or coupled to the handle of the apparatus, catheter apparatus or device.

The flexure control element and flexure controller may be part of a control mechanism coupled to first, second, proximal, or intermediate zones. The control mechanism may include a flexure controller in the form of a control wire attached/coupled to the distal end portion of the respective zone. The control wire may be passed proximally through or alongside the elongated shaft of the apparatus/device and coupled to a flexure controller in the form of an actuator on or part of the handle.

Operation of the actuator by the caregiver pulling proximally on or pushing forward the actuator pulls the control wire back to apply a compressive and/or bending force to the coupled flexure zone resulting in bending. The compressive force in combination with the optional directionally biased stiffness of the flexure zone deflects the flexure zone and, thereby, radially moves the flexure zone with respect to its longitudinal axis.

Desirably, as described in more detail above, the distal end region of the elongated shaft can be sized and configured to vary the stiffness of the flexure zone(s) about its circumference. The variable circumferential stiffness imparts preferential and directional bending to the flexure zone (i.e., directionally biased stiffness). In response to operation of the actuator, the flexure zone may be configured to bend in a single preferential direction. The compressive and/or bending force and resulting directional bending from the deflection of the flexure zone has the consequence of altering the axial stiffness of the flexure zone. The actuation of the control wire serves to increase the axial stiffness of the flexure zone. The directionally biased stiffness of the flexure zone causes the flexure zone to move in a predetermined radial direction in response to a first force applied by the flexure control element.

The stiffness of each of the flexure zones, such as the first and the second flexure zones, can apply via the thermal element a stabilizing force that positions the thermal element in substantially secure contact with the tissue surface during actuation of the flexure control element. This stabilizing force also influences the amount of tissue surface contact achieved by the thermal heating element (i.e., the ASA to TSA ratio). In one embodiment, for example, the stabilizing force may cause at least twenty-five percent of the total surface area of the thermal element to contact the tissue surface.

A second flexure element is part of or coupled to the distal flexure zone, which may be the second or third flexure zone. The second flexure element is also coupled to the thermal element. The second flexure element has mechanical properties that accommodate additional flexure or bending, independent of the proximal flexure zone and the intermediate flexure zone, at a preferred treatment angle α3. The second flexure element may be or have a flexible structure.

A flexible structure accommodates passive flexure of the thermal element in any plane through the axis of the elongated shaft. The thermal element may flex up to ninety degrees, or less than or equal to ninety degrees from the axis.

The flexible structure may be in the form of a thread, such as a polymer thread. It is desirable for thread be comprised of Kevlar or similar polymer thread. The thread may be encased in or covered with a coating or wrapping, such as a polymer coating. The thread may be covered with a polymer laminate, coating, or sheath that can be comprised of any electrically insulative material, and particularly those listed above with respect to the sheath (e.g., carbothane). The flexible structure may further comprise a metal coil.

The thread may mechanically couple the flexible structure to at least one of the thermal element and the elongated shaft. In one embodiment, the thread is routed through a proximal anchor, which is attached to the distal end of a flexure zone (e.g., intermediate flexure zone), and a distal anchor, which is fixed within or integrated into the thermal element using solder.

The flexible structure can include, for example, a spring-like flexible tubular structure as described in more detail above. Alternatively, the flexible structure may be in the form of a tubular metal coil, cable, braid or polymer. The flexible structure can take the form of an oval, rectangular, or flattened metal coil or polymer. In alternate embodiments, the flexible structure may comprise other mechanical structures or systems that allow the thermal element to pivot in at least one plane of movement. For example, the flexible structure may comprise a hinge or ball/socket combination.

Not under the direct control of the physician, passive flexure of the second flexure element at the distal flexure zone occurs in response to contact between the thermal element and wall tissue occasioned by the radial deflection of the thermal element at the first, second or intermediate flexure zone.

The force transmitting section is sized and configured for transmitting along a compound flexure or compound structure of the elongated shaft.

A compound structure in the elongated shaft is formed by the flexure of the proximal, intermediate, and distal flexure zones. The compound structure positions a thermal element carried by the distal flexure zone for placement in contact with tissue along the intravascular path, A connector on or carried by the handle is configured to connect the thermal element to a thermal energy source. The connector may be a cable plugged into or operatively attached to the handle. The energy source may be a generator or any other energy source. At least one supply wire may pass along the elongated shaft or through a lumen in the elongated shaft from the cable plugged into or operatively attached to the handle to convey the energy to the thermal element.

The energy supplied to the thermal element may be at least one of radiofrequency, microwave energy, ultrasound energy, laser/light energy, thermal fluid, and cryogenic fluid. The thermal element may be an electrode for applying radiofrequency energy.

Additionally, a sensor such as a temperature sensor (e.g., thermocouple, thermistor, etc.), optical sensor, microsensor or impedance sensor can be located adjacent to, on or within the thermal element. The sensor can monitor a parameter of the apparatus and/or the tissue surface. The sensor may be connected to one or more supply wires. With two supply wires, one wire could convey the energy to the thermal heating element and one wire could transmit the signal from the sensor. Alternatively, both wires could transmit energy to the thermal heating element.

A feedback control system is configured to alter treatment delivered to the tissue surface in response to the monitored parameter. The feedback control system may form part of the catheter or may be attached to the energy source, such as a generator. The feedback control system may be a processor coupled to the catheter or the energy source. The sensor data can be acquired or monitored by the feedback control system prior to, simultaneous with, or after the delivery of energy or in between pulses of energy, when applicable. The monitored data may be used in a feedback loop to better control therapy, e.g., to determine whether to continue or stop treatment, and it may facilitate controlled delivery of an increased or reduced power or a longer or shorter duration therapy.

The feedback control system, such as the generator, can include an algorithm for controlling the delivery/output of energy to the thermal element. The algorithm can be implemented, for example, as a conventional computer program for execution by a processor coupled to the energy source.

The handle may comprise a rotating fitting coupled to the elongated shaft and configured to rotate the elongated shaft about the axis without rotating the handle. The rotating fitting can comprise a rotational limiting element configured to prevent rotation of the elongated shaft beyond a predetermined number of revolutions.

The rotational limiting element may be in the form of an axial groove and the distal portion of the handle can include a fitting interface having a helical channel. A traveling element, for example in the form of a ball comprising stainless steel, another metal, or a polymer, can be placed within the fitting interface so that it, upon rotation of the fitting, may simultaneously travel within the helical channel of the fitting interface and along the axial groove of the fitting. When the ball reaches the end of the channel and/or groove, the ball will no longer move and, consequently, the fitting will not be able to rotate any further in that direction, i.e. the travel of the traveling element is limited by the structural confines of the interface. The rotational fitting and handle fitting interface can be configured to allow for the optimal number of revolutions for the shaft, given structural or dimensional constraints (e.g., wires). For example, the components of the handle could be configured to allow for two revolutions of the shaft independent of the handle.

A controlled flexure zone may comprise a first or proximal flexure zone or second or intermediate flexure zone. The controlled flexure zone refers to the part of the elongated shaft that may be controlled by a remotely controlled element. The controlled flexure zone may be in the form of a tubular structure.

A remotely controlled element may be in the form of, but is not limited to, a control wire attached to the distal end of the controlled flexure zone. The control wire may be passed proximally through the elongated shaft of the apparatus and coupled to an actuator on or part of the handle. An operator may remotely operate the actuator by pulling proximally on or pushing forward the actuator and pulling the control wire back to apply a compressive and/or bending force to the flexure zone resulting in bending. The compressive force in combination with the optional directionally biased stiffness of the controlled flexure zone deflects the controlled flexure zone and, thereby, radially moves the controlled flexure zone with respect to its longitudinal axis.

Desirably, as described in more detail above, the distal end region of the elongated shaft can be sized and configured to vary the stiffness of the flexure zone(s) about its circumference. The variable circumferential stiffness imparts preferential and directional bending to the controlled flexure zone (i.e., directionally biased stiffness). This enables the flexure of the controlled flexure zone in a predetermined radial direction. In response to operation of the actuator, the controlled flexure zone may be configured to bend in a single preferential direction. The compressive and bending force and resulting directional bending from the deflection of the controlled flexure zone has the consequence of altering the axial stiffness of the controlled flexure zone. The actuation of the control wire serves to increase the axial stiffness of the controlled flexure zone. The directionally biased stiffness of the controlled flexure zone causes the flexure zone to move in a predetermined radial direction in response to a first force applied by the flexure control element.

The stiffness of the controlled zone can apply via the thermal element a stabilizing force that positions the thermal element in substantially secure contact with the tissue surface, during actuation of the flexure control element. This stabilizing force also influences the amount of tissue surface contact achieved by the thermal heating element (i.e., the ASA to TSA ratio). In one embodiment, for example, the stabilizing force may cause at least twenty-five percent of the total surface area of the thermal element to contact the tissue surface.

The controlled flexure zone in the form of a tubular structure may provide the directionally biased stiffness. The tubular structure may be made of a metal material, e.g. of stainless steel, or a shape memory alloy, e.g., nickel titanium (a.k.a., nitinol or NiTi), to possess the requisite axial stiffness and torsional stiffness. The tubular structure may comprise a tubular polymer or metal/polymer composite having segments with different stiffnesses. The tubular structure may be in the form of an oval, or rectangular, or flattened metal coil or polymer having segments with different stiffnesses.

The tubular structure, when made from metal, may be laser cut. For example, the tubular structure may be laser cut along its length to provide a bendable, spring-like structure. The tubular structure can include a laser-cut pattern having a spine with a plurality of connecting ribs. The pattern biases the deflection of the tubular structure, in response to pulling on the control flexure element coupled to the distal end of the tubular structure, toward a desired direction. The directionally-biased stiffness of the tubular structure may be determined by the location of the spine in relation to the plurality of connecting ribs on the tubular structure.

The tubular structure may further comprise a polymer laminate, coating, or sheath.

An unrestrained flexure zone is distal to the controlled flexure zone. The unrestrained flexure zone has or is coupled to a thermal or tissue heating element. The unrestrained flexure zone has mechanical properties that accommodate additional flexure or bending, independent to or in response to the flexure of the controlled flexure zone. The unrestrained flexure zone may have or be coupled to a flexible structure as described in more detail above.

The apparatus may further comprise a second thermal element coupled to the controlled flexure zone, wherein the second thermal element is configured to contact the first wall region of the peripheral blood vessel.

A connector on or carried by the handle is configured to connect the thermal element to a thermal energy source. The connector may be a cable plugged into or operatively attached to the handle. The energy source may be a generator or any other energy source. At least one supply wire may pass along the elongated shaft or through a lumen in the elongated shaft from the cable plugged into or operatively attached to the handle convey the energy to the thermal element.

The elongated shaft may be configured for rotation within the peripheral blood vessel when the controlled flexure zone is in flexure against the first wall region and when the thermal element is in contact with the second wall region. Rotation of the elongated shaft positions the controlled flexure zone against a third wall region and positions the thermal element against a fourth wall region, wherein the third wall region is circumferentially offset from the first wall region and the fourth wall region is circumferentially offset from the second wall region, and wherein the third wall region is generally opposite the fourth wall region.

As described in more detail above, the apparatus of the disclosure may form part of a system. The system may further comprise instructions that command the energy generator/source to deliver energy to the thermal element according to a predetermined energy delivery profile. The predetermined energy delivery profile may comprise increasing energy delivery to a predetermined power level for a first period of time, maintaining energy delivery at the first power level for a second period of time; and increasing energy delivery to a second power level if the temperature value is less than a preset threshold following the second period of time.

As described in more detail above, the apparatus of the disclosure may be provided in the form of a kit, such as a medical kit. The kit may further comprise a cable configured to electrically connect the catheter apparatus to the thermal energy source and a dispersive electrode configured to provide a return path for an energy field from the catheter. The kit may further comprise one or more guide catheters (e.g., a renal guide catheter). The cable can also be integrated into the apparatus such that both components are packaged together. Each component may have its own sterile packaging (for components requiring sterilization) or the components may have dedicated sterilized compartments within the kit packaging.

The kit may further comprise instructions for delivering the catheter apparatus into a renal artery of the patient and at least partially denervating the kidney corresponding to the renal artery to treat the patient for a condition associated with at least one of hypertension, heart failure, kidney disease, chronic renal failure, sympathetic hyperactivity, diabetes, metabolic disorder, arrhythmia, acute myocardial infarction and cardio-renal syndrome VIII. Conclusion The above detailed descriptions of embodiments of the invention are not intended to be exhaustive or to limit the invention to the precise form disclosed above. Although specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order. The various embodiments described herein can also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the invention. Where the context permits, singular or plural terms may also include the plural or singular term, respectively. For example, much of the disclosure herein describes a thermal heating element 24 or electrode 46 in the singular. It should be understood that this application does not exclude two or more thermal heating elements or electrodes. In one embodiment representative of a multi-electrode configuration, a second electrode could be placed on the intermediate flexure zone 34 opposite the direction of deflection of the intermediate flexure zone 34 such that the second electrode could deliver treatment to the vessel wall at or near contact region 124. This approach would allow two spaced apart treatments per position of the treatment device, one distal treatment via the first electrode 46 and one proximal treatment via the second electrode.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the invention. Accordingly, the invention is not limited except as by the appended claims.

We claim:

1. A neuromodulation treatment device, comprising:
   an elongated shaft having a proximal end region and a distal end region, the distal end region including a first flexure zone, a portion of the first flexure zone being configured to rest in an aorta of a patient and a remaining portion configured to rest in a renal artery of the patient, and a second flexure zone that is distal to the first flexure zone, the first flexure zone and the second flexure zone being configured to flex about an axis of the elongated shaft; and
   a neuromodulation element carried by the second flexure zone and configured to apply treatment to a tissue region,
   wherein the second flexure zone is an unrestrained flexure zone configured to passively flex in any plane about the axis in response to an applied force from the neuromodulation element contacting a tissue surface.

2. The neuromodulation treatment device of claim 1, wherein the portion of the first flexure zone is configured to rest and be supported by a wall of the aorta, wherein the remaining portion of the first flexure zone is configured to rest and be supported by a wall of the renal artery.

3. The neuromodulation treatment device of claim 1, wherein the first flexure zone defines a transitional bend that is configured to be supported and stable within vasculature of the patient.

4. The neuromodulation treatment device of claim 1 further comprising:
   a flexure control element coupled to the first flexure zone and configured to apply a force to the first flexure zone to move the first flexure zone away from the axis.

5. The neuromodulation treatment device of claim 4, further comprising:
   a flexure controller coupled to the flexure control element and configured to cause the flexure control element to apply the force to the first flexure zone.

6. The neuromodulation treatment device of claim 1, further comprising:
   a handle coupled to the proximal end region of the elongated shaft; and
   a rotating fitting coupled to the handle and configured to rotate the elongated shaft.

7. The neuromodulation treatment device of claim 6, wherein the rotating fitting is mounted on a tab that is carried in a circumferential channel on a distal end of the handle.

8. The neuromodulation treatment device of claim 6, wherein the rotating fitting is configured to rotate independently of the handle and rotate the elongated shaft without rotating the handle.

9. The neuromodulation treatment device of claim 1, wherein the second flexure zone has a flexible structure that is coupled to the neuromodulation element and that allows the second flexure zone to flex in any plane about the axis.

10. The neuromodulation treatment device of claim 1, further comprising a flexure controller at a proximal portion of the neuromodulation treatment device, wherein the flexure controller is configured to cause movement of the first flexure zone away from the axis, and wherein the flexure controller is not coupled to the second flexure zone.

11. A neuromodulation treatment device, comprising:
    an elongated shaft having a proximal end region and a distal end region, the distal end region including a controlled flexure zone, a portion of the controlled flexure zone being configured to be within an aorta of a patient and a remaining portion configured to be within a renal artery of the patient, and an unrestrained flexure zone that is distal to the controlled flexure zone, the controlled flexure zone and the unrestrained flexure zone being configured to move about an axis in response to an applied force;
    a handle coupled to the proximal end region of the elongated shaft;
    a rotating fitting coupled to the handle and configured to rotate the elongated shaft; and
    a neuromodulation element carried by the unrestrained flexure zone and configured to apply treatment to a tissue region,
    wherein the unrestrained flexure zone is configured to passively flex in any plane about the axis in response to an applied force from the neuromodulation element contacting a tissue surface.

12. The neuromodulation treatment device of claim 11, further comprising:
a flexure control element coupled to the controlled flexure zone and configured to apply a force to the first controlled flexure zone to move the controlled flexure zone away from the axis.

13. The neuromodulation treatment device of claim 12, further comprising:
a flexure controller coupled to the flexure control element and configured to cause the flexure control element to apply the first force to the controlled flexure zone.

14. The neuromodulation treatment device of claim 11, wherein the portion of the controlled flexure zone is configured to rest and be supported by a wall of the aorta, wherein the remaining portion of the controlled flexure zone is configured to rest and be supported by a wall of the renal artery, wherein the controlled flexure zone defines a transitional bend that is configured to be supported and stable within vasculature of the patient.

15. The neuromodulation treatment device of claim 11, wherein the rotating fitting is configured to rotate independently of the handle and rotate the elongated shaft without rotating the handle.

16. The neuromodulation treatment device of claim 11, wherein the unrestrained flexure zone has a flexible structure that is coupled to the neuromodulation element and that allows the unrestrained flexure zone to flex in any plane about the axis.

17. The neuromodulation treatment device of claim 11, further comprising a flexure controller at a proximal portion of the neuromodulation treatment device, wherein the flexure controller is configured to cause movement of the controlled flexure zone away from the axis, and wherein the flexure controller is not coupled to the unrestrained flexure zone.

18. A treatment device, comprising:
an elongated shaft having a proximal end region and a distal end region, the distal end region including a first flexure zone, a portion of the first flexure zone being configured to rest in an aorta of a patient and a remaining portion configured to rest in a renal artery of the patient, and a second flexure zone that is distal to the first flexure zone, the first flexure zone defining a transitional bend that is configured to be supported and stable within vasculature of the patient;
an electrode carried by the second flexure zone configured to apply treatment to a tissue region; and
a flexure control element coupled to the first flexure zone and configured to apply a first force to the first flexure zone to move the first flexure zone away from an axis,
wherein the second flexure zone is an unrestrained flexure zone configured to passively flex in any plane about the axis in response to an applied force from the neuromodulation element contacting a tissue surface, wherein flexing of the second flexure zone is not directly controlled by the flexure control element.

19. The treatment device of claim 18, further comprising:
a handle coupled to the proximal end region of the elongated shaft; and
a rotating fitting coupled to the handle and configured to rotate the elongated shaft.

20. The treatment device of claim 18, wherein the rotating fitting is mounted on a tab that is carried in a circumferential channel on the distal end of the handle.

* * * * *